Figure 11:
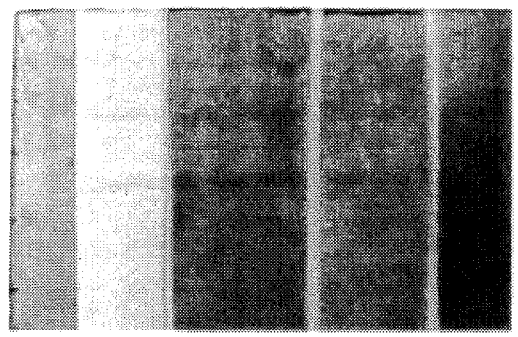
Figure 12:
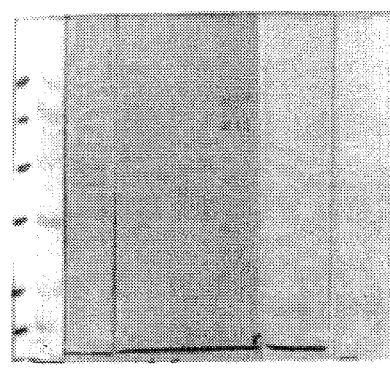

United States Patent [19]

Alstyne et al.

[11] Patent Number: 5,556,757
[45] Date of Patent: Sep. 17, 1996

[54] PEPTIDES REPRESENTING EPITOPIC SITES FOR BACTERIAL AND VIRAL MENINGITIS CAUSING AGENTS AND THEIR CNS CARRIER AND USES THEREOF

[75] Inventors: Diane V. Alstyne; Lawrence R. Sharma, both of Vancouver, Canada

[73] Assignee: Insight Biotek, Inc., St. Michaels, Barbados

[21] Appl. No.: 482,847

[22] Filed: Jun. 7, 1995

Related U.S. Application Data

[62] Division of Ser. No. 127,499, Sep. 28, 1993.

[51] Int. Cl.$^6$ .................. G01N 33/53; G01N 33/554; G01N 33/569; C07K 7/00
[52] U.S. Cl. .................. 435/7.2; 435/7.32; 435/7.34; 530/300; 530/324; 530/327; 530/329; 514/2
[58] Field of Search .................. 435/7.2, 7.32, 435/7.34; 530/300, 324, 327, 329; 514/2

[56] References Cited

PUBLICATIONS

Roos "Chapter 16", Sheld, et al. eds., *Infections of the CNS* :335 (1991).
Herrmann "Rubella Virus", *Diagnostic Procedures for Viral, Rickettsial and Chlamydial Infections* :725 (1979).
Spalding "In Hot Pursuit of an HIV Vaccine", *Biotech* 10:24–29 (1992).
Green et al. EMBL Bank (1992).
Griffiss et al. "Vaccines Against Encapsulated Bacteria: A Global Agenda", *Rev. Infec. Dis*. 9:176–188 (1987).
Yoshimura et al. "Human monocyte chemoattractant protein-1 (MCP–1)", *FEBS Letters* 244:487–493 (1989).
Terry et al. "Localization of the rubella E1 epitopes", *Arch. Virol*. 98:189–197 (1988).
Connolly et al. "Carotid Artery Thrombosis, Encephalitis, Myelitis and Optic Neuritis Associated with Rubella Virus Infections", *Brain* 98:583–594 (1975).
Pope and "Van Alstyne Evidence for Restricted Replication of rubella Virus in Rat Glial Cells in Culture", *Virology* 113:776–780 (1981).
Van Alstyne and Paty "The Effect of Dibutyryl Cyclic AMP on Restricted Replication of Rubella Virus in Rat Glial Cells in Culture", *Virology* 124:173–180 (1983).
Voller and Bidwell "A Simple Method for Detecting Antibodies to Rubella", *Br. J. Exp. Path*. 56:338–339 (1975).
Parkman and Meyer et al. "Attenuated Rubella Virus", *The New England Journal of Medicine* 275:569–580 (1966).
Stephens et al. "Equine Infectious Anemia Virus gag and pol Genes: Relatedness to the Visna and AIDS Virus", *Science* 231:589–594 (1986).
Ho et al. "Primary Human T–Lymphotropic Virus Type III Infection", *Annals of Internal Medicine* 103:880–883 (1985).

Muesing et al. "Nucleic acid structure and expression of the human AIDS/lymphadenopathy retrovirus", *Nature* 313:450–458 (1985).
Fraser et al. "Bacterial Meningitis in Bernililo County, New Mexico: A Comparison with Three Other American Populations", *Am. J. of Epidemology* 100:29–34 (1974).
Yother and Briles "Structural Properties and Evolutionary Relationships of PspA, a Surface Protein of *Streptococcus pneumoniae* as Revealed by Sequence Analysis", *J. of Bacteriology* 174:601–609 (1992).
Tunkel et al. "Bacterial Meningitis: Recent Advances in Pathophysiology and Treatment", *Annals of Internal Medicine* 112:610–623 (1990).
Stern and Meyer "Common mechanism controlling phase and antigenic variation in pathogenic neisseriae", *Molecular Microbiology* 1:5–12 (1987).
Goebel et al. "Studies on the Pathogenicity of *Listeria monocytogenes*", *Infection* 19:S195–197 (1991).
Michel and Cossart "Physical Map of the *monocytogenes* Cromosome", *Journal of Bacteriology* 174:7098–7103 (1992).
Kohler et al. "The Gene Coding for Protein p60 of *Listeria monocytogenes* and Its Use as a Specific Probe for *Listeria monocytogenes*", *Infection and Immunity* 58:1943–1950 (1990).
Cordy "Pathomorphiology and Pathogenesis of Bacterial Meningoventriculitis of Neonatal Ungulates", *Vet. Pathol.* 21:587–591 (1984).
Robinson et al. "Complete amino acid sequence of a human monocyte chemoattractant, a putative mediator of cellular immune reactions", *Proc. Natl. Acad. Sci. USA* 86:1850–1854 (1989).
Michiel et al. "Chemokines: The Missing Link", *Bio/technology* 11:739 (1993).
Rollins et al. "The Human Homolog of the JE Gene Encodes a Monocyte Secretory Protein", *Molecular and Cellular Biology* 9:4687–4695 (1989).
Van Damme et al. "Structural and Functional Identification of Two Human, Tumor–derived Monocyte Chemotactic Proteins (MCP–2 and MCP–3) Belonging to the Chemokine Family", *J. Exp. Med.* 176:59–64 (1992).
Green et al. "The e (P4) Outer Membrane Protein of *Haemophilus influenzae*: Biologic Activity of Anti–e Serum and Cloning and Sequencing of the Structural Gene, " *Infection and Immunology* 59:3191–3198 (1991).
Waldmann, T. A. *Science* 252:1657–1662 (1991).
Waxham et al. *Virology* 143:153–165 (1985).

*Primary Examiner*—Margaret Parr
*Assistant Examiner*—Susan A. Loring
*Attorney, Agent, or Firm*—Foley & Lardner

[57] ABSTRACT

Peptides comprising a Meningitis Related Homologous Antigenic Sequence (MRHAS) are provided. The MRHAS is found in meningitis-causing organisms and chemokines involved in cell chemotaxis. The peptides are useful as antigens and vaccines for detection, diagnosis and treatment of meningitis.

**2

FIG. 1

```
            10         20         30         40         50
  1 MASTTPITME DLQKALEAQS RALRAGLAAG ASQSRRPRPP RHARLQHLPE       50
            60         70         80         90        100
 51 MTPAVTPEGP APPRTGAWQR KDWSRAPPPP EERQESRSQT PAPKPSRAPP      100
           110        120        130        140        150
101 QQPQPPRMQT GRGGSAPRPE LGPPTNPFQA AVARGLRPPL HDPDTEAPTE      150
           160        170        180        190        200
151 ACVTSWLWSE GEGAVFYRVD LHFINLGTPP LDEDGRWDPA LMYNPCGPEP      200
           210        220        230        240        250
201 PAHVVRAYNQ PAGDVRGVWG KGERTYAEQD FRVGGTRWHR LLRMPVRGLD      250
           260        270        280        290        300
251 GDTAPLPPHT TERIETRSAR HPWRIRFGAP QAFLAGLLLA AVAVGTARAG      300
           310        320        330        340        350
301 LQPRADMAAP PMPPQPPRAH GQHYGHHHHQ LPFLGHDGHH GGTLRVGQHH      350
           360        370        380        390        400
351 RNASDVLPGH WLQGGWGCYN LSDWHQGTHV CHTKHMDFWC VEHDRPPPAT      400
           410        420        430        440        450
401 PTSLTTAANY IAAATPATAP PPCHAGLNDS CGGFLSGCGP MRLPTALTPG      450
           460        470        480        490        500
451 AVGDLRAVHH RPVPAYPVCC AMRWGLPPWE LVILTARPED GWTCRGVPAH      500
           510        520        530        540        550
501 PGTRCPELVS PMGRATCSPA SALWLATANA LSLDHAFAAF VLLYPWVLIF      550
           560        570        580        590        600
551 MVCRRACRRP APPPPSPQSS CRGTTPPAYG EEAFTYLCTA PGCATQTPVP      600
           610        620        630        640        650
601 VRLAGVGFES KIVDGGCFAP WDLEATGACI CEIPTDVSCE GLGAWVPTAP      650
           660        670        680        690        700
651 CARIWNGTQR ACTFWAVNAY SSGGYAQLAS YFNPGGSYYK QYHPTACEVE      700
           710        720        730        740        750
701 PAFGHSDAAC WGFPTDTVMS VFALASYVQH PHKTVRVKFH TETRTVWQLS      750
           760        770        780        790        800
751 VAGVSCNVTT EHPFCNTPHG QLEVQVPPDP GDLVEYIMNY TGNQQSRWGL      800
           810        820        830        840        850
801 GSPNCHGPDW ASPVCQRHSP DCSRLVGATP ERPRLRLVDA DDPLLRTAPG      850
           860        870        880        890        900
851 PGEVWVTPVI GSQARKCGLH IRAGPYGHAT VEMPEWIHAH TTSDPWHPPG      900
           910        920        930        940        950
901 PLGLKFKTVR PVALPRALAP PRNVRVTGCY QCGTPALVEG LAPGGGNCHL      950
           960        970        980        990       1000
951 TVNGEDVGAF PPGKFVTAAL LNTPPPYQVS CGGESDRASA GH........    1000
```

```
         10          20          30          40          50
         ....|....  ....|....  ....|....  ....|....  ....|....
  1  MGARASVLSG GELDRWEKIR LRPGGKKKYK LKHIVWASRE LERFAVNPGL       50

60          70          80          90         100
         ....|....  ....|....  ....|....  ....|....  ....|....
 51  LETSEGCRQI LGQLQPSLQT GSEELRSLYN TVATLYCVHQ RIEIKDTKEA      100

110         120         130         140         150
         ....|....  ....|....  ....|....  ....|....  ....|..-
101  LDKIEEEQNK SKKKAQQAAA DTGHSSQVSQ NYPIVQNIQG QMVHQAISPR      150

160         170         180         190         200
         ....|....  ....|....  ....|....  ....|....  ....|....
151  TLNAWVKVVE EKAFSPEVIP MFSALSEGAT PQDLNTMLNT VGGHQAAMQM      200

210         220         230         240         250
         ....|....  ....|....  ....|....  ....|....  ....|....
201  LKETINEEAA EWDRVHPVHA GPIAPGQMRE PRGSDIAGTT STLQEQIGWM      250

260         270         280         290         300
         ....|....  ....|....  ....|....  ....|....  ....|....
251  TNNPPIPVGE IYKRWIILGL NKIVRMYSPT SILDIRQGPK EPFRDYVDRF      300

310         320         330         340         350
         ....|....  ....|....  ....|....  ....|....  ....|....
301  YKTLRAEQAS QEVKNWMTET LLVQNANPDC KTILKALGPA ATLEEMMTAC      350

360         370         380         390         400
         ....|....  ....|....  ....|....  ....|....  ....|....
351  QGVGGPGHKA RVLAEAMSQV TNTATIMMQR GNFRNQRKMV KCFNCGKEGH      400

410         420         430         440         450
         ....|....  ....|....  ....|....  ....|....  ....|....
401  TARNCRAPRK KGCWKCGKEG HQMKDCTERQ ANFLGKICLP TREGQGIFFR      450

460         470         480         490         500
         ....|....  ....|....  ....|....  ....|....  ....|....
451  ADQSQQPHHF FRADQSQQPH QKRASGLG..  .........  .........     500
```

FIG. 4

```
           10         20         30         40         50
  1 MRVKEKYQHL WRWGWKWGTM LLGILMICSA TEKLWVTVYY GVPVWKEATT    50
          60         70         80         90        100
 51 TLFCASDAKA YDTEVHNVWA THACVPTDPN PQEVVLVNVT ENFNMWKNDM   100
         110        120        130        140        150
101 VEQMHEDIIS LWDQSLKPCV KLTPLCVSLK CTDLGNATNT NSSNTNSSSG   150
         160        170        180        190        200
151 EMMMEKGEIK NCSFNISTSI RGKVQKEYAF FYKLDIIPID NDTTSYTLTS   200
         210        220        230        240        250
201 CNTSVITQAC PKVSFEPIPI HYCAPAGFAI LKCNNKTFNG TGPCTNVSTV   250
         260        270        280        290        300
251 QCTHGIRPVV STQLLLNGSL AEEEVVIRSA NFTDNAKTII VQLNQSVEIN   300
         310        320        330        340        350
301 CTRPNNNTRK SIRIQRGPGR AFVTIGKIGN MRQAHCNISR AKWNATLKQI   350
         360        370        380        390        400
351 ASKLREQFGN NKTIIFKQSS GGDPEIVTHS FNCGGEFFYC NSTQLFNSTW   400
         410        420        430        440        450
401 FNSTWSTEGS NNTEGSDTIT LPCRIKQFIN MWQEVGKAMY APPISGQIRC   450
         460        470        480        490        500
451 SSNITGLLLT RDGGNNNNGS EIFRPGGGDM RDNWRSELYK YKVVKIEPLG   500
         510        520        530        540        550
501 VAPTKAKRRV VQREKRAVGI GALFLGFLGA AGSTMGARSM TLTVQARQLL   550
         560        570        580        590        600
551 SGIVQQQNNL LRAIEAQQHL LQLTVWGIKQ LQARILAVER YLKDQQLLGI   600
         610        620        630        640        650
601 WGCSGKLICT TAVPWNASWS NKSLEQIWNN MTWMEWDREI NNYTSLIHSL   650
         660        670        680        690        700
651 IEESQNQQEK NEQELLELDK WASLWNWFNI TNWLWYIKIF IMIVGGLVGL   700
         710        720        730        740        750
701 RIVFAVLSIV NRVRQGYSPL SFQTHLPTPR GPDRPEGIEE EGGERDRDRS   750
         760        770        780        790        800
751 IRLVNGSLAL IWDDLRSLCL FSYHRLRDLL LIVTRIVELL GRRGWEALKY   800
         810        820        830        840        850
801 WWNLLQYWSQ ELKNSAVSLL NATAIAVAEG TDRVIEVVQG ACRAIRHIPR   850
         860        870        880        890        900
851 RIRQGLERIL L                                             900
```

FIG. 5

```
          10         20         30         40         50
  1 MKTTLKMTAL AALSAFVLAG CGSHQMKSEE HANMQLQQQA VLGLNWMQDS    50
          60         70         80         90        100
 51 GEYKALAYQA YNAAKVAFDH AKVAKGKKKA VVADLDETML DNSPYAGWQV   100
         110        120        130        140        150
101 QNNKPFDGKD WTRWVDARQS RAVPGAVEFN NYVNSHNGKV FYVTNRKDST   150
         160        170        180        190        200
151 EKSGTIDDMK RLGFNGVEES AFYLKKDKSA KAARFAEIEK QGYEIVLYVG   200
         210        220        230        240        250
201 DNLDDFGNTV YGKLNADRRA FVDQNQGKFG KTFIMLPNAN YGGWEGGLAE   250
         260        270        280        290        300
251 GYFKKDTQGQ IKARLDAVQA WDGK......                         300
```

FIG. 6

```
           10          20          30          40          50
  1 IQPPKNLLFS  SLLFSSLLFS  SAAQAASEDR  RSPYYVQADL  AYAAERITHD   50
           60          70          80          90         100
 51 YPQATGANNT  STVSDYFRNI  RAHSIHPRVS  VGYDFGGWRI  AADYASYRKW  100
          110         120         130         140         150
101 NNNKYSVNTK  ELENKHNNKK  DLKTENQENG  TFHAASSLGL  SAIYDFKLKG  150
          160         170         180         190         200
151 KFKPYIGARV  AYGHVRHSID  ..........  ..........  ..........  200
```

FIG. 9

```
           10          20          30          40          50
  1 MKVSAALLCL  LLIAATFIPQ  GLAQPDAINA  PVTCCYNFTN  RKISVQRLAS   50
           60          70          80          90         100
 51 YRRITSSKCP  KEAVIFKTIV  AKEICADPKQ  KWVQDSMDHL  DKQTQTPKT.  100
```

FIG. 10

```
           10          20          30          40          50
  1 KSTTCCYRFI  NKKIPKQRLE  SYRRTTSSHC  PREAVIFKDK  EICADPTQKW   50
           60          70          80          90         100
 51 VQDFMKHLDK  KTQTPKL...  ..........  ..........  ..........  100
```

FIG. 7

```
                                           -11           -1
                                           ..........
                                              ....KLMI*K           6

10         20         30         40         50
          ..........  ..........  ..........  ..........  ..........
      7  FVTKM*YKTL  DKYLRRRLIL  NISIV*K*LS  EKR*I*MNKK  KMILTSLASV    56

60         70         80         90        100
          ..........  ..........  ..........  ..........  ..........
     57  AILGAGFVAS  QPTVVRAEES  PVASQSKAEK  DYDAAKKDAK  NAKKAVEDAQ   106

110        120        130        140        150
          ..........  ..........  ..........  ..........  ..........
    107  KALDDAKAAQ  KKYDEDQKKT  EEKAALEKAA  SEEMDKAVAA  VQQAYLAYQQ   156

160        170        180        190        200
          ..........  ..........  ..........  ..........  ..........
    157  ATDKAAKDAA  DKMIDEAKKR  EEEAKTKFNT  VRAMVVPEPE  QLAETKKKSE   206

210        220        230        240        250
          ..........  ..........  ..........  ..........  ..........
    207  EAKQKAPELT  KKLEEAKAKL  EEAEKKATEA  KQKVDAEEVA  PQAKIAELEN   256

260        270        280        290        300
          ..........  ..........  ..........  ..........  ..........
    257  QVHRLEQELK  EIDESESEDY  AKEGFRAPLQ  SKLDAKKAKL  SKLEELSDKI   306

310        320        330        340        350
          ..........  ..........  ..........  ..........  ..........
    307  DELDAEIAKL  EDQLKAAEEN  NNVEDYFKEG  LEKTIAAKKA  ELEKTEADLK   356

360        370        380        390        400
          ..........  ..........  ..........  ..........  ..........
    357  KAVNEPEKPA  PAPETPAPEA  PAEQPKPAPA  PQPAPAPKPE  KPAEQPKPEK   406

410        420        430        440        450
          ..........  ..........  ..........  ..........  ..........
    407  TDDQQAEEDY  ARRSEEEYNR  LTQQQPPKAE  KPAPAPKTGW  KQENGMWYFY   456

460        470        480        490        500
          ..........  ..........  ..........  ..........  ..........
    457  NTDGSMATGW  LQNNGSWYYL  NSNGAMATGW  LQYNGSWYYL  NANGAMATGW   506

510        520        530        540        550
          ..........  ..........  ..........  ..........  ..........
    507  AKVNGSWYYL  NANGAMATGW  LQYNGSWYYL  NANGAMATGW  AKVNGSWYYL   556

560        570        580        590        600
          ..........  ..........  ..........  ..........  ..........
    557  NANGAMATGW  LQYNGSWYYL  NANGAMATGW  AKVNGSWYYL  NANGAMATGW   606

610        620        630        640        650
          ..........  ..........  ..........  ..........  ..........
    607  VKDGDTWYYL  EASGAMKASQ  WFKVSDKWYY  VNGLGALAVN  TTVDGYKVNA   656

660        670        680        690        700
          ..........  ..........  ..........  ..........  ..........
    657  NGEWV*AD*I  KAC*EHLTF*  F*NKDKVRLN  RFMFVFFRY.  ..........   706
```

FIG. 8

```
              10          20          30          40          50
  1  MNMKKATIAA  TAGIAVTAFR  APTIRSASTV  VVEAGDTLWG  IAQSKGTTVD      50

60          70          80          90         100
 51  AIKKANNLTT  DKIVPGQKLQ  VNNEVAAAEK  TEKSVSATWL  NVRSGAGVDN     100

110         120         130         140         150
101  SIITSIKGGT  KVTVETTESN  GWHKITYNDG  KTGFVNGKYL  TDKAVSTPVA     150

160         170         180         190         200
151  PTQEVKKETT  TQQAAPAAET  KTEVKQTTQA  TTPAPKVAET  KETPVVDQNA     200

210         220         230         240         250
201  TTHAVKSGDT  IWALSVKYGV  SVQDIMSWNN  LSSSSIYVGQ  KLAIKQTANT     250

260         270         280         290         300
251  ATPKAEVKTE  APAAEKQAAP  VVKENTNTNT  ATTEKKETAT  QQQTAPKAPT     300

310         320         330         340         350
301  EAAKPAPAPS  TNTNANKTNT  NTNTNTNTNN  TNTNTPSKNT  NTNSNTNTNT     350

360         370         380         390         400
351  NSNTNANQGS  SNNNSNSSAS  AIIAEAQKHL  GKAYSWGGNG  PTTFDCSGYT     400

410         420         430         440         450
401  KYVFAKAGIS  LPRTSGAQYA  STTRISESQA  KPGDLVFFDY  GSGISHVGIY     450

460         470         480         490         500
451  VGNGQMINAQ  DNGVKYDNIH  GSGWGKYLVG  FGRV......  ..........     500
```

1  2/3  4/5/6  7/8  9/10

1  2  3  4/5  6/7

1  2  3/4

PEPTIDES REPRESENTING EPITOPIC SITES FOR BACTERIAL AND VIRAL MENINGITIS CAUSING AGENTS AND THEIR CNS CARRIER AND USES THEREOF

This application is a divisional of application Ser. No. 08/127,499, filed Sep. 28, 1993 allowed patent application.

FIELD OF THE INVENTION

This invention relates to the application of immunological techniques that provide novel materials useful in the diagnosis, treatment and vaccination against meningitis caused by either bacterial or viral agents. These techniques include the production and application of novel monoclonal antibodies, peptides, and mixtures and combinations thereof that are useful for detecting meningitis infections. The techniques also include eliciting antibodies specific to meningitis causing agents. These immunological techniques may also be applied to the treatment of such disease.

BACKGROUND OF THE INVENTION

The term meningitis is a general one, referring to the inflammatory response to infection of the meninges and the cerebrospinal fluid (CSF). See Roos, "Chapter 16", in Scheld, et al. eds., 1991, *Infections of the Central Nervous System*:335–403 which is incorporated herein in its entirety by reference.

The fact that the inflammatory response occurs in the proximity of the brain and in the space limited by a rigid cranium, makes these infections serious and life threatening. Most patients exhibit nonspecific clinical signs and symptoms such as fever, irritability, altered mental status usually accompanied by vomiting and loss of appetite. In children one year of age and older, photophobia and headache are common complaints. Specific clinical signs indicative of meningitis are neck rigidity and pain on neck flexion. Brudzinski's sign (neck flexion producing knee and hip flexion) and Kernig's sign (difficulty and pain in raising extended leg) are other useful clinical signs.

In infants less than 6 months old, early diagnosis of meningitis is difficult because signs of meningitis are not prominent and neck rigidity is often absent. Such patients commonly exhibit fever, respiratory distress, other signs of sepsis, and convulsions. Bulging anterior fontanelle due to increased intracranial pressure may be the only specific sign.

Petechiae (or rash) is most commonly present in meningococcal infections. In severe meningococcal infections with bacteraemia, petechiae and shock may develop with alarming rapidity. Convulsions at some point in the illness occur in about 30% of the cases. This number is often higher in neonares and infants under one year of age. Other acute complications include septic shock, disseminated intravascular coagulation, syndrome of inappropriate antidiuretic hormone, increased intracranial pressure, and diabetes insipidus. Convulsions and coma appearing with 24 hours accompanied by high fever indicates serious infection (Stutman & Marks, 1987, *Clin. Ped.* 26:432–438).

A diverse array of both bacteria and viruses cause meningitis, the infectivity of which is dependent on a complex array of factors, including virulence of the organisms, the carrier state, and the host's humoral immune response.

Viruses generally cause milder forms of meningitis (eg. meningomyelitis and aseptic meningitis) with a short clinical course and reduced mortality. Agents most commonly associated are coxsackievirus A (types 2,4,7,9,10), B (types 1–6), polio virus, echoviruses (types 1–34, except 12,24,26, 29,32–34), enteroviruses (types 70, 71), human immunodeficiency virus-1 (HIV-1), and rubella virus (RV). See Melnick, "Chapter 33" and Cooper, "Chapter 42" in Fields, et al., eds., 1985, *Virology*: 739–794 and 1005–1032, respectively; and Rotbart, "Chapter 3", in Scheld et al., 1991, infra:19–33 which are all incorporated herein by reference.

Rubella is possibly the most common cause of viral meningitis. Moreover, the most common chemical sequelae of rubella infection of young children are meningitis, meningomyelitis and rubella associated panencephalitis. Rubella is a highly contagious disease, usually associated with childhood, and is characterized by a general rash and a mild fever. Sub-clinical infections are also common. Its clinical aspects have been confused with measles, which it closely resembles. Since its early discovery in Germany, Rubella is often referred to as German measles. The infection of a pregnant woman poses the greatest risk when infection of the fetus can lead to spontaneous abortion or an array of abnormalities called the Congenital Rubella Syndrome in the newborn. Damage most frequently involves cardiac abnormalities, deafness, cataracts, blindness and Central Nervous System (CNS) disorders including microencephaly.

The rubella virion is a spherical, enveloped virus, approximately 60 nm in diameter, and is a member of the Togaviridae. It's genome is a 10 Kb plus single-stranded RNA. The outer envelope is comprised of lipoproteins derived from the infected host cell, and it appears to have two viral encoded glycoproteins, E1 (58 Kd) and E2 (42–47 Kd), responsible for the hemagglutination activity of the virus. Its core protein is a non-glycosylated nucleocapsid protein with an approximate weight of 33 Kd. It appears that the core, E1, and E2 are all derived from the same parent protein—Structural Polyprotein. See Clark et al., 1987, *Nucl. Acids Res.* 15:3041–3057; Dominguez, et al., 1990, *Virolcgy* 177:225–238, both which are incorporated herein by reference. Three strains of wild type RV (M33, Therien, Judith) and a vaccine strain (HPV77) of RV have been identified and sequenced (Zheng et alo, 1988, *Arch. Virol.* 98:189–197 incorporated herein in its entirety by reference). Between these different wild types strains, there exists minor variations in the amino acid sequence of the Structural Polyprotein (Dominguez, infra; Clarke, infra).

The detection of RV in diagnosis has in the past proven difficult, largely because the virus grows to low titers in the tissue cultures and is highly liable, making it technically difficult to isolate and purify (Ho-Terry et al., 1986, *Arch. Virol.* 87: 219–228).

The detection of RV in the CNS presents additional technical problems. It has been known since 1941 that the RV can infect cells of the CNS (Gregg, 1941, *Trans. Ophthalmol. Soc. Aust.* 3:35–46). However, it has proven difficult to reliably demonstrate the presence of the RV in infected brain tissue. Persistent infection of the CNS has been well documented in the congenital rubella syndrome (Desmond et al., 1967, *J. Pediat.*, 7:311–331), and in the neuropathology if progressive rubella panencephalitis of late onset occurs where the virus has been isolated from brain biopsy material (Townsend et al., 1975, *N. Engl. J. Med.* 292:990–993; Cremer et al., 1979, *J. Gen. Virol.* 29:143–153). Less commonly documented are the wide range of neuropathies known to follow exposure to the RV. These include encephalitis, meningomyelitis, and bilateral optic neuritis (Connolly et al., 1975, *Brain* 98:583–594). Moreover, the report of a diffuse myelitis following RV in cells of the nervous system requires further investigation (Holt et al., 1975, *Brit. Med. J.,* 7:1037–1038).

RV-directed polypeptide synthesis in normal rat glial cells in continuous tissue culture has been studied (Singh & Van Alstyne, 1978, *Brain Res.* 155:418–421). Unlike a productive rubella virus infection in permissive murine L (muscle) cells, infection of normal glial cells resulted in no detectable progeny virons in tissue culture supernatants and no detectable rubella 33 Kd core protein in infected cell lysates (Pope and Van Alstyne, 1981, *Virology* 124:173–180). Furthermore, exposure of infected gila to dibutyryl cyclic adenine monophosphate reversed the restriction, resulting in the appearance of the 33 Kd rubella nucleocapsid protein in infected cell lysates and the appearance of mature progeny virions in tissue culture supernatants (Van Alstyne and Paty, 1983, *Virology* 124:173–180).

Others have reported a lack of synthesis of the structural M protein in measles virus-infected brain cells obtained from subacute sclerosing panencephalitis autopsy material established in tissue culture (Hall and Choppin, 1979, *Virology* 99:443–447). Also, it is known that the incomplete synthesis of some Herpes specific structural proteins occurs during a nonpermissive infection of some cells of nervous system origin (Adler et al., 1978, *J. Gen. Virology* 39:9–20).

Taken together, these data indicate that even very different viruses may undergo restricted replication in brain cells. The synthesis of a limited number of viral gene products could account for incomplete virion assembly, the translation of polypeptides of variable molecular weights, alterations in the immune response to input virus, and difficulties in successful virus isolation from infected brain tissue.

Therefore, there remains a need for a diagnostic system which would detect RV protein antigens in CNS tissue in both the presence as well as the absence of an active, productive infection.

Early diagnostic tests were based on the hemagglutinating properties of its external glycoproteins. Commonly, the hemagglutination inhibition assays relied on the presence of antibodies to the RV hemagglutinin (HA) in the serum samples to inhibit the vital-mediated hemagglutination of chick red blood cells (Herrmann, "Rubella Virus", 1979, in *Diagnostic Procedures For Vital, Rickettsial And Chlamydial Infections*:725–766). The presence of high inhibition, indicated the indirect measurement of antibodies to the HA protein, and thereby, a recent rubella infection.

More recent tests employ enzyme-labelled antibodies in the enzyme-linked-immunosorbent assays (ELISA) (Voller & Bidwell, 1975, *Br. J. Exp. Pathol.* 56:338–339 incorporated herein by reference). These assays are also indirect tests to measure the amount of circulating antibody to RV as an indication of infection. Indirect ELISA tests for RV employ bound viral antigens on a plastic microwells and the presence of bound antibodies linked to enzymes such as horseradish peroxidase.

There are several problems with the use of the indirect RV ELISA kits. These relate to low antibody titers observed with RV infection, the need for elaborate "cut-off" value calculations to eliminate background binding, the limited use of the test in the detection of low levels of specific viral antigens present in chronic CNS infection, and the tedious and time consuming nature of the test performance.

A different use of monoclonal antibodies and their corresponding synthetic peptide epitopes may prove more useful in detecting RV infection in the CNS. There has been discussion that refers to the use of three non-competing monoclonal antibodies directed against the E1 glycoprotein, but this system has not been applied to CNS-specific diagnostics (Terry et al., 1988, *Arch. Virol.* 98, 189–197 incorporated herein by reference).

Therefore, there is clearly a need for a rapid and a sensitive diagnostic test for the detection of the RV in CNS infection.

Furthermore, a live, attenuated rubella vaccine has been developed (Parkman et al., 1966, *N. Engl. J. Med* 275: 569–574). This vaccine is immunogenic in at least 95% of the recipients, and does confer protection against reinfection, in spite of the fact that it induces antibody levels which are significantly lower than those generated by wild type virus infection. However, a serious drawback associated with the administration of the attenuated vaccine is the significant proportion of adult females that go on to develop rubella-associated arthritis. Furthermore, recently immunized individuals still harbour infectious virus and are therefore infectious, proving dangerous to pregnant women with whom they may be in contact.

Therefore, there is also a need for a non-infectious, innocuous vaccine. Such a vaccine could possibly be constructed from synthetic or recombinant peptides of RV proteins. Moreover, no epitope has yet been identified which would induce only neutralizing antibodies, necessary for conferring effective vaccine protection.

Another virus responsible for meningitis is the Human Immunodeficiency Virus-1 (HIV-1). HIV-1 is a human retrovirus which has been identified as the etiological agent of AIDS, an infectious and fatal disease transmitted through intimate sexual contact and exposure to contaminated blood or blood products. HIV-1 is related to the lentiviruses on the basis of its biological and in vitro characteristics, morphology and nucleotide sequences. It is also referred to as Human T-cell Lymphotrophic Virus type III, Lymphadenopathy Associated Virus, and AIDS Associated Retrovirus (Gallo, et al., 1984, *Science*, 224:500–503; Sarngadharan, et al., 1984, *Science*, 224:506–508; Barre-Sinoussi, et al., 1983, *Science*, 220:868–871; Levy, 1984, *Science*, 225:840–842; Gonda et al., 1985 *Science*, 227:177–179; Stephan, et al., 1986, *Science*, 231:589–594). Much interest has been focused on the effect of the long term, persistent infection of the immune system, by HIV-1. Recent information indicates that the virus moves from blood to the lymph nodes and thymus where it remains active, culminating in viremia, a precipitous drop in the CD4+T-cell count, and one or more of the several symptoms known as AIDS.

However, primary HIV-1 infection itself results in an immediate set of defined clinical features. Commonly, an acute febrile illness resembling influenza or mononucleosis is noted. In addition, lymphocytic meningitis may accompany the febrile illness and the patient may then be presented with headache, stiff neck and photophobia, as well as rigors, arthralgias and myalgias, truncal maculepapular rash, urticaria, abdominal cramps and diarrhea (Ho, 1985, *Ann. Internal Medicine* 103:880–883).

While some patients remain asymptomatic for up to 3 months preceding their seroconversion, indicating that HIV-1 infection may be subclinical, primary infection should be included in the differential diagnosis of prolonged febrile illnesses in persons at risk for AIDS. The presence of a maculopapular or urticarial rash, or lymphocytic meningitis is compatible with this diagnosis. Hence, early recognition of the varied syndromes associated with this virus might permit effective treatment before immunologic abnormalities become established.

There is, therefore, the need for a rapid, direct diagnostic test for viral meningitis, prior to seroconversion, when the transient meningitis may represent the initiation of a more serious, long term HIV-1 related illness.

Currently, one of the most commonly used direct tests for HIV-1 infection employs the following approaches: (i) direct culturing of virus from infected blood or blood cells and subsequent in vitro propagation of the virus in lymphocyte cultures; (ii) measuring reverse transcriptase levels; (iii) immunocytochemical staining of viral proteins; (iv) electron microscopy; (v) hybridization of nucleic acid probes; and measuring HIV-1 antigens with enzyme immunoassays (Goudsmit et al., 1986, *Brit. Med. J.,* 2993:1459–1462; Caruso et al., 1987, *J. Virol. Methods,* 17:199–210).

The HIV-1 appears to have at least three core protein (p17, p24, and p15) that are derived from a core polyprotein called gag polyprotein. See Muesing, et al., 1985, *Nature* 313:450–458 incorporated herein by reference. The gag polyprotein in the LV isolate of HIV-1 is 478 amino acids long and the three mature core proteins appear to be derived as p17 from amino acid sequence numbers 1–132, p24 from amino acid sequence numbers 133–391, and p15 from amino acid sequence numbers 392–478 (Muesing, infra). Moreover, it appears that the HIV-1 (LAV-la isolate) also has at least one capsid transmembrane glycoprotein derived from a 861 amino acid long Envelope Polyprotein (Wain-Hobson, et al., 1985, *Cell* 40:9–17 incorporated herein by reference).

The enzyme immunoassays have clearly shown the diagnostic importance of the presence of the p24 core protein. A correlation has been established between viremia, the decline of antibodies to p24, and the progression of symptoms from the asymptomatic seropositivity to fully expressed AIDS (Lange et al., 1986, *Brit. Med. J.,* 293:1459–1462; Paul et al., 1987, *J. Med. Virol.,* 22:357–363; Forster et al., 1987, *AIDS,* 1:235–240). A decline in the p24 core level has also been observed to occur in patients treated with AZT (Chaisson et al., 1986, *New Eng. J. Med.,* 315:1610–1611).

Assays for the direct detection of p24 are currently on the market (Allain, infra; Forster, infra). These assays use the same sandwich format in which serum samples are incubated with bound and enzyme-labelled anti-p24-antibodies to form an antibody/p24-antigen-antibody sandwich. Antigen levels of approximately 50 picograms/ml can be detected, when the antigen concentration is read from a standard curve constructed with a set of p24 standards of known concentrations. The tests are tedious and time consuming to perform, require dilutions of patients' sera, and do not provide information regarding the comparisons of rising antigen and concomitant declining antibody levels necessary to evaluate laboratory findings.

Therefore, the need to rapidly and effective diagnostic test to screen large numbers of a symptomatic individuals for the presence of HIV-1 virus in individuals is clear.

There is also an urgent need for a vaccine to afford protection against transmission of AIDS by individuals who are not detected by current diagnostic tests.

However, there are significant difficulties inherent in designing a vaccine which will confer protection against HIV-1. The vaccine must differentiate between HIV-1 and the closely-related virus, HIV-2. The rapid rate of HIV-1 mutation requires that the antigen(s) be highly conserved. Moreover, the HIV-1 infection of a small subset of T cells requires the killing of an integral part of the immune cell network, with unknown consequences, to completely eradicate the virus. In addition, vaccinated antigens could enter lymph nodes and stimulate B cells to produce cytokines that in turn stimulate HIV-1 infection of T cells, and thereby having a reverse effect, causing a more rapid onset of AIDS.

Peptides from gp120, gp160, gp41, gp120 +gp41, p17 and p14 are currently being employed for vaccine production by several companies and universities (Spalding, 1992, *Biotech.* 10:24–29.) However, these peptides are being tested for their ability to solely induce B cells to produce neutralizing antibody.

Therefore, there is an urgent need for the selection of HIV-1 peptides which would serve as appropriate B cell stimulators, to produce protective, neutralizing antibody, as well as appropriate cytokine blockers to prevent HIV-1 infection of T-cells. To date, no known combination of such peptides has been shown to protect against AIDS infection.

Bacteria are the other major cause of meningitis. Approximately 70% of all cases of bacterial meningitis occur in children under the age of 5 years; three bacterial species cause 84% of all meningitis cases reported in the United States: *Haemophilus influenza* type B, and *Streptococcus pneumoniae* and *Neisseria meningitidis* (Roos, infra; Stutman, infra). Less prevalent bacterial species include *Pseudomonas aerugensosa,* Staphylococci, Mycobacteria and Listeria species.

All strains of *Haemophilus influenzae* (*H. influenza*) are divided into two groups: typeable strains which commonly have a capsule, and nontypeable strains which do not. Typing of the encapsulated strains is accomplished by serological techniques, using reference antisera. Types a to f have been identified in this way. Those strains which fail to react with any of the reference antisera are classified as nontypeable.

The most frequent cause of neonatal meningitis and other invasive infections in the United States is the encapsulated *H. influenzae* type b (Hib) (Fraser et al., 1974, *Am. J. Epidemiol,.* 100:29–34). While the major incidence of childhood meningitis occurs between the ages of one and five years, 60% of the meningitis cases due to Hib occur in children under the age of two years.

The nontypeable *H. influenzae* are known to cause meningitis, pneumonia, bacteraemia, postpartum sepsis, and acute febrile tracheobronchitis in adults (Murphy et al., 1985, *J. Infect. Diseases,* 152:1300–1307). About 20 to 40% of all cases of otitis media are caused by this *H. influenzae,* which is a frequent etiologic agent of otitis media in children and young adults. Since infection confers no long lasting immunity, repeated infections of the same organism is frequently observed. These chronic ototis media infections are treated by administration of antibiotics, and drainage of the inner ear, where such a procedure is deemed necessary. *H. influenzae* strains have also been implicated as a primary cause of sinusitis (Cherry & Dudley, 1981, in Feigin & Cherry eds., *Textbook of Pediatric Infectious Diseases:*103–105). Nontypeable *H. influenzae* are also known to cause neonatal sepsis.

A vaccine is currently available for protection against typeable *influenzae*, and employs the capsular polysaccharide antigen of Hib, polyribosyl ribitol phosphate (Smith et al., 1973, *Pediatrics,* 52:637–644; Anderson et al., 1972, *J. Clin. Inv.,* 51:31–88). However, Anti-PRP antibody is not effective in conferring protection against non-typeable *H. influenzae* infection. Thus, all available vaccines against *H. influenzae* are all directed against Hib, and all elicit anti-PRP antibody to confer protection. Since the non-typeable *H. influenzae* lack the PRP capsule, no vaccine is efficacious against this group.

However, there does appears that *H. Influenzae* exhibits an outer membrane lipoprotein referred to as p4 (Green, et al., 1992, EMBL Bank, incorporated herein by reference).

The p4 protein appears to be derived from the Lipoprotein E Precursor, the precursor protein being 274 amino acids in length. (SEQ ID NO: 17)

There is therefore a clear need for both a method of diagnosis for this disease as well as a vaccine which would protect against both typeable as well as nontypeable *H. influenzae*. It is possible that the p4 lipoprotein providing a source for such a vaccine.

Streptococcus pneumoniae is the leading cause of community-acquired bacterial pneumonia (pneumococcal diseases), with approximately 500,000 cases a year reported in the United States. Bacterial pneumonia is most prevalent among the very young, the elderly and immuno-compromised persons. In infants and children, pneumococci are the most common bacterial cause of pneumonia, otitis media and bacteraemia and a less common cause of meningitis (causing 20–25% of reported cases).

Pneumococci are carried in the respiratory tract of a significant number of healthy individuals. But, in spite of the high carriage rate, its presence does not necessarily imply infection. However, if one of the highly pathogenic pneumococcal types, such as *S. pneumoniae*, is isolated from rusty-colored sputum (also containing a large number of polymorphonuclear leucocytes), body fluids, blood cultures, or specimens collected via transtracheal or lung puncture from the lower respiratory tract, its detection is usually significant.

*S. pneumoniae* is a gram positive bacteria. Proteins located on the cell surface of many gram positive bacteria are frequently involved in virulence and host immunity and have, in the past, been used in typing these bacteria and in immunoprotection studies. There are a large number of *S. pneumoniae* strains, classified into serotypes based on their surface carbohydrate structures. There are also many cell surface proteins associated with *S. pneumoniae*. Surface proteins that exhibit antigenic variation (by antigenic shirt or drift) make the identification of a common but exclusive cell surface antigen difficult and may provide the organism with an additional mechanism for evading the host immune response.

Detection of this bacteria at an early stage is essential to facilitate treatment of the infection. Thus, it is important to be able to quickly identify whether *S. pneumoniae* is present in a patient and to be able to follow the effect of antibiotic treatment on the bacteria. As available immunoassays for *S. pneumoniae* antigen detection are deficient for lack of specificity and/or sensitivity, there remains the need for an improved method of such detection.

Monoclonal antibody (Mab) technology has recently provided researchers with tools to reproducibly and accurately analyze the cell surface components of *S. pneumoniae*. Hence *S. pneumoniae* proteins are of interest to epidemiologists as they may provide a method of detection as well as for vaccines against the bacteria.

One such cell surface protein is *Streptococcus pneumoniae* pneumonococcal surface protein A (pspA) (Yother, 1992, J. Bacteriol. 174:601–609 incorporated herein by reference). The complete sequence of this protein is known.

It is known that one such pneumonococcal vaccine has been developed which incorporates the capsular polysaccharide antigens of 23 prevalent serotypes of pneumococci. These serotypes are responsible for 87% of pneumococcal disease in the United States. This second generation vaccine replaced a 14-valent polysaccharide vaccine available since 1977. However, the U.S. Department of Health and Human Services has stated that a more immunogenic pneumococcal vaccine is needed, particularly for children younger than 2 years of age. This necessity exists because the 23-valent vaccine is poorly immunogenic in this age group. Consequently, the use of the vaccine is not recommended in children with recurrent upper respiratory diseases, such as otitis media and sinusitis. Furthermore, the 23-valent vaccine is only 44–61% efficacious when administered to persons over 65 years old, and revaccination is not advised. Thus, there remains a clear need for an improved pneumococcal vaccine.

*Neisseria meningitis* (*N. Meningitis*) is one of the leading causes of community-acquired bacterial meningitis, causing 10.3% of cases in the United States between 1978–1981 (Tunkel et al., 1990 *Annals of Internal Medicine*, 112: 610–623). Meningococcal meningitis is most prevalent among infants between 6–12 months and adolescents (Larter & Master, 1992, *Am. J. Med.—Infectious Disease Symposium:*120–123). In addition to meningococemia, other less commonly associated diseases such as conjunctivitis, sinusitis, endocarditis, and primary pneumonia can occur (Duerden, 1988, *J. Med. Microbiol.*, 26:161–187).

*N. meningitidis* bacterium are carried in the nasopharynx of 10–15% of healthy individuals. In spite of the high carriage rate, its presence does not necessarily imply infection. However, isolation of *N. meningitidis* from cerebral spinal fluid or blood culture is significant (Stutman, infra; Mendelson & Dascal, 1992, *Can. J. of Diag.*, 9:47–57; Martin, 1983, *Am. J. Med.:*120–123).

*N. meningitidis* is a gram negative bacteria. Proteins located on the cell surface of many gram negative bacteria have, in the past, been used in typing and immunoprotective studies. There are a large number of *N. meningtidis* strains and there are many cell surface proteins associated with *N. meningtidis*. This has made identification of a common but exclusive cell surface antigen difficult.

Detection of this bacteria at an early stage is essential to facilitate treatment of the infection (Stutman, infra). Thus, it is important to possess the ability to identify whether *N. meningtidis* is present in a patient and to follow the effect of antibiotic treatment on the bacteria. As available immunoassays for *N. meningtidis* antigen detection have shown lack of specificity and/or sensitivity, there remains the need for an improved method of such detection.

As Mab technology has recently provided researchers with tools to accurately analyze the cell surface components of this bacteria, *N. meningtidis* proteins are of interest to the epidemiologists as they may provide for a new method of detection as well as a vaccines against it.

One such cell surface protein is the Opacity-Related Protein POPM3 (Stern, 1987, *Mol. Microbiol.* 1:5–12 incorporated herein by reference). The complete sequence of this 170 amino acid protein is known.

Most meningococcal vaccines have been developed using capsular polysaccharides. One particularly quadravalent vaccine incorporates polyssacharide antigens of serogroups A, C, W and Y, meningococci. However, these serogroups are responsible for less than 49% of memingococcal disease in the United States. No capsular polyssacharide vaccine is available for serogroup B *N. meningtidis*, which is the most prevalent serogroup, since it is poorly immunogenic. Moreover, polyssacharide vaccines are poorly immunogenic in infants because they are T lymphocyte independent antigens which are inefficient at inducing an immunologic memory. Furthermore, no cross protection between serogroups occurs. Thus, there remains the need for an improved meningococcal vaccine.

It follow then, that there remains a need for at least two products relating to *N. meningtidis*. The first being a rapid, specific, and sensitive diagnostic test for all strains of *N. meningtidis*, that does not give false positive results. What is optimally desired is a Mab that will recognize a cell surface antigen that is universally present in most, if not all, strains of *N. meningitidis*, and, at the same time does not recognize other non-meningitidis causing organisms or material which may be found in conjunction with *N. meningitidis*. Secondly, it is desirous that the Mab and said protein be used in research towards development of an improved vaccine.

In addition the three major causes of bacterial meningitis, there are other bacterial agents responsible for the disease. One such agent is *L. monocytogenes*, a motile, grampositive, rod-shaped microorganism belonging to the genus Listeria. This genus is widely distributed in nature-found in soil, water, vegetation and many animal species. See Bille & Doyle, 1990, "Listeria and Erysipelothrix" in Burbert, et al., *Manual of Clinical Microbiology* 5th ed.:231 which is incorporated herein by reference. Two Listeria species, *L. murrayi* and *L. grayi*, are rarely isolated and are presently considered nonpathogenic. However, five other species are genomically related and include three hemolytic species (*L. monocytogenes, L. seeligeri* and *L. ivanovii*) and two non-hemolytic species (*L. innocua*, and *L. welshimeri*). Of these, only *L. monocytogenes*, and sometimes *L. ivanovii* are human pathogens. *L. ivanovii* is mostly pathogenic for animals (Bille, infra).

*Listeria monocytogenes* is a facultative intracellular pathogen, capable of growth both in the external environment and inside mammalian cells. It is responsible for opportunistic infections in both humans and animals. The first cases of human listeriosis were reported in the 1930s and outbreaks have been traced to the consumption of contaminated food, most notably dairy and poultry products (Goebel et al., 1991, *Infection* 19:5195–5197). Individuals at risk are the newborn, the elderly, and the immunocompromised.

Clinical features of the diseases are meningitis and meningoencephalitis. Infection with *L. monocytogenes* has also been observed as septicemia (with resulting abortion) in pregnant women, and patients with malignancies and immunosuppression. Some people, usually predisposed by an underlying cardiac illness, have been treated for endocarditis resulting from listerial infection.

Although *L. monocytogenes* is considered an uncommon adult pathogen, it is the third most common cause of bacterial meningitis in neonares (McKay & Lu, 1991, *Infection & Immun.* 59:4286–4290). Highest mortality and neurological sequelae among survivors is seen when the central nervous system is involved. However, underlying conditions which cause lower cell-mediated immunity, such as transplants, malignancy and AIDS, can result in increased mortality, up to 60%.

There has been a gradual increase in the incidence of human Listeriosis since the 1960s. Presumably, this is related to the increased numbers of individuals with malignancies undergoing radiation and chemotherapy, which allows for their prolonged survival but with immunosuppression as their consequence. Similarly, increases in renal transplantations has exposed increasing numbers of patients to possible infectious complications. Finally, with the rapid spread of AIDS and its suppression of immune function, it can be expected that the occurrence of human listeriosis may increase substantially in the future years.

The epithelial cells of the gastrointestinal tract may be the primary site of entry of *L. monocytogenes*. It was discovered in the 1960s that this bacterium can invade, survive and replicate within phagocytic cells, such as macrophages and monocytes (Michel & Cossart, 1992, *J. Bacteriol.* 174:7098–7103 incorporated herein by reference). Nonprofessional phagocytes, which are unable to take up extracellularly growing bacteria, are also susceptible to invasion by this intracellular organism (Bubert et al., 1992, *J. Bacteriol.* 174:8166–8171 incorporated herein by reference). Apparently, *L. monocytogenes* is able to induce its own phagocytosis in these host cells. Specific virulence factors are required for this invasion and intracellular growth.

A major extracellular protein P60, named for its relative molecular weight of 60,000 daltons, is produced by all virulent L. monocytogenes strains. Protein P60 is derived from the Protein P60 Precursor also known as the invasion-associated protein (iap) as described by Koehler, et al., 1990, *Infect. Immun.* 58:1943–1950 incorporated herein by reference. Moreover, the precursor protein is 484 amino acids in length and the sequence is known.(SEQ ID NO: 26)

Spontaneously occurring mutants of *L. monocytogenes* that show a decreased level of the protein P60, known as R mutants, are a virulent and unable to invade nonprofessional phagocytes. R mutants are still phagocytized by macrophages with the same efficiency as wild-type bacteria and are able to replicate in these cells. Addition of partially purified P60 protein from wild-type *L. monocytogenes* restores the invasiveness of these R mutants into nonprofessional phagocytic cells. This finding has led to the conclusion that P60 is involved in the mechanism of uptake of *L. monocytogenes* by nonprofessional phagocytic cells.

The P60 protein of *L. monocytogenes*,(SEQ ID NO: 26)is 484 amino acids long, contains a putative N-terminal, signal sequence of 27 amino acids and an extended repeat region of 19 threonine-asparagine units. The middle portion of the protein P60, consisting of about 240 amino acids, and located about 120 amino acids from both the N-and C-terminal ends, varies considerably from the deduced amino acid sequences of the related P60 proteins of *L. innocua, L ivanovii, L seeligeri, L welshimeri* and *L grayi*. From the predicted secondary structure and hydropathy studies on this protein, the hydrophillic middle portion consists of two alpha-helical regions flanking the repeat domain. Conversely, the hydrophobic N- and C- terminal ends are in predominantly B-pleated sheets. This would suggest that the middle region is exposed on the protein's surface (Kohler, infra).

The CSF findings in *listeria meningitis* are quite variable and often result in a negative gram stain. This means that confirmed diagnosis is dependent on culture of either blood or CSF samples, which may take up to 48 hours. Given its high mortality and morbidity, and the increasing numbers of populations at risk, it is apparent that the need exists for rapid diagnosis and for a vaccine against *L. monocytogenes* infections.

It is a well known feature of bacterial and viral meningitis etiological agents that they possess the ability to infect the CNS. Until recently, it was not known how these agents could pass the Blood-Brain Barrier. The mechanism by which circulating bacteria enter the CSF compartment has only recently been understood. Circulating organisms could invade the CSF compartment by translocation through or between vascular endothelial cells and underlying tissues before entering the CSF. In fact, vascular lesions are a feature of meningitis caused by such organisms as *Salmonella choleraesuls* and *Pasteurella haeloytica*. See Wildock, 1977, Vet. Pathol 14:113–120; Sullivan, "The Nervous System: Inflammation", in Jubb et al., eds., 1985, *Pathology of Domestic Animals*, Volume 1:278–290 all of which are incorporated herein by reference.

However, while vascular endothelial damage may be integral to the pathogenic pathway for some bacteria, it is unlikely to be the mechanism of entry for most cases of meningitis, since vascular lesions are not a prominent early feature of meningitis caused by either *N. meningtidis, S. pneumoniae, E coli, S. suls, H. parasuis, H. influenzae,* or *S. aureus* (Williams, 1990, *J. Infec. Dis.*, 162:474–481).

It has been shown that bacteria can be carried into the CSF in association with monocytes migrating into the CSF compartment to maintain populations of resident macrophages (Cordy, 1984, *Vet. Pathol* 21:593–597). This method of entry for bacteria is also analogous to the mechanism employed by some viruses (HIV, Maaedi-Visna-caprine arthritis encephalitis virus) when invading the CNS. See Peluso, 1985, *Virology* 147:231–236; Narayan, 1985, *Rev. Infec. Dis.* 7:899–98; Roy, 1988, *J. Leukoc. Clol.* 43:91–97; Westervelt, 1991, *Vaccines* 91:71–76 which are all incorporated herein by reference.

It is also known art that cellular immune reactions consist of a complex series of coordinating events. In response to tissue injury, monocytes are recruited from bone marrow via the blood circulation (Robinson, 1989, *PNAS* 86:1850–1854 incorporated herein by reference). These activated blood monocytes then differentiate into macrophages in response to several immune mediators produced at the site of inflammation (Yoshimura, et al., 1989, *FEBS Letter* 244:487–493).

As macrophages normally function to protect the body from potentially toxic substances, either infectious or chemical in nature, they serve as scavengers, processing and presenting antigen to the B lymphocytes, which in turn produce antibodies. (Edington, 1993, *Bio/Technology* 11:676–681 incorporated herein by reference), Macrophages and also known to secrete mediators that mediate systemic host defence responses and local inflammation.

The first evidence of mediators being involved in cellular immune reactions was noted in 1970 (Ward, 1970, *Cell Immunol.*, 1:162–174). It was reported that addition of antigen to specifically sensitized lymphocytes caused release of an "activity" which attracted macrophages (Robinson, infra). It is now well known that immune mediators possess a variety of functions for cytokines such as the interleukins and interferons.

This led the recent discovery of a family of small, secretory cytokine-like proteins called chemokines for their apparent chemotactic properties, whose complete proinflammatory functions have yet to be elucidated. However, the size and amino acid sequence of many of these chemokines is known as illustrated in Michiel, 1993, *Bio/Technology* 11:739, incorporated herein in its entirety by reference.

Like most secreted proteins, the chemokines are synthesized with a hydrophobic leader sequence which is cleaved to produce the mature, active chemokine. Comparison of their amino acid sequences has shown these proteins to have a highly conserved pattern of four cysteine residues in the mature peptides. Consequently, they have been classified into two groups based on their structural characteristics: the alpha chemokine group having an intervening amino acids between cys-1 and cys-2, (ie. a C-X-C motif); the beta chemokine group has no intervening amino acid, (ie. a C-C motif). (Michiel, 1993). Cys-1 crosslinks with Cys-3 and Cys-2 crosslinks with Cys-4, resulting in a similar tertiary structure for all the proteins classified into this family of chemokines.

It is further known that the chemokines appear to be functionally involved in cell chemotaxis. Their amino acids sequence diversity suggests that each chemokine has distinct cellular specificity, each having its own unique cellular targets.(Michiel, infra). This cellular specificity appears related to seven transmembrane-domain receptors in each chemokine, but the overlapping pattern of ligand binding and their regulation has yet to be determined (Rollins, et al., 1989, *Molecular & Cellular Biol.* 9:4687–4695 incorporated herein by reference).

Several peptides from the beta chemokine family have been found to possess the ability for "chemo-attracting" monocytes/macrophages. One such chemotactic protein was identified in 1978 in antigen-stimulated human lymphocytes. (Robinson, infra) and was named LDCF, for Lymphocyte-Derived Chemotactic Factor. This particular chemokine has since been isolated from a variety of different glioma cell lines; human peripheral blood mononuclear leukocytes, (Yoshimura, infra); resting human monocytes (Rollins, infra); human lung fibroblasts and a primary human fetal fibroblast cell line. This latter line being the only member of the Beta family of chemokines to be identified in fibroblasts.

As with all chemokines, various names have been used to identify this protein. The following terms are therefore interchangeable for those skilled in the art: GDCF-2: for Glioma-Derived Monocyte Chemotactic Factor; hJE: for human JE gene product; MCAF: for Monocyte Chemotactic Factor; and MCP: for Monocyte Chemoattractant Protein-1. As the amino acid sequences for these chemokines was found to be identical, the term MCP has been adopted for describing this particular chemokine. It is thus referred to in the art as other chemokines that share significant sequence homology with MCP-1, and have been named MCP-2and MCP-3, according to the order of their discovery.

The amino acid sequence of MCP-1 shows the mature protein to be 99 amino acids long starting at what corresponds to nucleotide 70 of the gene. The functional portion of the protein is known to be the active portion with the first 23 amino acids serving as a signal sequence. MCP-1 is a secretory N-glycosylated glycoprotein of a variety of molecular weights but predominantly occurring at 13,000; 15,000; and 15,500 Daltons with post-translational modification probably accounting for the various forms. The two former isoforms have been named alpha and beta respectively but the structural differences between the two are still unknown. Yet, it is known that their amino acids sequences are identical, apparently derived from a single gene product.

Many mitogenic and activating stimuli appear to cause secretion of MCP-1 by a wide variety of cells. These findings suggest that the cellular regulation of MCP-1 expression is complex, and involves circulating cytokine levels in addition to other factors. Viral and bacterial infections in turn, can affect these levels and are thus involved in the function of MCP-1.

The size and amino acid sequence of MCP-3 is also known as illustrated by Van Damme, et al., 1992, *J. Exp. Med.* 176:59–65, incorporated herein by reference. It has also been determined that MCP-3 is a chemotactic factor that can attract monocytes and that it can bind heparin.

Amino acids sequences of all proteins described in detail in the present invention are given using the following single letter code: A=ala, C=cys, D=asp, E=glu, F=phe, G=gly, H=his, I=ile, K=lys, L=leu, M=met, N=asn, P=pro, Q=gln, Rh=arg, S=ser, T=thr, V=val, W=trp, Y=tyr.

Accordingly, there remains a significant and urgent need to determine the mechanism used by meningitis etiological agents, as diverse as bacteria and viruses, to attract and infect monocytes and/or gaining access to the CNS. There also remains a significant and urgent need to develop a therapeutic capable of blocking such infection of the CNS by bacterial and viral meningitis etiologic agents utilizing such a mechanism. Specifically, there remains a need in the art for a monoclonal antibody specific for both bacterial and viral infectious agents of meningitis, where said monoclonal antibodies would recognize both bacterial and viral infectious agents of meningitis and have substantial diagnostic utility. Additionally, there is also a need for a known proteinaceous region containing the epitope(s) recognized by said monoclonal antibody where said epitope or peptide could be chemically synthesized, thereby avoiding the difficulties inherent in purification and administration of larger fragments of the antigenic molecules. An additional need for this said peptide is evident for use in diagnostic test kits to indicate meningitis infection as well as would also be useful in the development of a general meningitis vaccine.

BRIEF DESCRIPTION OF THE DRAWINGS

FIG. 1 depicts the amino acid sequence of (SEQ ID NO:1) the Structural Polyprotein protein of the M22 strain of Rubella virus with sequences of interest underlined.

Figure 2:
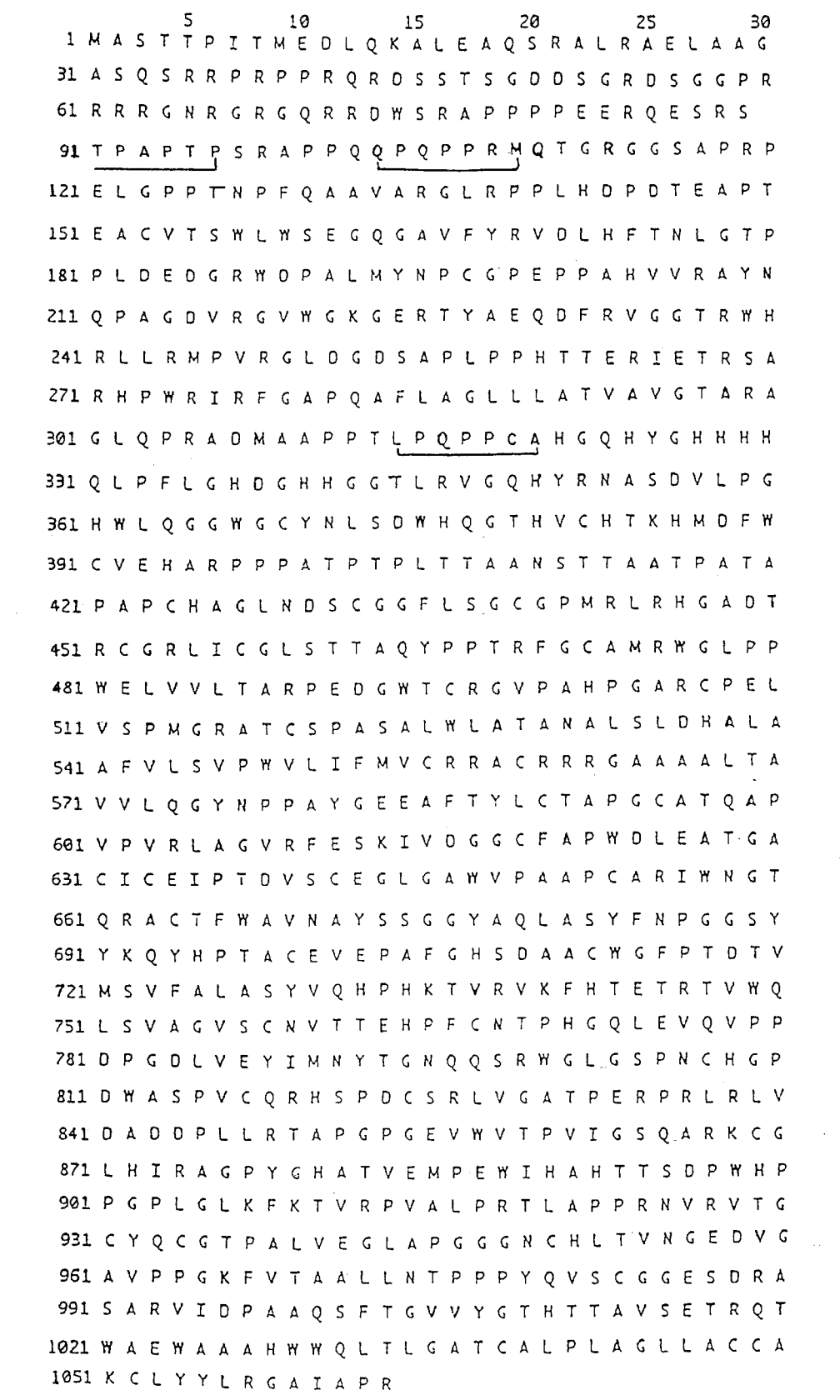

FIG. 2 depicts the amino acid sequence (SEQ ID NO: 8) of the Structural Polyprotein of the Therien strain of Rubella virus with sequences of interest underlined.

FIG. 3 depicts the amino acid sequence (SEQ ID NO: 11) of the Gag Polyprotein of the LV isolate of HIV-1 with sequences of interest underlined.

FIG. 4 depicts the amino acid sequence (SEQ ID NO: 14) of the Envelope Polyprotein Precursor protein of the LV-la isolate of HIV-1 with sequences of interest underlined.

FIG. 5 depicts the amino acid sequence (SEQ ID NO: 17) of the Lipoprotein E Precursor of Haemophilus influenzae with sequences of interest underlined.

FIG. 6 depicts the amino acid sequence (SEQ ID NO: 20) of the Opacity-Related Protein of *Neisseria meningitidis* with sequences of interest underlined.

FIG. 7 depicts the amino acid sequence (SEQ ID NO: 23) of the Pneumococcal Surface Protein A of *Streptococcus pneumoniae* with sequences of interest underlined.

FIG. 8 depicts the amino acid sequence (SEQ ID NO: 26) of Protein P60 Precursor of *Listeria monocytogenes* with sequences of interest underlined.

FIG. 9 depicts the amino acid sequence (SEQ ID NO: 35) of the chemokine hMCP-1 with sequences of interest underlined.

FIG. 10 depicts the amino acid sequence (SEQ ID NO: 38) of the chemokine HMCP-3 with sequences of interest underlined.

FIG. 11, Immunoblots of RV antigens reacted with Mab's RV1, RV2, RV3 and RV4. RV antigen: Strain MPV-77 (lot #50678, Catalogue #EL-05-04) cultured in Vero cells. Purchased from Microbix Biosystems Inc., Toronto, Ontario). All Mab used as tissue culture fluid diluted 1/500. Lane 1 - Molecular weight markers of 97, 66, 45, 31, 21, and 14kD. Lane 2/3 - RV4; lane 4/5/6 - RV3; lane 7/8 - RV2; lane 9/10 - RV1. Lanes 2–9 all illustrate two proteins, 31 kD (major) and 45 kD (minor), identified by reactions with Mab's 1–4.

FIG. 12, Immunoblots of bacterial antigens reacted with V Mab RV1. *H. Influenzae* b antigen from ATCC (#10211); *L. monocytogenes* from ATCC (#7644); *S. pneumoniae* from the Caribbean Regional Epidemiology Centre, CAREC, Trinidad; *N. meningitidis* A from ATCC (#13077).

Lane 1-Molecular weight markers of 97, 66, 45, 31, 21, and 14 kD. Lane 2-*H. Influenzae* b-proteins of approximate weights of 50, 45, 40, and 25 kD. Lane 3-*L. monocytogenes*-proteins of approximate weights of 60 kD (major) and 66 kD (minor), Lane 4/5 -*S. pneumoniae*-proteins of approximate weights of 60 kD and 66 kD, Lane 6/7 -*N. meningitidis*-a protein of approximate weights of 18 kD, identified by reaction with Mab RV1.

FIG. 13, Immunoblots of HIV1 antigens reacted with RV Mab RV1. HTLV-IIIB viral lysate, lot #54.–040, purchased from Applied Biotechnologies, Inc., Md., USA. Lane 1 - Molecular weight markers of 97, 66, 45, 31, 21, and 14 kD. Lane 2 - Control RV antigens, 31 and 45 kD, reacting with RV1 Mab. Lane 3/4 - HIV1 antigen of approximate weights of proteins at 24 kD and 61 kD, identified by reaction with Mab RV1.

BRIEF DESCRIPTION OF THE INVENTION

The present invention provides novel peptides corresponding to homologous antigenic amino acid sequences on regions of bacterial and viral agents known to cause meningitis and on chemokines known to attract monocytes, in addition to monoclonal antibodies reactive with such antigenic regions and peptides. It also provides analogues of those peptides and mixtures and combinations of those peptides and analogues. These novel materials find use in, for example, a wide variety of diagnostic and preventive methods, means and compositions with respect to the overall process of pathogenesis which uses chemokine function to promote disease including meningitis, and atherosclerosis.

DETAILED DESCRIPTION OF THE INVENTION

The present invention provides novel compositions and methods for detecting, preventing and therapeutically treating disease wherein the pathogen or pathogenic mechanism includes a monoclonal antibody defined antigenic sequence. More specifically, using a monoclonal antibody defined by two rubella virus antigenic sites, a family of homologous cross-reacting antigenic sequences were identified in proteins associated with meningitis etiologic agents. These cross reacting antigenic sequences were in turn found to be significantly homologous to the C-terminal sequence of the monocyte attracting chemokines hMCP-1 and hMCP-3. Hence, this invention involves the use of peptides that mimick these homologous cross-reacting antigenic sequences and monoclonal antibodies reactive with such amino acid sequences to diagnose, treat and vaccinate against diseases wherein the pathogenic mechanism involves one or more members of these homologous cross-reacting sequences. An example of such a disease is meningitis.

A monoclonal antibody was used to identify two cross-reacting septapeptide antigens (QPQPPRM and PPQPPRA SEQ ID NO: 3 and 7 Respective) contained in the Structural Polyprotein (Core and E2 outer membrane proteins portion described in greater detail below) of Rubella virus. The monoclonal antibody, RV1-Mab, was also found to cross-react with the p24 core protein and the p61 outer membrane protein of Human Immunodeficiency Virus-1 (HIV-1), known to cause meningitis during the initial stages of infection. Furthermore, the RV1-Mab was also found to cross react with proteins found in *Hemophilus influenzae,*

*Neisseria meningitidis, Streptococcus pneumoniae* and *Listeria monocytogenes*, which together account for more than 85% of all bacterial meningitis in the United States. In this way, a family of homologous cross-reacting septapeptide antigens were discovered in viruses and bacteria known to cause meningitis. Because the RV1-Mab binds to amino acid sequences in diverse bacteria and viruses that are related only in the fact that they cause meningitis, these closely related homologous sequences have been designated Meningitis Related Homologous Antigenic Sequence (MRHAS).

A member of the MRHAS family can be defined as an amino acid sequence that is homologous to antigenic sites on the Structural Polypeptide (within the core and E2 membrane protein portion) of Rubella virus that are recognized by a Mab from the hybridoma RV-1. More specifically, any amino acid sequence, that is homologous to the regions extending from approximately amino acid residue 102 to 108 of the Structural Polyprotein (core protein region) and from about 313 to 319 of the Structural Polyprotein (E2 membrane protein) of the M33 strain of Rubella virus is by definition a member of the MRHAS family of sequences. The complete sequence of this Structural Polyprotein is found in FIG. 1 (SEQ ID NO: 1)Representative members that are cross-reactive with the RV1-Mab and appear in bacteria and viruses known to cause meningitis are presented in Table 1. The sequences of the proteins listed in Table 1 are found in FIGS. 1–8 and in SEQ ID Nos. 3, 5, 7, 10, 13, 16, 19, 22, 25, 28, 30, 32, and 34.

TABLE 1

| NAME | VIRUS/ BACTERIUM | PROTEIN | SEQUENCE |
| --- | --- | --- | --- |
| MRHASRV-1 | Rubella virus | Structural Polyprotein (Core) | QPQPPRM |
| MRHASRV-2 | Rubella virus | Structural Polyprotein (Core) | QTPAPKP |
| MRHASRV-3 | Rubella virus | Structural Polyprotein (E2) | PPQPPRA |
| MRHASRV-4 | Rubella virus | Structural Polyprotein (E2) | LPQPPCA |
| MRHASHIV-1 | HIV1 | Gag Polyprotein | QAISPRT |
| MRHASHIV-2 | HIV1 | Envelope Polyprotein Precursor | QNQQEKN |
| MRHASHI-1 | *Hemophilus influenzas* | Lipoprotein E Precursor | QVQNNKP |
| MRHASNM-L | *Nisseria meningitidis* | Opacity-Related Protein POPM3 | IQPPKN |
| MRHASSP-1 | *Streptococcus pneumonias* | Pneumococcal Surface Protein A | QQQPPKA |
| MRHASLM-1 | *Listeria monacytogenes* | Protein P60 Precursor | PTQEVKK |
| MRHASLM-2 | *Listeria monocytogenes* | Protein P60 Precursor | TTPAPKV |
| MRHASLM-3 | *Listeria monocytogenes* | Protein P60 Precursor | NTATPKA |
| MRHASLM-4 | *Listeria monocytogenes* | Protein P60 Precursor | QQTAPKA |

It is noted that within the Structural Polyprotein of Rubella virus, there are three proteins that can be ultimately derived. Therefore, when a reference is made to either the Core protein portion or the E2 membrane-associated protein portion (from either the M33 or Therien strains), this reference denotes the portion of the Structural Polyprotein from which the final mature protein will be derived. A similar nomenclature with respect to precursor versus mature protein was also used in connection with the Gag Polyprotein of HIV-1, the Envelope Polyprotein Precursor of HIV-1, the Lipoprotein E Precursor, and the Protein P60 Precursor. For example the Protein P60 Precursor has, at a minimum, a 27 amino acid leader sequence that is removed during processing to mature protein.

Members of the MRHAS family were also found to appear in two variants of the chemokine, human Monocyte Chemoattractant Factor (hMCF). These two are hMCP-1 and hMCP-3, as indicated in Table 2. The sequences of the factors listed in Table 2 are found in FIGS. 9 and 10 SEQ ID NOS 35 and 38, respectively) and in SEQ ID NOS 37 and 40.

TABLE 2

| NAME | FACTOR | POSITION | SEQUENCE |
| --- | --- | --- | --- |
| MRHASMCP-1 | hMCP-1 | 70–76 | OTOTPKT |
| MRHASMCP-3 | hMCP-3 | 61–67 | KTQTPKL |

It is surprising that bacteria and viruses as diverse as *Hemophilus influenzae, Neisseria meningitidis, Streptococcus pneumonias, Listeria monocytogenes*, RV, and HIV-1 share a common feature, namely the placement of MRHAS, a highly conserved sequence, on the outer membrane. However, some of these etiological agents of meningitis do share specific features. For example, Williams and Blakemore have shown that bacteria can be carried into the CNS in association with monocytes migrating into the CSF compartment to maintain populations of resident macrophages (Cordy, 1984, *vet. Pathol.* 21:593–597). This method of entry for bacteria would be analogous to that by which some viruses (HIV, Maaedi-Visna-caprine arthritis encephalitis virus) invade the CNS (Peluso, et al., 1985, *Virology* 147:231–236; Narayan and Cork, 1985, *Rev. Infec. Dis.* 7:899; Roy and Wainberg, 1988, *J. Leukoc. Clol.* 43:91–97; Westervelt et al., 1991, *Vaccines* 91:71–76). Moreover, available information for HIV-1 indicates that significant alterations in proteins carrying the MRHAS alters virulence, or invasiveness of the organisms.

Since the MRHAS that appear on bacterial and viral organisms are significantly homologous to sequences found in monocyte attracting chemokines, it is apparent that these agents have incorporated these sequences into their proteins to attract monocytes to aid in infection.

The unexpected discovery of monoclonal antibody cross-reactivity over various viral and bacterial species known to cause meningitis provides novel means for therapeutic and prophylactic treatments of meningitis. Moreover, the utility of this invention is extended by the significant homology of these antigenic sites with amino acid sequences in monocyte attracting chemokines. These novel means may be applied to dieases as diverse as meningitis and atherosclerosis, wherein the pathogen or pathogenic mechanism includes one or more of these MRHAS.

More specifically, a hybridoma is used to produce cross-reacting monoclonal antibodies that bind MRHAS in vivo and in vitro. These antibodies are useful as a diagnostic tool to detect the presence of MRHAS. One such diagnostic use is to detect the presence of bacterial and viral agents of meningitis in biological samples. Such Mabs are also useful for treating a patient to prevent and/or treat infection due to a meningitis etiologic virus and/or bacteria. A bacterial and/or viral meningitis infection can also be detected using peptides mimicking MRHAS in a diagnostic test. In vivo, peptides mimicking MRHAS can also be used as a novel vaccine for meningitis, in addition to use as blocking agents (therapeutics) to prevent the accumulation of monocytes involved in CNS infection and diseases such as atherosclerosis.

In one aspect, the novel peptides, typically less than about 30 amino acids, contain seven or more contiguous amino acids forming epitopes substantially similar to epitopes located on viruses and/or bacteria known to cause meningitis and/or on chemokines known to attract monocytes. Of particular interest are the regions extending from about amino acid residue: 102 to 108 (SEQ ID NO: 3) (core protein portion), 89 to 95 (SEQ ID NO: 5)(core protein portion), and 313 to 319 (SEQ ID NO: 7)(52 membrane portion) of the Structural Polyprotein of the M33 strain of Rubella virus; from about 314 to 320 (SEQ ID NO: 13)(E2 membrane portion) of the Structural Polyprotein of the Therien strain of Rubella virus; from about 145 to 151 of the Gag Polyprotein of the LV isolate of HIV-1; from about 655 to 661 (SEQ ID NO: 16) of the Envelope Polyprotein Precursor of the LAV-la isolate of HIV-1; from about 99 to 105 )SEQ ID NO: 22) of the Lipoprotein E Precursor of *Haemophilus influenzae*; from about 1 to 5 of the Opacity-Related Protein POPM3 of *Neisseria meningitidis*; from about 423 to 429 (SEQ ID NO: 25) of the Pneumococcal Surface Protein A of *Streptococcus pneumoniae*; from about 151 to 157, (SEQ ID NO: 2) 181 to 187, (SEQ ID NO: 30) 249 to 255,(SEQ ID NO: 32) and 292 to 298 (SEQ ID NO: 34) of the Protein P60 Precursor of *Listeria monocytogenes*; from about 93 to 99 (SEQ ID NO: 37) of the chemokine hMCP-1; and from about 61 to 67 of the chemokine hMCP-3.

Those skilled in the art will appreciate that additional analogous regions ("homologs") from other infectious agents (viruses, bacteria, etc.) or chemokines may be identified based upon their sequence homology with members of the MRHAS family. In practice, such homologs may be identified by reference to the MRHAS ocurring in hMCP-1, QTQTPKT (SEQ ID NO: 37).

This method can be applied to other infectious agents (viruses, bacteria, etc.) or chemokines that are yet to be discovered. For example, as new viruses or bacteria are identified that use monocytes to infect various regions of the body such as the CNS, their protein amino acid sequences may be aligned with that of the MRHAS in hMCP-1 to obtain maximum homology. The methods by which the sequences are aligned are known to those skilled in the art. The amino acid sequence of an infectious agent not listed herein, which corresponds to members of the MRHAS family specifically disclosed herein can be synthesized and used in accordance with the invention.

It is not necessary to the present invention that the epitopes contained within such sequences be cross-reactive with antibodies to all infectious agents of meningitis, or all chemokines that attract monocytes. Peptides encompassing immunological eiptopes which distinguish between types of monocytes or between efficacity for a particular type of monocyte will find utility in identifying different pathogenic mechanisms of infection and disease. For example, such utility will include infectious agents that use different modes of infectivity to enter the CNS. These peptides may also be useful in combination with other peptides representing other members of the MRHAS family in therapeutic composition.

In accordance with another aspect of the present invention, a novel cell line capable of producing monoclonal antibodies and compositions comprising such antibodies is provided, which antibodies are capable of selectively recognizing members of the MRHAS family. These monoclonal antibodies may be used in a wide variety of ways including diagnosis and therapy, as well as to identify other cross-reactive antibodies. Peptides or polypeptides containing the epitope(s) with which they react may find separate uses as immunogens for vaccines, or as therapeutic agents.

Generation of Monoclonal Antibodies

Monoclonal antibodies were prepared by immortalizing the expression of nucleic acid sequences that encode for antibodies or binding fragments thereof specific for members of the MRHAS family. See Godding, 1980, "Antibody Production by Hybridomas", *J. Immunol. Meth.*, 39:285–308 which is incorporated herein by reference. In brief, spleen cells from an immunized vertebrate that illustrate the desired antibody response are immortalized. Immunization protocols are well established and though such protocols can be varied considerably, they still remain effective. Also see, Goding, 1986, *Monoclonal Antibodies: Principles and Practice*, Academic Press, 2nd edition, which is herein incorporated by reference. Cell lines that produce the antibodies are most commonly made by cell fusion between suitably drug-marked human or mouse myeloma or human lymphoblastoid cells with human B-lymphocytes to yield the hybrid cell lines. Other methods include Ebstein-Barr Virus transformation of lymphocytes, transformation with bare DNA (such as oncogenes or retroviruses), or any other method which provides for stable maintenance of the cell line and the production of monoclonal antibodies. The general methodology followed for obtaining monoclonal antibodies is described in Kohler & Milstein, 1975, *Nature.* 256:495–496, which is incorporated herein by reference. The transformation or fusion can be carried out in conventional ways, the fusion technique being described in a number of patents: U.S. Pat. Nos. 4,172,124; 4,350,683: 4,363,799; 4,381,292; and 4,423,147, whose techniques and technologies are herein incorporated by reference. The procedure is also described by Kennett et al., *Monoclonal Antibodies* (1980) and references therein, as well as Goding, infra, all of which are incorporated herein by reference. Human monoclonal antibodies are acquired by fusion of the spleen cells with the appropriate human fusion partner, such as WI-L2 and as described in European Application No. 82,301103.6, the relevant portions of such a procedure incorporated herein by reference. A detailed technique for producing mouse X mouse monoclonal antibodies is taught by Oi & Herzenberg, in Mishell & Shiigi, 1980, *Selected Methods in Cellular Immunology*:351–372, which also is incorporated herein by reference. The resulting hybridomas are screened to isolate individual clones, where each clone secretes a single monoclonal antibody to a given MRHAS.

The antibodies generated herein can be used without modification or may be modified in a number of ways. For example, such modification can be by way of labeling (meaning joining), either covalently or non-covalently, a moiety which directly or indirectly provides for some means of detection. A variety of such labels are known and include: substrates, enzymes, co-factors, inhibitors, chemiluminescers, fluorescers, radionuclides, magnetic particles, and the like.

Moreover, fragments of such monoclonal antibodies can exist that continue to possess noteable specificity for a given MRHAS. As such, all antibody binding fragments or reference to such 'fragaent(s) thereof' refers to a lesser portion of a complete antibody that retains some, if not all, of its binding specificity and capacity for a given MRHAS.

Therefore, one preferred embodiment of this invention involves a composition comprising a monoclonal antibody or binding fragment thereof which binds to one or more members of a group of homologous antigenic amino acid sequences comprising MRHAS.

A further embodiment of this invention involves a cell line that produces a monoclonal antibody or binding fragment thereof which binds to members of a family comprising MRHAS. As yet another embodiment of this invention involves a cell line that produces a monoclonal antibody or binding fragment thereof which binds to an epitope shared by bacterial and viral meningitis etiologic agents, wherein said cell line is RV-1 which was deposited at the American Type Tissue Collection (ATCC) Rockville, Md, on May 26, 1993 and accorded accession number HB 11362.

Another embodiment of this invention is a monoclonal antibody produced by the cell line RV-1 (ATCC HB 11362).

It is also a preferred embodiment of this invention that there be a monoclonal antibody capable of reacting with a MRHAS, wherein the monoclonal antibody specifically blocks the binding of an antibody produced by a cell line that produces a monoclonal antibody or binding fragment thereof which binds to members of a family comprising MRHAS, and where such cell line can be RV-1 (ATCC HB 11362).

Another embodiment involves a monoclonal antibody capable of reacting with an antigenic determinant, or homologs thereof, wherein the monoclonal antibody specifically blocks the binding of an antibody produced by a cell line that produces a monoclonal antibody or binding fragment thereof which binds to members of a family comprising MRHAS, and where said cell line can be RV-1 (ATCC HB 11362) and wherein said antigenic determinant is selected from the amino acid sequences presented in Table 3 and in SEQ ID NOS 2, 4, 6, 9, 12, 15, 18, 21, 24, 27, 29, 31, 33, 36 and 39.

TABLE 3

| VIRUS/ BACTERIUM/ CREMORINE | PROTEIN | AMINO ACID REGION | AMINO ACID SEQUENCE |
|---|---|---|---|
| Rubella virus | Structural Polyprotein | 95–115 | PSRAPPQQPQPPRMQTGRGGS |
| Rubella virus | Structural Polyprotein | 82–102 | ERQESRSQTPAPKPSRAPPQQ |
| Rubella virus | Structural Polyprotein | 306–326 | DMAAPPMPPQPPRAHGQHYGH |
| Rubella virus | Structural Polyprotein | 306–326 | DMAAPPTLPQPPCAHGQHYGH |
| HIV-1 | Gag Polyprotein | 138–158 | IQGQMVHQAISPRTLNAWVKV |
| HIV-1 | Envelope Polyprotein Precursor | 648–668 | HSLIEESQNQQEKNEQELLEL |
| Haemophilus influenzae | Lipoprotein E Precursor | 92–111 | NSPYAGWQVQNNKPFDGKDWT |
| Neisseria meningitidis | Opacity- Related Protein POPM3 | 1–13 | IQPPKNLLFSSLL |
| Streptococcus pneumoniae | Pneumococcal Surface Protein A | 416–436 | EEYNRLTQQQPPKAEKPAPAP |
| Listeria monocytogenes | Protein P60 Precursor | 144–164 | AVSTPVAPTQEVKKETTTQQA |
| Listeria monocytogenes | Protein P60 Precursor | 174–194 | VKQTTQATTPAPKVAETKETP |
| Listeria monocytogenes | Protein P60 Precursor | 242–262 | LAIKQTANTATPKAEVKTEAP |
| Listeria monocytogenes | Protein P60 Precursor | 285–305 | KKETATQQQTAPKAPTEAAKP |
| Chemokine hMCP-1 | | 86–99 | SMDHLDKQTQTPKT |
| Chemokine hMCP-3 | | 54–67 | FMKHLDKKTQTPKL |

Yet another embodiment of this invention is a monoclonal antibody capable of reacting with an antigenic determinant of the proteins presented in Table 4, wherein the antigenic determinant is selected from the amino acid sequences presented in Table 1 and in SEQ ID NOS 3, 5, 7, 10, 13, 16, 19, 22, 25, 28, 30, 32, 34, 37 and 40.

TABLE 4

| VIRUS/ BACTERIUM/ CREMOKINE | PROTEIN | AMINO ACID REGION | AMINO ACID SEQUENCE |
|---|---|---|---|
| Rubella virus | Structural Polyprotein | 102–108 | QPQPPRM |
| Rubella virus | Structural Polyprotein | 89–95 | QTPAPKP |
| Rubella virus | Structural Polyprotein | 313–319 | PPQPPRA |
| Rubella virus | Structural | 313–319 | LPQPPCA |

TABLE 4-continued

| VIRUS/ BACTERIUM/ CREMOKINE | PROTEIN | AMINO ACID REGION | AMINO ACID SEQUENCE |
|---|---|---|---|
| virus HIV-1 | Polyprotein Gag Polyprotein | 145–151 | QAISPRT |
| HIV-1 | Envelope Polyprotein Precursor | 655–661 | QNQQEKN |
| Haemophilus influenzae | Lipoprotein E Precursor | 99–105 | QVQNNKP |
| Neisseria meningitidis | Opacity- Related Protein POPM3 | 1–5 | IQPPKN |
| Streptococcus pneumoniae | Pneumococcal Surface Protein A | 423–429 | QQQPPKA |
| Listeria monocytogenes | Protein P60 Precursor | 151–157 | PTQEVKK |
| Listeria monocytogenes | Protein P60 Precursor | 181–187 | TTPAPKV |
| Listeria monocytogenes | Protein P60 Precursor | 249–255 | NTATPKA |
| Listeria monocytogenes | Protein P60 Precursor | 292–298 | QQTAPKA |
| Chemokine hMCP-1 | | 93–99 | QTQTPKT |
| Chemokine hMCP-3 | | 61–67 | KTQTPKL |

Pharmaceutical Formulations and Use

The monoclonal antibodies of this invention that bind MRHAS can also be incorporated as components of pharmaceutical compositions. The composition should contain a therapeutic or prophylactic amount of at least one of the monoclonal antibodies of the present invention with a carrier that is pharmaceutically effective. Such a pharmaceutical carrier should be any compatible, non-toxic substance that is suitable to deliver the monoclonal antibodies to the patient. Such carriers can be sterile water, alcohols, fats, waxes, and inert solids. The pharmaceutical composition may also be incorporate pharmaceutically acceptable adjuvants (eg. buffering agents or dispersing agents). Hence, the monoclonal antibodies of the present invention can be employed as separately administered compositions given in conjunction with other anti-bacterial or anti-viral agents.

The monoclonal antibodies, peptides, and pharmaceutical compositions thereof, of the present invention are particularly useful for oral or parenteral administration. It is preferred that the pharmaceutical compositions be administered parenterally: i.e., subcutaneously, intramuscularly, or intravenously. Therefore, this invention is providing compositions for parenteral administration that comprises a solution of the monoclonal antibody, peptide, or a cocktail thereof dissolved in an suitable carrier (which is preferably an aqueous carrier). Examples of the aqueous carriers that can be used are water, buffered water, 0.4% saline, 0.3% glycine, or the like. These solutions are to be sterile and generally free of particulate matter: Moreover, these compositions may be sterilized by conventional and well known sterilization techniques. The compositions may also contain pharmaceutically acceptable auxiliary substances. These substances are required to approximate physiological conditions such as pH adjusting and buffering agents, toxicity adjusting agents, and the like. Examples of these auxiliary substances are sodium acetate, sodium chloride, potassium chloride, calcium chloride, sodium lactate, etc. The concentration of antibody and/or peptide in these formulations can widely vary depending on its ultimate use, activity, and mode of administration of the composition. The concentration of antibody and/or peptide in these formulations will be selected primarily based on such factors as fluid volumes, viscosities, etc. It is preferable that such factors be chosen for the partiuclar mode of administration selected. The actual methods used for preparing parenterally administrable compositions will be known or is apparent to those skilled in the art and are described in *Remington's Pharmaceutical Science*, 15th Ed. (Easton: Mack Publishing Company, 1980), which is herein incorporated by reference.

The monoclonal antibodies and peptides of this invention can be lyophilized for storage and can be reconstituted in a suitable carrier prior to their use. Such techniques have been shown to be effective with conventional immunoglobulins and lyophilization and reconstitution techniques that are known in the art can be applied. It will also be appreciated by those skilled in the art however, that lyophilization and reconstitution can lead to varying degrees of antibody activity loss (e.g., with conventional immunoglobulins, IgM antibodies tend to have greater activity loss than IgG antibodies). As such, the use levels may have to be adjusted to compensate for any possible loss of activity.

The compositions containing the present monoclonal antibodies, or cocktails thereof can be dispensed for the prophylactic and/or therapeutic treatment of such diseases as meningitis or other maladies that may involve monocytes, monocyte-attracting chemokines or MRHAS (such as arteriosclserosis). In such therapeutic application, compositions are administered to patients who have contracted or begun to develop a disease involving MRHAS, chemokines, or chemokine recognizing monocytes in the pathogenic mechanism. The administration of such composition is in an amount sufficient to bind the chemical signal, i.e. to the MRHAS or chemokine. For example, a composition comprising the present monoclonal antibody is administered in a therapeutic application to a patient—already infected with a meningitis etiologic agent(s)—in an amount sufficient to cure, arrest, or at least partially arrest the infection and its complications.

In prophylactic applications, compositions containing the present antibodies or a cocktail thereof are administered to a patient not already infected by a disease-causing agent bearing an antigen that contains a MRHAS (ie. a meningitis-causing agent), but perhaps such patient has recently been exposed to or thought to have been exposed to, or was at risk of being exposed to such agent, to enhance the patient's resistance to such potential infection or to vaccinate against such agent.

The compositions containing the present peptides or cocktails thereof can be administered not only for the prophylactic and/or therapeutic treatment of meningitis, but also possibly for arteriosclserosis, or such related disease involving monocytes, monocyte-attracting chemokines or MRHAS. In therapeutic application, compositions are administered to a patient who has contracted or begun to develop a disease involving MRHAS, or homologs thereof, or chemokine recognizing monocytes in the pathogenic mechanism, in an amount sufficient to block the MRHAS signal recognition by monocytes. For example, a composition containing such a peptide may be administered in a therapeutic application to a patient already infected with a meningitis etiologic agent(s), in an amount sufficient to block MRHAS recognition sites on monocytes by interfering with the ability of said agents to attract and infect monocytes (and thus interfere with the infectivity of the CNS by said agent(s).

In prophylactic applications, compositions containing one or more peptides mimicking members of the MRHAS family or a cocktail thereof are also useful as the active component of vaccines capable of inducing protective immunity against both bacterial and viral meningitis causing agents. The possible routes of administration, the antigen doses, and the number and frequency of injections will vary from individual to individual and may parallel those currently being used in providing immunity to other viral infections. For example, the vaccines of the present invention are pharmaceutically acceptable compositions that contain at least one peptide of this invention, its analogues or mixtures or combinations thereof, in an amount that is effective in a mammal (including humans) treated with that composition to raise antibodies sufficient to protect such mammal from viral or bacterial meningitis for a period of time.

The vaccines of the present invention are prepared in accordance with known methods and are conveniently and conventionally combined with physiologically acceptable carrier materials, such as pharmaceutical grade saline, tetanus toxoid, and keyhole limpet hemocyanin. The vaccine compositions of the present invention may also include adjuvants or other enhancers of immune response, such as liposomes, alum preparations, or immunomodulators. Furthermore, these vaccine compositions may comprise other antigens to provide immunity against other viruses and bacteria. The amount of these other antigens is again dependent on the mammal to be treated, the type of disease, and the actual course of the disease. A single or multiple administration of the compositions can be done with dose levels and pattern being selected by the administering physician. However, the antigen should be present in an amount effective to raise antibodies sufficient to protect the treated mammal from that pathogen or virus for a period of time.

Furthermore, the monoclonal antibodies of the present invention may find use as a target-specific carrier molecule. Such use would involve binding an antibody to either a toxin to form an immunotoxin, or radioactive material or drug to form a radiopharmaceutical or pharmaceutical. Methods for producing immunotoxins, radiopharmaceuticals, or such pharmaceuticals are well known as set out in 1984, *Cancer Treatment Reports* 68:317 which is incorporated herein by reference.

It is also possible that heteroaggregates of the monoclonal antibodies from the present invention and human T-cell activators (such as monoclonal antibodies to the CD3 antigen or to the Fc gamma receptor on T-cells) may enable human T-cells or Fc-gamma bearing cells (such as K cells or neutrophils) to kill meningitis-etiologic agent infected cells via antibody dependent cell-mediated cytolysis. By way of example, such heteroaggregates may be assembled by covalently cross-linking the anti-MRHAS antibodies to the anti-CD3 antibodies using the heterobifunctional reagent N-succinimidyl-3-(2-pyridyldithiol)-propionate, as described by Karpowsky et al., 1984, *J. Exp. Med.* 160:168, which is herein incorporated by reference.

It is therefore, a preferred embodiment of this invention that there be a monoclonal antibody composition specifically reactive listed in Table 3 (SEQ ID NOS 2, 4, 6, 9, 12, 15, 18, 21, 24, 27, 29, 31, 33, 36 and 39), wherein the sequence or homolog of said sequence is within the region listed in Table 3, and wherein said monoclonal antibody is capable of blocking the infectivity of the virus or bacteria.

A further embodiment of this invention involves a monoclonal antibody composition specifically reactive with an epitope of a chemokine selected from one of the chemokine sequences listed in Table 4 (SEQ ID NOS 3, 5, 7, 10, 13, 16, 19, 22, 25, 28, 30, 32, 34, 37 and 40) wherein the sequence or homolog of said sequence is within the region listed in Table 3 (SEQ ID NOS 4, 6, 9, 12, 15, 18, 21, 24, 27, 29, 31, 33, 36 and 39) and wherein said monoclonal antibody is capable of binding said chemokine in vivo to significantly reduce CNS infectivity of meningitis etiologic agents.

Yet another embodiment of this invention is a vaccine formulation comprising an immunogenic peptide comprising one or more members of the MRHAS family or an immunogenic portion thereof.

Another embodiment of this invention is a method for protecting against CNS infection of bacterial and/or viral meningitis etiologic agents by blocking a recognition site on monocytes that recognizes MRHASs.

A further embodiment of this invention is a method of treating a patient to prevent an infection due to a meningitis etiologic virus and/or bacteria, said method comprising administering a prophylactically effective amount of a composition useful in the prophylactic or therapeutic treatment of viral and/or bacterial meningitis, said composition comprising a monoclonal antibody or binding fragment thereof which binds to MRHAS shared by viral and/or bacterial meningitis etiologic agents.

Yet another embodiment of this invention is a method of treating a patient infected with a meningitis etiologic virus and/or bacteria, said method comprising administering a therapeutically effective amount of a composition useful in the prophylactic or therapeutic treatment of viral and/or bacterial meningitis, said composition comprising a monoclonal antibody or binding fragment thereof which binds to MRHAS shared by viral and/or bacterial meningitis etiologic agents.

Another embodiment of this invention entails an article of manufacture adapted for use in an immunoassay for antibodies to bacterial and/or viral meningitis etiologic agents comprising a solid support having bound thereto a peptide comprising one or more members of a group of peptides based on MRHASs, wherein said peptide having the formula a---X---b, wherein X is a sequence of at least 7 amino acids taken as a block selected from the group comprised in Table 5 below, with said block maintaining the sequence in the N terminus to C terminus direction of the native amino acid sequence and analogue thereof, said analogues resulting from conservative substitutions in or modifications to the native amino acid sequence block;

a is selected from the group consisting of:
  (i) an amino terminus;
  (ii) one to eight amino acids taken as a block from and maintaining the sequence and N terminus to C terminus direction of that portion of the native amino acid sequence of the protein immediately N-terminal to said X or conservative substitutions in or modifications thereto; and
  (iii) a substituent effective to facilitate coupling of the peptide to another moiety; and b is selected from the group consisting of:
  (i) a carboxy terminus;
  (ii) one to eight amino acids taken as a block from and maintaining the sequence and N terminus to C terminus direction of that portion of the native amino acid sequence of the protein immediately C-terminal to said X or conservative substitutions in or modifications thereto; and
  (iii) a substituent effective to facilitate coupling of the peptide to another moiety.

A further embodiment of the present invention is a composition useful in the prophylactic or therapeutic treatment of viral and/or bacterial meningitis, said composition comprising peptides selected from the MRHAS family and/or the peptides described in the preceeding paragraph.

Diagnostic Uses of Monoclonal Antibodies

The monoclonal antibodies and peptides of the present invention are also useful for diagnostic purposes and can be either labelled or unlabelled. Diagnostic assays typically entail the detection of a complex formation through the binding of the monoclonal antibody to a MRHAS. When unlabelled, the antibodies can find use, for example, in agglutination assays. Moreover, unlabelled antibodies can be used in combination with other labelled antibodies (second antibodies) that are reactive with the monoclonal antibody of the present invention. An example of this is antibodies specific for immunoblobulin. Alternatively, the monoclonal antibodies can be directly labelled. A wide variety of labels may be employed, such as enzymes, enzyme substrates, enzyme cofactors, enzyme inhibitors, radionuclides, fluorescers, ligands (particularly haptens), etc. In addition, numerous types of immunoassays are available and, by way of example, some assays include those described in U.S. Pat. Nos. 3,817,827; 3,850,752; 3,901,654; 3,935,074; 3,984,533; 3,996,345; 4,034,074; and 4,098,876, all of which (with references) are incorporated herein by reference.

It is common for the monoclonal antibodies and peptides of the present invention to be employed in enzyme immunoassays, where for example, the subject antibodies (or second antibodies from a different species) are conjugated to an enzyme. When a biological sample containing MRHAS antigens, such as human blood serum, saliva, cerebrospinal fluid or bacterial and/or viral infected cell culture suspension, is combined with the subject antibodies, binding occurs between the antibodies and those molecules exhibiting the desired epitope. It should be noted that the biological sample may require concentration in order to detect organisms of low titer. Such proteins, bacterial or viral particles may then be separated from any unbound reagents and a second antibody (labeled with an enzyme) added. The presence of the antibody-enzyme conjugate specifically bound to the antigen can then be determined. Other conventional techniques well known to those skilled in the art may also be used.

Kits can also be equipped with the subject monoclonal antibodies of the present invention, for detection of meningitis etiologic agents or for the presence of MRHASs. Hence, the subject monoclonal antibody compositions of the present invention may be provided, usually in a lyophilized form, either alone or in conjunction with additional antibodies specific for other epitopes of meningitis etiologic agents. The antibodies, which may be conjugated to a label, or unconjugated, are included in such kits along with buffers such as Tris, phosphate, carbonate, and the like, along with the requesite stabilizers, biocides, inert proteins (eg. bovine serum albumin) that are standard to those skilled in the art.

It is therefore, a preferred embodiment of this invention that there be a monoclonal antibody composition specifically reactive with an epitope selected from one the bacterial or viral sequences listed in Table 3 (SEQ ID NOS 2, 4, 6, 9, 12, 15, 18, 21, 24, 27, 29, 31, 33, 36 and 39) wherein the sequence or homolog of said sequence is within the region listed in Table 3, and wherein said monoclonal antibody is capable of detecting the infectivity of the virus or bacteria. As a note, that use of the said antibodies with biological samples containing low titer meningitis etiologic agents may require concentrating said samples before the diagnostic procedure is performed.

A further embodiment involves a monoclonal antibody composition specifically reactive with an epitope selected from one of the chemokine sequences listed in Table 3 (SEQ ID NOS 2, 4, 6, 9, 12, 15, 18, 21, 24, 27, 29, 31, 33, 36 and 39) wherein the sequence or homolog of said sequence is within the region listed in Table 3, and wherein said monoclonal antibody is capable of detecting said chemokine in vivo to indicate CNS infectivity of meningitis causing agents.

Yet another embodiment of this invention entails a method of diagnosing the presence of bacterial and/or viral meningitis etiologic agents in a biological sample, said method comprising the steps of forming an antibody/antigen complex wherein the antibody portion of said complex comprises a monoclonal antibody capable of binding to both bacterial and vital meningitis etiologic agents, and detecting the presence of the antibody/antigen complex formed.

A further embodiment of this invention involves an immunoassay to detect the presence of antibodies to bacterial and/or viral meningitis etiologic agents in a biological sample comprising contacting said sample with one or more immunogenic peptide(s), where said peptide is selected from one or more members of the MRHAS family, the improvement comprising the method of screening for bacterial and/or viral meningitis etiologic agents in one test.

A further embodiment of this invention involves an immunoassay to detect the presence of antibodies to bacterial and/or viral meningitis etiologic agents in a biological sample comprising contacting said sample with one or more immunogenic peptide(s), where said peptide is selected from one or more members of the MRHAS family comprising a peptide having the formula a---X---b wherein:

X is a sequence of at least 7 amino acids taken as a block selected from the group comprised in Table 5:

TABLE 5

(i) the amino acid sequence of the Structural Polyprotein of a strain of Rubella virus that corresponds to $AA_{102}$–$AA_{108}$ (SEQ ID NO: 3) of said protein of the $M_{33}$ strain of Rubella virus as set forth in FIG. 1 (SEQ ID NO: 1):

(ii) the amino acid sequence of the Structural Polyprotein of a strain of Rubella virus that corresponds to $AA_{89}$–$AA_{97}$ (SEQ ID NO: 5) of said protein of the M33 strain of Rubella virus as set forth in FIG. 1 (SEQ ID NO: 1)

(iii) the amino acid sequence of the Structural Polyprotein of a strain of Rubella virus that corresponds to $AA_{313}$–$AA_{319}$ (SEQ ID NO: 7) of said protein of the M33 strain of Rubella virus as set forth in FIG. 1 (SEQ ID NO: 1);

(iv) the amino acid sequence of the Structural Polyprotein of a strain of Rubella virus that corresponds to $AA_{103}$–$AA_{109}$ (SEQ ID NO: 10) of said protein of the Therien strain of Rubella virus as set forth in FIG. 2 (SEQ ID NO: 8);

(v) the amino acid sequence of the Structural Polyprotein of a strain of Rubella virus that corresponds to $AA_{900}$–$AA_{96}$ of said protein of the Therien strain of Rubella virus as set forth in FIG. 2 (SEQ ID NO: 8);

(vi) the amino acid sequence of the Structural Polyprotein of a strain of Rubella virus that corresponds to $AA_{314}$–$AA_{320}$ of said protein of the Therien strain of Rubella virus as set forth in FIG. 2 (SEQ ID NO: 8);

(vii) the amino acid sequence of the Gag Polyprotein of an isolate of the HIV-1 that corresponds to $AA_{145}$–$AA_{151}$ (SEQ ID NO: 10) of the Gag polyprotein of the LV isolate of HIV-1 as set forth in FIG. 3 (SEQ ID NO:11);

(viii) the amino acid sequence of the Envelope Polyprotein Precursor of an isolate of the HIV-1 that corresponds to $AA_{655}$ to $AA_{661}$ (SEQ ID NO: 16) of the Envelope Polyprotein Precursor of the LAV-1a isolate of HIV-1 as set forth in FIG. 4 (SEQ ID NO: 14);

(ix) the amino acid sequence that corresponds to $AA_{99}$–$AA_{105}$ (SEQ ID NO: 19) of the Lipoprotein E Precursor of *Haemophilus influenzae* as set forth in FIG. 5 (SEQ ID NO: 17);

(x) the amino acid sequence that corresponds to $AA_1$ to $AA_5$ (SEQ ID NO: 2) of the Opacity-Related Protein POPM3 of *Neisseria meningitidis* as set forth in FIG. 6 (SEQ ID NO: 20);

(xi) the amino acid sequence that corresponds to $AA_{423}$ to $AA_{429}$ (SEQ ID NO: 25) of the Pneumococcal Surface Protein A of *Streptococcus pneumoniae* as set forth in FIG. 7 (SEQ ID NO: 23);

(xii) the amino acid sequence that corresponds to $AA_{151}$–$AA_{157}$ (SEQ ID NO: 28) of the Protein P60 Precursor of *Listeria monocytogenes* as set forth in FIG. 8 (SEQ ID NO: 26);

(xiii) the amino acid sequence that corresponds to $AA_{181}$–$AA_{187}$ (SEQ ID NO: 30) of the Protein P60 Precursor of *Listeria monocytogenes* as set forth in FIG. 8 (SEQ ID NO: 26);

(xiv) from the amino acid sequence of that corresponds to $AA_{269}$–$AA_{255}$ (SEQ ID NO: 32) of the Protein P60 *Precursor of Listeria monocytogenes* as set forth in FIG. 8 (SEQ ID NO: 26);

(xv) from the amino acid sequence that corresponds to $AA_{292}$–$AA_{298}$ (SEQ ID NO:34) of the Protein P60 Precursor of *Listeria monocytogenes* as set forth in FIG. 8 (SEQ ID NO: 26);

(xvi) from the amino acid sequence of a variant of the chemokine human Monocyte Chemoattractant Factor hMCP-1, that corresponds to $AA_{93}$–$AA_{99}$ (SEQ ID NO: 37) of hMCP-1 as set forth in FIG. 9 (SEQ ID NO: 3);

(xvii) from the amino acid sequence of the chemokine hMCP-3, that corresponds to $AA_{61}$–$AA_{67}$ SEQ ID NO: 40 of hMCP-3 as set forth in FIG. 10 (SEQ ID NO: 38); and (xviii) from any amino acid sequence present within a protein that is homologous to members of the MRHAS family;

with said block maintaining the sequence in the N terminus to C terminus direction of the native amino acid sequence and analogue thereof, said analogues resulting from conservative substitutions in or modifications to the native amino acid sequence block;

a is selected from the group consisting of:
 (i) an amino terminus;
 (ii) one to eight amino acids taken as a block from and maintaining the sequence and N terminus to C terminus direction of that portion of the native amino acid sequence of the protein immediately N-terminal to said X or conservative substitutions in or modifications thereto; and
 (iii) a substituent effective to facilitate coupling of the peptide to another moiety; and b is selected from the group consisting of:
 (i) a carboxy terminus;
 (ii) one to eight amino acids taken as a block from and maintaining the sequence and N terminus to C terminus direction of that portion of the native amino acid sequence of the protein immediately C-terminal to said X or conservative substitutions in or modifications thereto; and
 (iii) a substituent effective to facilitate coupling of the peptide to another moiety, the improvement comprising the method of screening for bacterial and/or viral meningitis etiologic agents in one test.

Yet a further embodiment of the present invention is a method for analyzing a sample of a biological fluid with regard to the presence of anti-X antibodies therein, where X is selected from one or more members of the group comprising:
(i) Rubella virus;
(ii) HIV-1;
(iii) *Hemophilus influenzae;*
(iv) *Nisteria meningitidis;*
(v) *Streptococcus pneumoniae;*
(vi) *Listeria monocytogenes,* and
comprising the steps of:
A) providing a solid support having bound thereto a peptide selected from one or more members of the MRHAS family, or said peptide is selected from one or more members of the MRHAS family comprising a peptide having the formula a---X---b wherein:
 X is a sequence of at least 7 amino acids taken as a block selected from the group comprised in Table 5, and with said block maintaining the sequence in the N terminus to C terminus direction of the native amino acid sequence and analogue thereof, said analogues resulting from conservative substitutions in or modifications to the native amino acid sequence block; a is selected from the group consisting of:
 (i) an amino terminus;
 (ii) one to eight amino acids taken as a block from and maintaining the sequence and N terminus to C terminus direction of that portion of the native amino acid sequence of the protein immediately N-terminal to said X or conservative substitutions in or modifications thereto; and
 (iii) a substituent effective to facilitate coupling of the peptide to another moiety; and b is selected from the group consisting of:
 (i) a carboxy terminus;
 (ii) one to eight amino acids taken as a block from and maintaining the sequence and N terminus to C terminus direction of that portion of the native amino acid sequence of the protein immediately C-terminal to said X or conservative substitutions in or modifications thereto; and
 (iii) a substituent effective to facilitate coupling of the peptide to another moiety, B) contacting said solid support with said human sample to provide a sample-contacted support;
C) washing said sample-contacted support to provide a washed support; and
D) determining whether human antibodies are bound to said support.

Preparation and Use of Synthetic Peptides

Novel peptides are provided in the present invention which immunologically mimic protein epitopes encoded by infectious agents that cause meningitis and by monocyte-attracting chemokines. To accommodate variations among different infectious agents, adjustments for conservative substitutions, and selectionamong the alternatives where non-conservative substitutions are involved, may be made. There are many uses for these peptides which include, for example, use as: immunogens for a vaccine; blockers of MRHAS recognition sites on monocytes, interfering with the ability of meningitis etiologic agents to attract and infect monocytes and thereby block access of the infectious agent to the CNS; blockers of MRHAS recognition sites on monocytes involved in plaque build-up that occurs during atherosclerosis; and as antigens in diagnostic kits to detect antibodies in biological fluid as indication of infection by meningitis etiologic agents. Depending upon the nature of the protocol, the peptides may be conjugated to a carrier or other compounds, unlabeled or labeled, bound to a solid surface, or the like.

Embodiments of the present invention include peptides of interest derived from MRHAS family members listed in Table 1. (SEQ ID NOS 3, 5, 7, 10, 13, 16, 19, 22, 25, 28, 30, 32, and 34). Further embodiments include peptides of interest derived from MRHAS family members and their parent monocyte-attracting chemokines listed in Table 2(SEQ ID NO: 37 and 40). Other possible embodiments include MRHAS family members found on proteins listed in Table 3(SEQ ID NOS 2, 4, 6, 9, 12, 15, 18, 21, 24, 27, 29, 31, 33, 36 and 39).

The peptides of interest will include at least five, sometimes six, sometimes seven, sometimes eight, sometimes 15, sometimes 21, usually fewer than about 50 and preferably fewer than about 25 amino acids included within a sequence homologous to a member of the MRHAS family. It is desired that a given peptide be as small as possible while still maintaining all of the immunoreactivity or monocyte attracting activity or-the larger corresponding peptide. Furthermore, it may be desirable in some instances to join two or more oligopeptides which are non-overlapping to form a single peptide structure or to use them as individual peptides at the same time, which separately or together provide equivalent sensitivity to the parent.

A given peptide may be modified by introducing conservative or non-conservative substitutions in the peptide, usually fewer than 50 number percent, and more usually fewer than 30 number percent, more usually with fewer than 15 number percent of the amino acids being exchanged (Waterman, 1986, *Nucleic Acids Res.* 14:9095; Hitachi, HIBIO MacDNASIS Pro: DNA and Protein Sequence Analysis Software System Reference Manual, both incorporated in their entirety by reference). In those situations where amino acid regions are found to be polymorphic, it may be desirable to vary one or more particular amino acids to more effectively mimic the differing epitopes of the different meningitis etiologic infectious agents, or monocyte attracting chemokines.

It is important that it be understood that the polypeptide employed in the present invention need not be identical to any particular MRHAS family member, so long as the subject peptide is able to provide for immunological competition with proteins of at least one of the members of the MRHAS family and/or demonstrate monocyte recognition and/or attracting activity. Therefore, the subject peptide may be subject to various changes, such as substitutions, insertions, and deletions, either conservative or nonconservative, where such changes may provide for certain advantages in their use.

It is also important to point out that one, two, or more amino acids may be added to the termini of an oligopeptide or peptide to provide for ease of linking peptides one to another, for coupling to a support, or larger peptide and for reasons to be discussed subsequently, for modifying the physical or chemical properties of the peptide or oligopeptide, or the like.

In the present invention, the term amino acid is used to include, but not limited to, all natural occurring amino acids and all synthetic or non-natural amino acids such as homocysteine. The term 'amino acids selected as a block' (or other similar statements) means a linear sequence of a set number of amino acids that taken together form a group. The term 'antigenic determinant'0 means the structual component of an antigen molecule responsible for its specific interaction with antibody molecules elicited by the same or related antigen as defined by *Dorland's Pocket Medical Dictionary* 23ed. (Philadelphia: Saunders, 1982) at 198; Morris, ed. Academic Press Dictionary of Science and Technology (San Diego: Academic Press, 1992) which are both incorporated in their entirety by reference. The term 'conservative substitution' means the substitution of one or more amino acids for another in which the antigenic determinant (including its secondary structure and hydropathic nature) of a given antigen is completely or partially conserved in spite of the substitution. The term 'analogues of a peptide' means amino acid insertions, deletions, substitutions, and modifications of one or more sites in the peptide chain. The term 'immunogenic' means the property that endows a substance with the capacity to provoke an immune response (Dorland, infra). The terms 'corresponds' and 'corresponding' refers to the native amino acids of those defined region of a given peptide sequence. Finally, amino acids such as cysteine, lysine, glutamic or aspartic acid, tyrosine, or the like may be introduced at the C- or N-terminus of a given peptide or oligopeptide to provide for a useful functionality for linking purposes. It will be appreciated by those skilled in the art that cysteine is particularly preferred to facilitate covalent coupling to other peptides or to form polymers by oxidation.

Moreover, a given peptide or oligopeptide sequence may differ from the natural sequence by the sequence being modified by terminal-$NH_2$ acylation (eg. by acetylation, or thioglycolic acid amidation, terminalcarbosy amidation, e.g., with ammonia or methylamine) to provide stability, increased hydrophobicity for Linking or binding to a support or other molecule, or for purposes of polymerization.

Of particular interest to the present invention is the use of the mercaptan group of cysteins or thioglycolic acids used for acylating terminal amino groups, or the like, for linking two of the peptides or oligopeptides or combinations thereof by a disulfide linkage or a longer linkage to form polymers that contain a number of MRHAS epitopes. Such polymers have the advantage of increased immunological reaction. Furthermore, where different peptides are used to make up the polymer, they possess the additional ability to induce antibodies that immunoreact with several antigenic determinants of the different meningitis etioligic agents.

In order to achieve the formation of antigenic polymers (ie. synthetic multimers), compounds may be utilized having bishaloacetyl groups, nitroarylhalides, or the like, where the reagents being specific for thio groups. Therefore, the link between two mercapto groups of the different peptides or oligopeptides may be a single bond or may be composed of a linking group of at least two, typically at least four, and not more than about 16, but usually not more than about 14 carbon atoms.

To prepare the novel peptides of the present invention, any of the conventional peptide production techniques may be employed. These techniques include synthesis, recombinant DNA technology and combinations thereof. The peptide may be synthesized in solution or on a solid support in accordance with conventional techniques. A variety of automatic synthesizers are commercially available and can be used in accordance with known protocols. For example, see Stewart & Young, 1984, *Solid Phase Peptide Synthesis* 2nd ed., Pierce Chemical Co.; Tam et al., 1983, *J. Am Chem. Soc.* 105:6442 which are both incoporated herein by reference. Recombinant DNA technology may be utilized where a synthetic gene may be prepared by employing single strands which code for the given MRHAS polypeptide or substantially complementary strands thereof, where the single strands overlap and can be brought together in an annealing medium so as to hybridize. The hybridized strands may then be ligated to form the complete gene, and, by choice of appropriate termini, the gene may be inserted into expression vectors, which are readily available today. For example, see Maniatis et al., 1982, *Molecular Cloning, A Laboratory Manual*, Cold Spring Harbor Laboratory which is herein incorporated by reference. In the alternative, the region of the genome coding for the given MRHAS peptide may be cloned by conventional recombinant DNA techniques and expressed (See Maniatis, infra).

It is therefore, a preferred embodiment of this invention that there be a peptide having the formula a--X--b wherein, X is a sequence of at least 7 amino acids taken as a block selected from the group comprised in Table 5, with said block maintaining the sequence in the N terminus to C terminus direction of the native amino acid sequence and analogue thereof, said analogues resulting from conservative substitutions in or modifications to the native amino acid sequence block;

a is selected from the group consisting of:
(i) an amino terminus;
(ii) one to eight amino acids taken as a block from and maintaining the sequence and N terminus to C terminus direction of that portion of the native amino acid sequence of the protein immediately N-terminal to said X or conservative substitutions in or modifications thereto; and
(iii) a substituent effective to facilitate coupling of the peptide to another moiety; and b is selected from the group consisting of:
(i) a carboxy terminus;
(ii) one to eight amino acids taken as a block from and maintaining the sequence and N terminus to C terminus direction of that portion of the native amino acid sequence of the protein immediately C-terminal to said X or conservative substitutions in or modifications thereto; and
(iii) a substituent effective to facilitate coupling of the peptide to another moiety.

Other features and advantages of the present invention will become apparent from the following experimental descriptions, which describe the invention by way of example. The examples are offered by way of illustration and not by way of limitation.

EXAMPLE I

Generation and Characterization of Monoclonal Antibodies

Example I describes the method for the generation of hybridoma cell lines that produce monoclonal antibodies with a specificity for MRHAS. This method involves the use of purified Rubella virus as the immunogen. The protocols for the generation of the hybridima cell lines that produce the said monoclonal antibody and the characterization of the antibodies were as follows.

Rubella virus, strain M33, was obtained as the first passage after primary isolation. The RV strain was obtained from the laboratories of the National Institute of Health. Murine fibroblasts (L cells), used to generate stock virus, were maintained in monolayer cultures and were routinely propagated at 37° C. with minimal Eagle's medium (MEM) supplemented with 5% fetal calf serum (FCS, Grand Island Biological Company, GIBCO), 100 μg/ml streptomycin, and 100 IU/ml penicillin. Stock virus was routinely prepared by inoculating semiconfluent monolayers of L cells with RV at a multiplicity of infection (m.o.i.) of 0.01. After adsorption at 34° C. in a humid atmosphere containing 5% C02 for 1 hour, additional medium was added and the flask was incubated at 34° C for 6 days, at which time the culture supernatant was collected and frozen at −80° C.

Virus purification was accomplished as follows. L cell monolayers were infected at an m.o.i. of 0.01 and incubated at 34° C. for 6 days as described. The culture supernatants were collected and centrifuged at 3000×g for 20 min. All procedures were carried out a 4° C. unless otherwise stated. The supernatant obtained was recentrifugated at 100,000×g for 3 hours and the resulting pellet was resuspended in 0.2 ml TNE buffer (0.15 M NaC1, 50 Mm Tris-HCl, and 1 mM EDTA, pH 7.8). This sample was layered onto a 16 mi 25–45% discontinuous Renografin-60 (Reno M-60, Diatrisoate Meglumine, 60%, Squibb) gradient prepared with TNE buffer and centrifuged in an SW 27 Rotor at 55,000×g for 2 hours. The single, sharp band at the interface was collected, pelleted as described previously, resuspended in 0.5 ml TNM buffer (0.15 M NaCl, 50 mM Tris-HCl, 1 mM $MgCl_2$, pH 7.8), and layered on a 12 ml 30–45% continuous Renografin gradient prepared with TNM buffer. After centrifugation at 200,000×g for 3 hours, 0.5 ml fractions were collected. An aliquot was removed from each fraction for ELISA and infectivity tests (both described below). Appropriate fractions were then pooled, diluted with TNM buffer, and centrifuged at 100,000×g for 3 hours to remove the Renographin. Rubella antigen, prepared in this way, was used to immunize mice for the construction of hybridomas.

The ELISA was performed according to the procedure described by Volier in Rose & Freidman, eds., 1976, *Manual of Clinical Immunology*:506–512 which is incoporated herein by reference. Viral samples were diluted into coating buffer and duplicate 200 μl aliquots were adsorbed to microtiter plate wells (Cooke Laboratory Products, Dynatech Laboratories Inc., Alexandria, Va.). After coating, a predetermined 1/16 dilution of human anti-Rubella antiserum (H1 titer=1/128) was added to each well. Antibody binding was measured using a previously determined 1/2,000 dilution of rabbit antihuman IgG (Flow Laboratories) linked to alkaline phosphatase. The A400nm was determined after 30 minutes incubation at room temperature.

The infectivity test is a technique used to titer RV and was based on the ability of RV-infected cells to adsorb erythrocytes. It employs, in principle, the procedure incorporated herein by reference of Hotchin et al., 1960, *Virology* 10:275–280 for measuring the infectivity of noncytopathic viruses. Serial doubling dilutions of RV suspensions were used to infect confluent monolayers of L2 cells grown in tissue culture chamber slides (Lab Tek Products, Division of Miles Laboratories, Inc., Illinois). Two-chamber slides were used. Each chamber received a 50 μl aliquot of the appropriate RV dilution. Virus was allowed to adsorb for 1 hour at 34° C. and 2.5 ml of medium and 50 μl of a 20% suspension of heparinized sheep erythrocytes in Alserver's solution were added directly to each chamber. The slides were then incubated for 24 hours at 34° C. The chambers were removed and each slide was washed gently by immersion if pH 7.4 Dulbecco phosphate-buffered saline (PBS) at room temperature and examined microscopically for hemadsorbing cells. Uninfected control monolayers were treated in an identical fashion.

Mice were immunized using the following procedure. A Balb/c mouse was inoculated intraperitoneally (IP) with 250 µg of *M.tuberculosis* and 15 µg of purified RV suspended in 45% Renografin. Approximately 4 weeks later, 4 booster doses of 10 µg of virus each were given intravenously at day minus 5, minus 4, minus 3 and minus 2, prior to fusion. The final boost was accompanied by an additional injection of the same dose IP. Serum was taken from the immunized mouse throughout to monitor antibody production against RV proteins.

A Balb/c mouse was immunized as previously described and one day after the final booster doses of purified virus, the mouse was sacrificed and a suspension of spleen cells was prepared and fused with myeloma cells (P3X63Ag8) in a ratio of 5:1 using 50% polyethylene glycol according to the procedure described by Koprowski et al., 1977, *Proc. Natl. Acad. Sci.* 74:2985–2988 incorporated herein by reference. Cultures containing 1×105 cells in 100 µl were established in 96–2311 Linbro plastic plates (Flow Laboratories, McLean, Va., USA) where each well contained a feeder layer of 4×103 murine peritoneal exudate cells (macrophages). Colonies appeared in 2 to 3 weeks and culture medium in appropriate well were screened for anti-Rubella antibody in the ELISA employing infected and uninfected L cell lysates as antigen. Cells that were producing antibody were subcloned and retested.

ELISA screening of clones was performed according to the procedure described by Voller, infra, as previously described. Infected L cell monolayers were detached by scraping, sonicated and diluted in coating buffer to give a final protein concentration of 100 µg protein/100 µl of lysate. Each microwell was coated with 200 µl of lysate. After coating overnight at 4° C., 100 µl of each test supernatant was added. After a 90 minute incubation at 37° C., and washing, 100 µl of rabbit anti-mouse IgG, linked to alkaline phosphatase (Flow Laboratories) was added, and the plate was reincubated for one hour at 37° C. After addition of 100 µl of a 10% diethanolamine solution (pH 9.8), containing 1 mg/ml p-nitrophenylphosphate (Sigma), the plate was incubated for one hour at 37° C. and the A400nm was determined as before.

The immunoglobulin class of anti-Rubella virus antibodies produced by the positive clones was determined by testing the supernatant from such clones against affinity purified anti-mouse immunoglobulin (South Biotech), using the ELISA methods.

Polyacrylamide slab gel electrophoresis (PAGE) of Rubella virus proteins was performed according to Laemmli, 1970, *Nature* 227:680–685 incorporated herein by reference. RV polypeptides in sample buffer (0.062 M Tris-HCl, pH 6.8) containing 2% SDS, 1% (v/v) glycerol, 0.5% (w/v) bromophenol blue and 1% 2-mercaptoethanol were placed in a boiling water bath for 2 minutes prior to electrophoresis at 25 mA for 2 hours on a 10% discontinuous acrylamide slab gel system. Aliquots of 15 µl containing 5 µg of protein were applied to each gel lane. Protein standards used for gel calibration were as follows: bovine serum albumin (66200), ovalbumin (45,000), carbonic anhydrase (28,000), soybean trypsin inhibitor (20,100), and alpha-lactalbumin (14,200) (Bio-Rad). Gels were stained with silver according to the procedure described by Wray et al., 1981, *AnalFt. Biochem.* 118:197–203 incorporated herein by reference.

Rubella virus proteins separated by PAGE were transferred electrophoretically from the SDS-PAGE gel to nitrocellulose paper (Bio-Rad) by the method described by Towbin et al., 1979, *Proc. Nat. Aced. Sci.* 76:4350–4354 incorporated herein by reference. A constant current of 35 mA was applied to the gel-nitrocellulose paper sandwich for 1 hour, in an electroblot buffer of 25 mM Tris-HCl, 192 mM glycine and 20% (v/v) methanol at pH 8.3. The proteins transferred onto the blot were either stained with amido black or detected by enzyme immunoassay. The latter was performed by soaking the paper in PBS containing 1% milk for 30 minutes in order to clock non-specific protein binding sites. The paper was then incubated with monoclonal antibody at 37° C. for 1 hour., washed 3 times with PBS followed by and hour incubation at 37° C. with peroxidase-conjugated goat anti-mouse immunoglobulin (Cappel, Cochranville, Pa.) diluted 1/1000 in PBS containing 3% BSA. After 3 additional washes, the blots were soaked in a solution of 0-dianisidine prepared as described by Towbin, infra.

Characterization of Mabs directed against RV 30,000 dalton protein

One fusion yielded 268 clones. After initial screening, 12 (4.5%) of the 266 clones were positive against infected cell lysates. The 12 clones were recloned and only 4 of these remained stable antibody producers. The 4 clones as listed in Table 6 were designed RV1–RV4 and further characterized according to Ig class and molecular weight of the antigen recognized.

TABLE 6

Summary of Mab characteristics of 4 stable hybridoma clones obtained

| Original done | Cell line Designation | Immunoglobulin Class/subclass | A 410 nm | Molecular weight of antigen recognized (Kd) |
|---|---|---|---|---|
| 101 B1 | RV1 | — | 0.248 | — |
| 201 A5 | RV2 | — | 0.126 | — |
| 6C6 | RV3 | — | 0.241 | — |
| 1A1 | RV4 | — | 0.174 | — |

The first band to appear on immunoblotting was consistently the p30 core protein. However, a second band was observed at approximately 40,000 Kd and was clear after 30 minutes incubation. The larger 40 Kd protein has been designated E2 and has been shown to have a molecular weight of 35–38 Kd (vaccine strain and wild type 349). The E2 membrane protein is glycosylated and is detected in mature virions as a protein with a molecular weight of approximately 40,000–43,000 daltons. These results are summarized in FIG. 11.

The four hybridomas were isolated from a single fusion, but can be seen to be independent isolates from the differences observed in the immunoglobulin class determinations. In spite of their obvious differences, the clones were all directed against the same (cross-reacting) epitopes which appears to be on the RV core protein having a molecular weight of approximately 30,000.

A comparison of nucleotide sequences for the p30 core and p35-8 E1 sequences contained in the 24S subgenomic messenger RNA of RV (Zheng, 1989, infra) in Table 7 revealed that one core sequence SEQ ID NO: 3 was homologous with one E2 sequence SEQ ID NO: 7 as follows:

TABLE 7

COMPARISON OF SEQUENCE HOMOLOGIES BETWEEN
p30 AND p38 IN THE RUBELLA VIRUS GENOME

| ORIGIN | AMINO ACID POSITION | SEQUENCE |
| --- | --- | --- |
| RV (p30) core | 102 | Q—P—Q—P—P—R—M |
| RV (E2) membrane | 313 | P—P—Q—P—P—R—A |

In view of the core/outer membrane cross-reactivity of the RV monoclonal antibodies, it was certain that these antibodies would detect the presence of both p30 core and E2 membrane proteins, therby limiting their use in any diagnostic system which would attempt to define the status of RV infection in the CNS as permissive, or non-permissive, for growth.

However, the significance of the external placement of the internal core sequence in the membrane-associated E2 protein represents an important viral strategy as noted that amino acid changes in the E2 protein of several alphaviruses have been found in Sindbis virus (Davis et al. , 1986, *Proc. Natl. Acad. Sci.* 83; 6771–6775), Ross River virus (Faragher et al., 1988, *Virology* 163:509–526) and Venezuelan equine encephalitis virus (Johnson et al., 2986, *J. Gne. Virol.* 67:1951–1960), to be implicated in the modulation of viral virulence.

EXAMPLE 2

The Use of RV1 Mab to Detect and Define Homologous Meningitis-Specific Antigenic sequences In the course of RV1 Mab Characterization, it was observed that the RV1 Mab cross-reacted with bacterial antigens in *N. meningitidis, S. Pneumoniae, H. Influenzae, L. monocytogenes* as well as antigens in HIV-1. Immunoblots were performed as previously described using bacterial antigens and HIV-1 antigens and RV-1Mab.

Bacterial Strains and Culture Conditions

The bacterial strains were obtained from the American Type Culture Collection (ATCC), Washington, D.C. (*Neisseria meningitidis and Streptococcus pneumoniae*) and from the Caribbean Epidemiology Centre (CAREC), Port of Spain, Trinidad (*Streptococcus pneumoniae*). All strains were grown on chocolate agar overnight at 37° C. in an atmosphere containing 5% C02. Cultures were stored in brain heart infusion broth containing 20% glycerol at −7° C.

Antigert Preparation for PAGE and Immunoblotting

Antigens present in the outer membrane protein fraction of *Neisseria meningitidis* were prepared using lithium chloride as previously described by Johnston et al., 1976, *J. Exp. Med.* 143: 741–758 incorporated herein by reference. Whole cells were suspended in lithium chloride buffer (200 mM lithium chloride, 100 mM lithium acetate, 10 mM EDTA, pH 6.0), transferred to a 250 ml erleluneyer flask containing 3–5 mm glass beads and shaken at 300 rpm in a G24 Environmental incubator shaker for 2 hours at 45° C. The suspension was centrifuged at 8,000 rpm for 20 minutes using a Sorvall SS034 fixed angle rotor with R max=10.70 cm. Collected supernatant was transferred to a rigid wall polycarbonate tube and centrifuged at 35,000 rpm for 2 hr at 10° C. using a 50.2 Beckman rotor. The supernatant was discarded and pellet resuspended in 1 ml of phosphate buffered saline (PBS). The protein content was determined by the Lowry method.

Sonicated antigen preparations of *S. pneumoniae* and *H. influenzae* were prepared using the following procedure. Approximately $10^{11}$ bacteria were suspended in 5 ml PBS and heat-killed for 20 min at 56° C. Using a Branso 350 Sonifier Cell disruper (Branson Cleaning Equipment Co.) cells were sonicated 3 times, with a 50% pulse setting, for 5 minutes each time. The sample was kept at 4° C. with ice throughout. The suspensions were then centrifuged for 20 min at 25,000 rpm, using a Beckman 70 Ti.1 rotor at 10° C. The protein concentration of the resulting supernatant was determined using the Lowrey protein assay.

HIV-1 antigen was purchased from ABI (Advanced Biotechnologies, Inc., Columbia, Md). Antigen was contained in viral lysate with specifications given in catalog number 10-119-000 with Lot number 54–040 containing a particle count of $1.09 \times 10^{10}$ vp/ml active virus. The preparation was treated with Triton X-100 added to a final concentration of 1%, and heated to 56° C. for one hour with mixing. The final protein concentration of lysate was 0.78 mg/ml. Each lane for PAGE contained 10 μg of antigen.

PAGE and Immunoblotting procedures.

PAGE was carried out as previously described using 15 μl samples of bacterial antigen, containing 5 μg protein per well. Immunoblots were performed on the transferred antigens using RV1 Mab in tissue culture supernatants as previously described.

The results of immunoblots of bacterial antigen using RV1 Mab are contained in FIG. 12. The RIV Mab clearly detected cross-reacting epitopes in *N. Meningitidis, influenzae, S. pneumoniae* and eliminated all of these bands, indicating that the antigens detected with the RV Mab are protein in nature. Control Streptococcus A and *M.tuberculosis* (p60) antigen preparations were negative using the RV1 Mab.

The results of immunoblots of HIV antigens using RV1 Mab are contained in FIG. 13. The RV1 Mab clearly detected two membrane protein antigens indicating that HIV employs a strategy identical to that of RV which places a portion of the inner core protein on the outside of the virion.

Since the likely sequences of the corresponding RV1 Mab antigens are QPQPPRM SEQ ID NO: 3 and PPQPPCA SEQ ID NO: 7 in the core and E2 proteins, respectively, a search was undertaken to find similar, cross reacting sequences in the available bacterial and HIV sequences, with results the data presented in TABLE 4.

FIG. 12 illustrates a cross-reactivity, with the RV1 Mab detecting a major band of apporximately 26–28,000 daltons and 2 minor bands at approximately 45,000 daltons. An outer membrane protein with a molecular weight of about 28,000, expressed on the cell surface, and existing as a lipoprotein in association with the outer membrane-cell wall complex of *H. influenzae* has been identified and designated Protein E. It is capable of eliciting a bactericidal immune response against non-typable *Influenzae* and is highly conserved among *H.influenzae* strains. Protein E has been sequence ( Green and Z lotnick, infra ) and the sequences listed in Table 4 (SEQ ID NOS 3, 5, 7, 10, 13, 16, 19, 22, 25, 28, 30, 32, 34, 37 and 40) are closely homologous to the membrane and core sequences of RV shown in that table.

FIG. 12 also illustrates that the RV1 Mab detected one band at approximately 60,000 daltons with *L.monocytogenes*. All virulent *L.monocytogenes* stains secrete as SH-activated cytolysin called listeriolysin (Kuhn & Goebel, 1988, *Infect. Immun.* 56:79–82). This protein, termed p60, is an essential virulence factor as nonhemolytic mutants have reduced rates of survival in the mouse infection model (Galliard, et al., 1986, *Infect. Immun.* 52:50–55) and in mouse peritoneal macrophages (Kuhn & Goebel, infra). The sequence of the p60 has been determined (Kohler, et al., 1990, *Infec. Immun.* 58:1943–1950) and the sequences identified at the positions listed in Table 4 (SEQ ID NOS 3, 5, 7, 10, 13, 16, 19, 22, 25, 28, 30, 32, 34, 37 ,and 40);are closely homologous to the RV core and membrane sequence.

Figure 13:
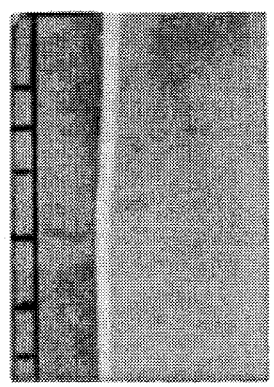

Finally, FIG. 13 illustrates that the RV Mab detected two bands at approximately 24,000 (p24) and 61,000 (p61) daltons. The p24 has been shown to be a major core protein and p61 a transmembrane protein in the HIV virion, and the complete nuceotide sequence of the HIV1 genome is available (Ratner et al., 1985, *Nature* 313:277–280). A number of septapeptide sequences were identified which are closely homologous to the RV core and membrane sequences, and these sequences are listed in Table 4 (SEQ ID NOS 3, 5, 7, 10, 13, 16, 19, 22, 25, 28, 30, 32, 34, 37 and 40).

We claim:

1. A peptide having the formula aXb, wherein a is linked to X by a simple peptide bond and b is linked to X by a simple peptide bond, wherein X is a Meningitis Related Homologous Antigenic Sequence contained in the amino acid sequence of a protein or peptide found in a bacterium or virus that is an etiologic agent of meningitis, said protein or peptide is a chemokine involved in cell chemotaxis, and wherein said Meningitis Related Homologous Antigenic Sequence is at least 7 sequential amino acids and conservative substitutions or modifications thereof selected from the group consisting of:

(i) the amino acid sequence of the Structural Polyprotein of a strain of Rubella virus that corresponds to $AA_{102}$–$AA_{108}$ of said protein of the M33 strain of Rubella virus as set forth in SEQ ID NO:1;

(ii) the amino acid sequence of the Structural Polyprotein of a strain of Rubella virus that corresponds to $AA_{89}$–$AA_{95}$ of said protein of the M33 strain of Rubella virus as set forth in SEQ ID NO:1;

(iii) the amino acid sequence of the Structural Polyprotein of a strain of Rubella virus that corresponds to $AA_{313}$–$AA_{319}$ of said protein of the M33 strain of Rubella virus as set forth in SEQ ID NO:1;

(iv) the amino acid sequence of the Structural Polyprotein of a strain of Rubella virus that corresponds to $AA_{103}$–$AA_{109}$ of said protein of the Therien strain of Rubella virus as set forth in SEQ ID NO:8;

(v) the amino acid sequence of the Structural Polyprotein of a strain of Rubella virus that corresponds to $AA_{90}$–$AA_{96}$ of said protein of the Therien strain of Rubella virus as set forth in SEQ ID NO:8;

(vi) the amino acid sequence of the Structural Polyprotein of a strain of Rubella virus that corresponds to $AA_{314}$–$AA_{320}$ of said protein of the Thorion strain of Rubella virus as set forth in SEQ ID NO:8;

(vii) the amino acid sequence of the Gag Polyprotein of an isolate of the HIV-1 that corresponds to $AA_{145}$–$AA_{151}$ of the Gag Polyprotein of the LV isolate of HIV-1 as set forth in SEQ ID NO:11;

(viii) the amino acid sequence of the Envelope Polypretain Precursor of an isolate of the HIV-1 that corresponds to $AA_{655}$ to $AA_{661}$ of the Envelope Polypretain Precursor of the LAV-1a isolate of HIV-1 as set forth in SEQ ID NO:14;

(ix) the amine acid sequence that corresponds to $AA_{99}$–$AA_{105}$ of the Lipoprotein E Precursor of *Haemophilus influenzae* as set forth in SEQ ID NO:17;

(x) the amine acid sequence that corresponds to $AA_1$ to $AA_5$ of the Opacity-Related Protein POPM3 of *Neisseria meningitidis* as set forth in SEQ ID NO:20;

(xi) the amine acid sequence that corresponds to $A_{123}$ to $AA_{129}$ of the Pneumococcal Surface Protein A of *Streptococcus pneumoniae* as set forth in SEQ ID NO:23;

(xii) the amine acid sequence that corresponds to $AA_{151}$–$AA_{157}$ of the Protein P60 Precursor of *Listeria monocytogenes* as set forth in SEQ ID NO:26;

(xiii) the amine acid sequence that corresponds to $AA_{181}$–$AA_{187}$ of the Protein P60 Precursor of *Listeria monocytogenes* as set forth in SEQ ID NO:26;

(xiv) the amine acid sequence that corresponds to $AA_{249}$–$AA_{255}$ of the Protein P60 Precursor of Listeria monocytogenes as set forth in SEQ ID NO:26;

(xv) the amine acid sequence that corresponds to $A_{292}$–$AA_{298}$ of the Protein P60 Precursor of *Listeria monocytogenes* as set forth in SEQ ID NO:26;

(xvi) the amine acid sequence of a variant of the chemokine human Monocyte Chemoattractant Factor hMCP-1, that corresponds to $AA_{93}$–$AA_{99}$ of hMCP-1 as set forth in SEQ ID NO:35; and (xvii) the amino acid sequence of the chemokine hMCP-3, that corresponds to $AA_{61}$–$AA_{67}$ of hMCP-3 as set forth in SEQ ID NO: 38, wherein
   a is an amino terminus which comprises
      (i) one to eight sequential amino acids from the native amino acid sequence of the protein immediately N-terminal to said X, or conservative substitutions in or modifications of said native amino acid sequence or
      (ii) a substituent effective to facilitate coupling of the peptide to another moiety and wherein
   b is a carboxy terminus which comprises
      (i) one to eight sequential amino acids from the native amino acid sequence of the protein immediately C-terminal to said X or conservative substitutions in or modifications of said native amino acid sequence or
      (ii) a substituent effective to facilitate coupling of the peptide to another moiety.

2. An article of manufacture for use in an immunoassay capable of detecting antibodies against meningitis-causing etiologic organisms or a chemokine involved in cell chemotaxis comprising a solid support and, having bound to said support, a peptide having a formula aXb according to claim 1.

* * * * *

SEQUENCE LISTING ( 1 ) GENERAL INFORMATION:

( i i i ) NUMBER OF SEQUENCES: 40

( 2 ) INFORMATION FOR SEQ ID NO:1:

( i ) SEQUENCE CHARACTERISTICS:
( A ) LENGTH: 992 amino acids
( B ) TYPE: amino acid
( C ) STRANDEDNESS:
( D ) TOPOLOGY: unknown ( x i ) SEQUENCE DESCRIPTION: SEQ ID NO:1:

| | | | | | | | | | | | | | | | |
|---|---|---|---|---|---|---|---|---|---|---|---|---|---|---|---|
| Met | Ala | Ser | Thr | Thr | Pro | Ile | Thr | Met | Glu | Asp | Leu | Gln | Lys | Ala | Leu |
| 1 | | | | 5 | | | | | 10 | | | | | 15 | |
| Glu | Ala | Gln | Ser | Arg | Ala | Leu | Arg | Ala | Gly | Leu | Ala | Ala | Gly | Ala | Ser |
| | | | 20 | | | | | 25 | | | | | 30 | | |
| Gln | Ser | Arg | Arg | Pro | Arg | Pro | Pro | Arg | His | Ala | Arg | Leu | Gln | His | Leu |
| | | 35 | | | | | 40 | | | | | 45 | | | |
| Pro | Glu | Met | Thr | Pro | Ala | Val | Thr | Pro | Glu | Gly | Pro | Ala | Pro | Pro | Arg |
| | 50 | | | | | 55 | | | | | 60 | | | | |
| Thr | Gly | Ala | Trp | Gln | Arg | Lys | Asp | Trp | Ser | Arg | Ala | Pro | Pro | Pro | Pro |
| 65 | | | | | 70 | | | | | 75 | | | | | 80 |
| Glu | Glu | Arg | Gln | Glu | Ser | Arg | Ser | Gln | Thr | Pro | Ala | Pro | Lys | Pro | Ser |
| | | | | 85 | | | | | 90 | | | | | 95 | |
| Arg | Ala | Pro | Pro | Gln | Gln | Pro | Gln | Pro | Pro | Arg | Met | Gln | Thr | Gly | Arg |
| | | | 100 | | | | | 105 | | | | | 110 | | |
| Gly | Gly | Ser | Ala | Pro | Arg | Pro | Glu | Leu | Gly | Pro | Pro | Thr | Asn | Pro | Phe |
| | | 115 | | | | | 120 | | | | | 125 | | | |
| Gln | Ala | Ala | Val | Ala | Arg | Gly | Leu | Arg | Pro | Pro | Leu | His | Asp | Pro | Asp |
| | 130 | | | | | 135 | | | | | 140 | | | | |
| Thr | Glu | Ala | Pro | Thr | Glu | Ala | Cys | Val | Thr | Ser | Trp | Leu | Trp | Ser | Glu |
| 145 | | | | | 150 | | | | | 155 | | | | | 160 |
| Gly | Glu | Gly | Ala | Val | Phe | Tyr | Arg | Val | Asp | Leu | His | Phe | Ile | Asn | Leu |
| | | | | 165 | | | | | 170 | | | | | 175 | |
| Gly | Thr | Pro | Pro | Leu | Asp | Glu | Asp | Gly | Arg | Trp | Asp | Pro | Ala | Leu | Met |
| | | | 180 | | | | | 185 | | | | | 190 | | |
| Tyr | Asn | Pro | Cys | Gly | Pro | Glu | Pro | Pro | Ala | His | Val | Val | Arg | Ala | Tyr |
| | | 195 | | | | | 200 | | | | | 205 | | | |
| Asn | Gln | Pro | Ala | Gly | Asp | Val | Arg | Gly | Val | Trp | Gly | Lys | Gly | Glu | Arg |
| | 210 | | | | | 215 | | | | | 220 | | | | |
| Thr | Tyr | Ala | Glu | Gln | Asp | Phe | Arg | Val | Gly | Gly | Thr | Arg | Trp | His | Arg |
| 225 | | | | | 230 | | | | | 235 | | | | | 240 |
| Leu | Leu | Arg | Met | Pro | Val | Arg | Gly | Leu | Asp | Gly | Asp | Thr | Ala | Pro | Leu |
| | | | | 245 | | | | | 250 | | | | | 255 | |
| Pro | Pro | His | Thr | Thr | Glu | Arg | Ile | Glu | Thr | Arg | Ser | Ala | Arg | His | Pro |
| | | | 260 | | | | | 265 | | | | | 270 | | |
| Trp | Arg | Ile | Arg | Phe | Gly | Ala | Pro | Gln | Ala | Phe | Leu | Ala | Gly | Leu | Leu |
| | | 275 | | | | | 280 | | | | | 285 | | | |

```
Leu  Ala  Ala  Val  Ala  Val  Gly  Thr  Ala  Arg  Ala  Gly  Leu  Gln  Pro  Arg
     290                 295                 300

Ala  Asp  Met  Ala  Ala  Pro  Met  Pro  Pro  Gln  Pro  Pro  Arg  Ala  His
305                      310                 315                      320

Gly  Gln  His  Tyr  Gly  His  His  His  Gln  Leu  Pro  Phe  Leu  Gly  His
                    325                 330                           335

Asp  Gly  His  His  Gly  Gly  Thr  Leu  Arg  Val  Gly  Gln  His  His  Arg  Asn
               340                      345                      350

Ala  Ser  Asp  Val  Leu  Pro  Gly  His  Trp  Leu  Gln  Gly  Gly  Trp  Gly  Cys
          355                      360                      365

Tyr  Asn  Leu  Ser  Asp  Trp  His  Gln  Gly  Thr  His  Val  Cys  His  Thr  Lys
     370                      375                 380

His  Met  Asp  Phe  Trp  Cys  Val  Glu  His  Asp  Arg  Pro  Pro  Pro  Ala  Thr
385                      390                 395                           400

Pro  Thr  Ser  Leu  Thr  Thr  Ala  Ala  Asn  Tyr  Ile  Ala  Ala  Ala  Thr  Pro
               405                      410                      415

Ala  Thr  Ala  Pro  Pro  Pro  Cys  His  Ala  Gly  Leu  Asn  Asp  Ser  Cys  Gly
               420                 425                      430

Gly  Phe  Leu  Ser  Gly  Cys  Gly  Pro  Met  Arg  Leu  Pro  Thr  Ala  Leu  Thr
          435                      440                 445

Pro  Gly  Ala  Val  Gly  Asp  Leu  Arg  Ala  Val  His  His  Arg  Pro  Val  Pro
     450                      455                 460

Ala  Tyr  Pro  Val  Cys  Cys  Ala  Met  Arg  Trp  Gly  Leu  Pro  Pro  Trp  Glu
465                      470                 475                           480

Leu  Val  Ile  Leu  Thr  Ala  Arg  Pro  Glu  Asp  Gly  Trp  Thr  Cys  Arg  Gly
               485                      490                      495

Val  Pro  Ala  His  Pro  Gly  Thr  Arg  Cys  Pro  Glu  Leu  Val  Ser  Pro  Met
               500                 505                      510

Gly  Arg  Ala  Thr  Cys  Ser  Pro  Ala  Ser  Ala  Leu  Trp  Leu  Ala  Thr  Ala
          515                      520                 525

Asn  Ala  Leu  Ser  Leu  Asp  His  Ala  Phe  Ala  Ala  Phe  Val  Leu  Leu  Val
     530                      535                 540

Pro  Trp  Val  Leu  Ile  Phe  Met  Val  Cys  Arg  Arg  Ala  Cys  Arg  Arg  Pro
545                      550                      555                      560

Ala  Pro  Pro  Pro  Pro  Ser  Pro  Gln  Ser  Ser  Cys  Arg  Gly  Thr  Thr  Pro
                    565                 570                      575

Pro  Ala  Tyr  Gly  Glu  Glu  Ala  Phe  Thr  Tyr  Leu  Cys  Thr  Ala  Pro  Gly
               580                      585                 590

Cys  Ala  Thr  Gln  Thr  Pro  Val  Pro  Val  Arg  Leu  Ala  Gly  Val  Gly  Phe
          595                      600                 605

Glu  Ser  Lys  Ile  Val  Asp  Gly  Gly  Cys  Phe  Ala  Pro  Trp  Asp  Leu  Glu
     610                      615                 620

Ala  Thr  Gly  Ala  Cys  Ile  Cys  Glu  Ile  Pro  Thr  Asp  Val  Ser  Cys  Glu
625                      630                 635                           640

Gly  Leu  Gly  Ala  Trp  Val  Pro  Thr  Ala  Pro  Cys  Ala  Arg  Ile  Trp  Asn
               645                      650                      655

Gly  Thr  Gln  Arg  Ala  Cys  Thr  Phe  Trp  Ala  Val  Asn  Ala  Tyr  Ser  Ser
               660                      665                 670

Gly  Gly  Tyr  Ala  Gln  Leu  Ala  Ser  Tyr  Phe  Asn  Pro  Gly  Gly  Ser  Tyr
          675                      680                 685

Tyr  Lys  Gln  Tyr  His  Pro  Thr  Ala  Cys  Glu  Val  Glu  Pro  Ala  Phe  Gly
     690                      695                 700

His  Ser  Asp  Ala  Ala  Cys  Trp  Gly  Phe  Pro  Thr  Asp  Thr  Val  Met  Ser
```

|     |     |     |     |     |     |     |     |     |     |     |     |     |     |     |     |
|-----|-----|-----|-----|-----|-----|-----|-----|-----|-----|-----|-----|-----|-----|-----|-----|
| 705 |     |     |     |     |     | 710 |     |     |     |     | 715 |     |     |     | 720 |
| Val | Phe | Ala | Leu | Ala | Ser | Tyr | Val | Gln | His | Pro | His | Lys | Thr | Val | Arg |
|     |     |     |     | 725 |     |     |     |     | 730 |     |     |     |     | 735 |     |
| Val | Lys | Phe | His | Thr | Glu | Thr | Arg | Thr | Val | Trp | Gln | Leu | Ser | Val | Ala |
|     |     |     | 740 |     |     |     |     | 745 |     |     |     |     | 750 |     |     |
| Gly | Val | Ser | Cys | Asn | Val | Thr | Thr | Glu | His | Pro | Phe | Cys | Asn | Thr | Pro |
|     |     | 755 |     |     |     |     | 760 |     |     |     |     | 765 |     |     |     |
| His | Gly | Gln | Leu | Glu | Val | Gln | Val | Pro | Pro | Asp | Pro | Gly | Asp | Leu | Val |
|     | 770 |     |     |     |     | 775 |     |     |     |     | 780 |     |     |     |     |
| Glu | Tyr | Ile | Met | Asn | Tyr | Thr | Gly | Asn | Gln | Gln | Ser | Arg | Trp | Gly | Leu |
| 785 |     |     |     |     | 790 |     |     |     |     | 795 |     |     |     |     | 800 |
| Gly | Ser | Pro | Asn | Cys | His | Gly | Pro | Asp | Trp | Ala | Ser | Pro | Val | Cys | Gln |
|     |     |     |     | 805 |     |     |     |     | 810 |     |     |     |     | 815 |     |
| Arg | His | Ser | Pro | Asp | Cys | Ser | Arg | Leu | Val | Gly | Ala | Thr | Pro | Glu | Arg |
|     |     |     | 820 |     |     |     |     | 825 |     |     |     |     | 830 |     |     |
| Pro | Arg | Leu | Arg | Leu | Val | Asp | Ala | Asp | Asp | Pro | Leu | Leu | Arg | Thr | Ala |
|     |     | 835 |     |     |     |     | 840 |     |     |     |     | 845 |     |     |     |
| Pro | Gly | Pro | Gly | Glu | Val | Trp | Val | Thr | Pro | Val | Ile | Gly | Ser | Gln | Ala |
|     | 850 |     |     |     |     | 855 |     |     |     |     | 860 |     |     |     |     |
| Arg | Lys | Cys | Gly | Leu | His | Ile | Arg | Ala | Gly | Pro | Tyr | Gly | His | Ala | Thr |
| 865 |     |     |     |     | 870 |     |     |     |     | 875 |     |     |     |     | 880 |
| Val | Glu | Met | Pro | Glu | Trp | Ile | His | Ala | His | Thr | Thr | Ser | Asp | Pro | Trp |
|     |     |     |     | 885 |     |     |     |     | 890 |     |     |     |     | 895 |     |
| His | Pro | Pro | Gly | Pro | Leu | Gly | Leu | Lys | Phe | Lys | Thr | Val | Arg | Pro | Val |
|     |     |     | 900 |     |     |     |     | 905 |     |     |     |     | 910 |     |     |
| Ala | Leu | Pro | Arg | Ala | Leu | Ala | Pro | Pro | Arg | Asn | Val | Arg | Val | Thr | Gly |
|     |     | 915 |     |     |     |     | 920 |     |     |     |     | 925 |     |     |     |
| Cys | Tyr | Gln | Cys | Gly | Thr | Pro | Ala | Leu | Val | Glu | Gly | Leu | Ala | Pro | Gly |
|     | 930 |     |     |     |     | 935 |     |     |     |     | 940 |     |     |     |     |
| Gly | Gly | Asn | Cys | His | Leu | Thr | Val | Asn | Gly | Glu | Asp | Val | Gly | Ala | Phe |
| 945 |     |     |     |     | 950 |     |     |     |     | 955 |     |     |     |     | 960 |
| Pro | Pro | Gly | Lys | Phe | Val | Thr | Ala | Ala | Leu | Leu | Asn | Thr | Pro | Pro | Pro |
|     |     |     |     | 965 |     |     |     |     | 970 |     |     |     |     | 975 |     |
| Tyr | Gln | Val | Ser | Cys | Gly | Gly | Glu | Ser | Asp | Arg | Ala | Ser | Ala | Gly | His |
|     |     |     | 980 |     |     |     |     | 985 |     |     |     |     | 990 |     |     |

( 2 ) INFORMATION FOR SEQ ID NO:2:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: unknown ( x i ) SEQUENCE DESCRIPTION: SEQ ID NO:2:

|     |     |     |     |     |     |     |     |     |     |     |     |     |     |     |
|-----|-----|-----|-----|-----|-----|-----|-----|-----|-----|-----|-----|-----|-----|-----|
| Pro | Ser | Arg | Ala | Pro | Pro | Gln | Gln | Pro | Gln | Pro | Pro | Arg | Met | Gln | Thr |
| 1   |     |     |     | 5   |     |     |     |     | 10  |     |     |     |     | 15  |     |
| Gly | Arg | Gly | Gly | Ser |     |     |     |     |     |     |     |     |     |     |     |
|     |     |     |     | 20  |     |     |     |     |     |     |     |     |     |     |     |

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: unknown ( x i ) SEQUENCE DESCRIPTION: SEQ ID NO:3:

```
        Gln  Pro  Gln  Pro  Pro  Arg  Met
        1                 5
```

( 2 ) INFORMATION FOR SEQ ID NO:4:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: unknown ( x i ) SEQUENCE DESCRIPTION: SEQ ID NO:4:

```
        Glu  Arg  Gln  Glu  Ser  Arg  Ser  Gln  Thr  Pro  Ala  Pro  Lys  Pro  Ser  Arg
        1                 5                           10                          15

Ala  Pro  Pro  Gln  Gln
                      20
```

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: unknown ( x i ) SEQUENCE DESCRIPTION: SEQ ID NO:5:

```
        Gln  Thr  Pro  Ala  Pro  Lys  Pro
        1                 5
```

( 2 ) INFORMATION FOR SEQ ID NO:6:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: unknown ( x i ) SEQUENCE DESCRIPTION: SEQ ID NO:6:

```
        Asp  Met  Ala  Ala  Pro  Pro  Met  Pro  Pro  Gln  Pro  Pro  Arg  Ala  His  Gly
        1                 5                           10                          15

Gln  His  Tyr  Gly  His
                      20
```

( 2 ) INFORMATION FOR SEQ ID NO:7:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: unknown ( x i ) SEQUENCE DESCRIPTION: SEQ ID NO:7:

```
        Pro  Pro  Gln  Pro  Pro  Arg  Ala
        1                 5
```

( 2 ) INFORMATION FOR SEQ ID NO:8:

( i ) SEQUENCE CHARACTERISTICS:
        ( A ) LENGTH: 1063 amino acids
        ( B ) TYPE: amino acid
        ( C ) STRANDEDNESS:
        ( D ) TOPOLOGY: unknown ( x i ) SEQUENCE DESCRIPTION: SEQ ID NO:8:

```
        Met  Ala  Ser  Thr  Thr  Pro  Ile  Thr  Met  Glu  Asp  Leu  Gln  Lys  Ala  Leu
        1                 5                           10                          15
```

```
Glu  Ala  Gln  Ser  Arg  Ala  Leu  Arg  Ala  Glu  Leu  Ala  Ala  Gly  Ala  Ser
               20                  25                  30

Gln  Ser  Arg  Arg  Pro  Arg  Pro  Pro  Arg  Gln  Arg  Asp  Ser  Ser  Thr  Ser
          35                  40                  45

Gly  Asp  Asp  Ser  Gly  Arg  Asp  Ser  Gly  Gly  Pro  Arg  Arg  Arg  Gly
     50                       55                  60

Asn  Arg  Gly  Arg  Gly  Gln  Arg  Arg  Asp  Trp  Ser  Arg  Ala  Pro  Pro  Pro
65                       70                  75                            80

Pro  Glu  Glu  Arg  Gln  Glu  Ser  Arg  Ser  Gln  Thr  Pro  Ala  Pro  Lys  Pro
               85                       90                       95

Ser  Arg  Ala  Pro  Pro  Gln  Gln  Pro  Gln  Pro  Pro  Arg  Met  Gln  Thr  Gly
               100                 105                      110

Arg  Gly  Gly  Ser  Ala  Pro  Arg  Pro  Glu  Leu  Gly  Pro  Pro  Thr  Asn  Pro
          115                 120                 125

Phe  Gln  Ala  Ala  Val  Ala  Arg  Gly  Leu  Arg  Pro  Pro  Leu  His  Asp  Pro
     130                 135                      140

Asp  Thr  Glu  Ala  Pro  Thr  Glu  Ala  Cys  Val  Thr  Ser  Trp  Leu  Trp  Ser
145                      150                 155                           160

Glu  Gly  Gln  Gly  Ala  Val  Phe  Tyr  Arg  Val  Asp  Leu  His  Phe  Thr  Asn
               165                 170                      175

Leu  Gly  Thr  Pro  Pro  Leu  Asp  Glu  Asp  Gly  Arg  Trp  Asp  Pro  Ala  Leu
          180                 185                      190

Met  Tyr  Asn  Pro  Cys  Gly  Pro  Glu  Pro  Pro  Ala  His  Val  Val  Arg  Ala
          195                 200                 205

Tyr  Asn  Gln  Pro  Ala  Gly  Asp  Val  Arg  Gly  Val  Trp  Gly  Lys  Gly  Glu
     210                 215                      220

Arg  Thr  Tyr  Ala  Glu  Gln  Asp  Phe  Arg  Val  Gly  Gly  Thr  Arg  Trp  His
225                      230                 235                           240

Arg  Leu  Leu  Arg  Met  Pro  Val  Arg  Gly  Leu  Asp  Gly  Asp  Ser  Ala  Pro
               245                 250                      255

Leu  Pro  Pro  His  Thr  Thr  Glu  Arg  Ile  Glu  Thr  Arg  Ser  Ala  Arg  His
               260                 265                      270

Pro  Trp  Arg  Ile  Arg  Phe  Gly  Ala  Pro  Gln  Ala  Phe  Leu  Ala  Gly  Leu
          275                 280                      285

Leu  Leu  Ala  Thr  Val  Ala  Val  Gly  Thr  Ala  Arg  Ala  Gly  Leu  Gln  Pro
     290                 295                      300

Arg  Ala  Asp  Met  Ala  Ala  Pro  Pro  Thr  Leu  Pro  Gln  Pro  Pro  Cys  Ala
305                      310                 315                           320

His  Gly  Gln  His  Tyr  Gly  His  His  His  Gln  Leu  Pro  Phe  Leu  Gly
                    325                 330                      335

His  Asp  Gly  His  His  Gly  Gly  Thr  Leu  Arg  Val  Gly  Gln  His  Tyr  Arg
               340                      345                 350

Asn  Ala  Ser  Asp  Val  Leu  Pro  Gly  His  Trp  Leu  Gln  Gly  Gly  Trp  Gly
          355                 360                      365

Cys  Tyr  Asn  Leu  Ser  Asp  Trp  His  Gln  Gly  Thr  His  Val  Cys  His  Thr
     370                      375                 380

Lys  His  Met  Asp  Phe  Trp  Cys  Val  Glu  His  Ala  Arg  Pro  Pro  Pro  Ala
385                      390                 395                           400

Thr  Pro  Thr  Pro  Leu  Thr  Thr  Ala  Ala  Asn  Ser  Thr  Thr  Ala  Ala  Thr
               405                 410                      415

Pro  Ala  Thr  Ala  Pro  Ala  Pro  Cys  His  Ala  Gly  Leu  Asn  Asp  Ser  Cys
               420                 425                      430

Gly  Gly  Phe  Leu  Ser  Gly  Cys  Gly  Pro  Met  Arg  Leu  Arg  His  Gly  Ala
          435                 440                      445
```

```
Asp  Thr  Arg  Cys  Gly  Arg  Leu  Ile  Cys  Gly  Leu  Ser  Thr  Thr  Ala  Gln
     450                      455                      460

Tyr  Pro  Pro  Thr  Arg  Phe  Gly  Cys  Ala  Met  Arg  Trp  Gly  Leu  Pro  Pro
465                      470                      475                      480

Trp  Glu  Leu  Val  Val  Leu  Thr  Ala  Arg  Pro  Glu  Asp  Gly  Trp  Thr  Cys
               485                      490                                495

Arg  Gly  Val  Pro  Ala  His  Pro  Gly  Ala  Arg  Cys  Pro  Glu  Leu  Val  Ser
               500                      505                      510

Pro  Met  Gly  Arg  Ala  Thr  Cys  Ser  Pro  Ala  Ser  Ala  Leu  Trp  Leu  Ala
          515                 520                      525

Thr  Ala  Asn  Ala  Leu  Ser  Leu  Asp  His  Ala  Leu  Ala  Ala  Phe  Val  Leu
     530                 535                           540

Ser  Val  Pro  Trp  Val  Leu  Ile  Phe  Met  Val  Cys  Arg  Arg  Ala  Cys  Arg
545                      550                      555                      560

Arg  Arg  Gly  Ala  Ala  Ala  Ala  Leu  Thr  Ala  Val  Val  Leu  Gln  Gly  Tyr
               565                      570                      575

Asn  Pro  Pro  Ala  Tyr  Gly  Glu  Glu  Ala  Phe  Thr  Tyr  Leu  Cys  Thr  Ala
               580                      585                      590

Pro  Gly  Cys  Ala  Thr  Gln  Ala  Pro  Val  Pro  Val  Arg  Leu  Ala  Gly  Val
          595                      600                      605

Arg  Phe  Glu  Ser  Lys  Ile  Val  Asp  Gly  Gly  Cys  Phe  Ala  Pro  Trp  Asp
     610                      615                      620

Leu  Glu  Ala  Thr  Gly  Ala  Cys  Ile  Cys  Glu  Ile  Pro  Thr  Asp  Val  Ser
625                      630                      635                      640

Cys  Glu  Gly  Leu  Gly  Ala  Trp  Val  Pro  Ala  Ala  Pro  Cys  Ala  Arg  Ile
               645                      650                      655

Trp  Asn  Gly  Thr  Gln  Arg  Ala  Cys  Thr  Phe  Trp  Ala  Val  Asn  Ala  Tyr
               660                      665                      670

Ser  Ser  Gly  Gly  Tyr  Ala  Gln  Leu  Ala  Ser  Tyr  Phe  Asn  Pro  Gly  Gly
          675                      680                      685

Ser  Tyr  Tyr  Lys  Gln  Tyr  His  Pro  Thr  Ala  Cys  Glu  Val  Glu  Pro  Ala
     690                      695                      700

Phe  Gly  His  Ser  Asp  Ala  Ala  Cys  Trp  Gly  Phe  Pro  Thr  Asp  Thr  Val
705                      710                      715                      720

Met  Ser  Val  Phe  Ala  Leu  Ala  Ser  Tyr  Val  Gln  His  Pro  His  Lys  Thr
               725                      730                      735

Val  Arg  Val  Lys  Phe  His  Thr  Glu  Thr  Arg  Thr  Val  Trp  Gln  Leu  Ser
               740                      745                      750

Val  Ala  Gly  Val  Ser  Cys  Asn  Val  Thr  Thr  Glu  His  Pro  Phe  Cys  Asn
               755                      760                      765

Thr  Pro  His  Gly  Gln  Leu  Glu  Val  Gln  Val  Pro  Pro  Asp  Pro  Gly  Asp
     770                      775                      780

Leu  Val  Glu  Tyr  Ile  Met  Asn  Tyr  Thr  Gly  Asn  Gln  Gln  Ser  Arg  Trp
785                      790                      795                      800

Gly  Leu  Gly  Ser  Pro  Asn  Cys  His  Gly  Pro  Asp  Trp  Ala  Ser  Pro  Val
               805                      810                      815

Cys  Gln  Arg  His  Ser  Pro  Asp  Cys  Ser  Arg  Leu  Val  Gly  Ala  Thr  Pro
               820                      825                      830

Glu  Arg  Pro  Arg  Leu  Arg  Leu  Val  Asp  Ala  Asp  Pro  Leu  Leu  Arg
          835                      840                      845

Thr  Ala  Pro  Gly  Pro  Gly  Glu  Val  Trp  Val  Thr  Pro  Val  Ile  Gly  Ser
     850                      855                      860

Gln  Ala  Arg  Lys  Cys  Gly  Leu  His  Ile  Arg  Ala  Gly  Pro  Tyr  Gly  His
```

```
865                      870                      875                      880
Ala Thr Val Glu Met Pro Glu Trp Ile His Ala His Thr Thr Ser Asp
                885                      890                  895
Pro Trp His Pro Pro Gly Pro Leu Gly Leu Lys Phe Lys Thr Val Arg
            900                  905                  910
Pro Val Ala Leu Pro Arg Thr Leu Ala Pro Pro Arg Asn Val Arg Val
            915                  920                  925
Thr Gly Cys Tyr Gln Cys Gly Thr Pro Ala Leu Val Glu Gly Leu Ala
        930                  935                  940
Pro Gly Gly Gly Asn Cys His Leu Thr Val Asn Gly Glu Asp Val Gly
945                      950                      955                      960
Ala Val Pro Pro Gly Lys Phe Val Thr Ala Ala Leu Leu Asn Thr Pro
                965                      970                  975
Pro Pro Tyr Gln Val Ser Cys Gly Gly Glu Ser Asp Arg Ala Ser Ala
            980                  985                  990
Arg Val Ile Asp Pro Ala Ala Gln Ser Phe Thr Gly Val Val Tyr Gly
        995                      1000                 1005
Thr His Thr Thr Ala Val Ser Glu Thr Arg Gln Thr Trp Ala Glu Trp
    1010                     1015                 1020
Ala Ala Ala His Trp Trp Gln Leu Thr Leu Gly Ala Thr Cys Ala Leu
1025                     1030                  1035                     1040
Pro Leu Ala Gly Leu Leu Ala Cys Cys Ala Lys Cys Leu Tyr Tyr Leu
                1045                         1050                 1055
Arg Gly Ala Ile Ala Pro Arg
                1060
```

(2) INFORMATION FOR SEQ ID NO:9:

(i) SEQUENCE CHARACTERISTICS:
(A) LENGTH: 21 amino acids
(B) TYPE: amino acid
(C) STRANDEDNESS:
(D) TOPOLOGY: unknown (xi) SEQUENCE DESCRIPTION: SEQ ID NO:9:

```
Asp Met Ala Ala Pro Pro Thr Leu Pro Gln Pro Pro Arg Ala His Gly
1               5                   10                  15
Gln His Tyr Gly His
            20
```

(2) INFORMATION FOR SEQ ID NO:10:

(i) SEQUENCE CHARACTERISTICS:
(A) LENGTH: 7 amino acids
(B) TYPE: amino acid
(C) STRANDEDNESS:
(D) TOPOLOGY: unknown (xi) SEQUENCE DESCRIPTION: SEQ ID NO:10:

```
Leu Pro Gln Pro Pro Cys Ala
1               5
```

(2) INFORMATION FOR SEQ ID NO:11:

(i) SEQUENCE CHARACTERISTICS:
(A) LENGTH: 478 amino acids
(B) TYPE: amino acid
(C) STRANDEDNESS:
(D) TOPOLOGY: unknown (xi) SEQUENCE DESCRIPTION: SEQ ID NO:11:

-continued

| | | | | | | | | | | | | | | |
|---|---|---|---|---|---|---|---|---|---|---|---|---|---|---|
| Met 1 | Gly | Ala | Arg | Ala 5 | Ser | Val | Leu | Ser | Gly 10 | Gly | Glu | Leu | Asp | Arg Trp 15 |
| Glu | Lys | Ile | Arg 20 | Leu | Arg | Pro | Gly | Lys 25 | Lys | Lys | Tyr | Lys 30 | Leu | Lys |
| His | Ile | Val 35 | Trp | Ala | Ser | Arg | Glu 40 | Leu | Glu | Arg | Phe 45 | Ala | Val | Asn Pro |
| Gly | Leu 50 | Leu | Glu | Thr | Ser | Gly 55 | Cys | Arg | Gln | Ile 60 | Leu | Gly | Gln | Leu |
| Gln 65 | Pro | Ser | Leu | Gln | Thr 70 | Gly | Ser | Glu | Glu 75 | Leu | Arg | Ser | Leu | Tyr Asn 80 |
| Thr | Val | Ala | Thr | Leu 85 | Tyr | Cys | Val | His | Gln 90 | Arg | Ile | Glu | Ile 95 | Lys Asp |
| Thr | Lys | Glu | Ala 100 | Leu | Asp | Lys | Ile | Glu 105 | Glu | Gln | Asn | Lys 110 | Ser | Lys |
| Lys | Lys | Ala 115 | Gln | Gln | Ala | Ala | Ala 120 | Asp | Thr | Gly | His | Ser 125 | Ser | Gln Val |
| Ser | Gln 130 | Asn | Tyr | Pro | Ile | Val 135 | Gln | Asn | Ile | Gln 140 | Gly | Gln | Met | Val His |
| Gln 145 | Ala | Ile | Ser | Pro | Arg 150 | Thr | Leu | Asn | Ala | Trp 155 | Val | Lys | Val | Val Glu 160 |
| Glu | Lys | Ala | Phe | Ser 165 | Pro | Glu | Val | Ile | Pro 170 | Met | Phe | Ser | Ala | Leu 175 Ser |
| Glu | Gly | Ala | Thr 180 | Pro | Gln | Asp | Leu | Asn 185 | Thr | Met | Leu | Asn 190 | Thr | Val Gly |
| Gly | His | Gln 195 | Ala | Ala | Met | Gln 200 | Met | Leu | Lys | Glu | Thr 205 | Ile | Asn | Glu Glu |
| Ala | Ala 210 | Glu | Trp | Asp | Arg | Val 215 | His | Pro | Val | His 220 | Ala | Gly | Pro | Ile Ala |
| Pro 225 | Gly | Gln | Met | Arg | Glu 230 | Pro | Arg | Gly | Ser | Asp 235 | Ile | Ala | Gly | Thr Thr 240 |
| Ser | Thr | Leu | Gln | Glu 245 | Gln | Ile | Gly | Trp | Met 250 | Thr | Asn | Asn | Pro | Pro Ile 255 |
| Pro | Val | Gly | Glu 260 | Ile | Tyr | Lys | Arg | Trp 265 | Ile | Ile | Leu | Gly 270 | Leu | Asn Lys |
| Ile | Val | Arg 275 | Met | Tyr | Ser | Pro | Thr 280 | Ser | Ile | Leu | Asp | Ile 285 | Arg | Gln Gly |
| Pro | Lys 290 | Glu | Pro | Phe | Arg | Asp 295 | Tyr | Val | Asp | Arg | Phe 300 | Tyr | Lys | Thr Leu |
| Arg 305 | Ala | Glu | Gln | Ala | Ser 310 | Gln | Glu | Val | Lys | Asn 315 | Trp | Met | Thr | Glu Thr 320 |
| Leu | Leu | Val | Gln | Asn 325 | Ala | Asn | Pro | Asp | Cys 330 | Lys | Thr | Ile | Leu | Lys 335 Ala |
| Leu | Gly | Pro | Ala 340 | Ala | Thr | Leu | Glu | Glu 345 | Met | Met | Thr | Ala | Cys 350 | Gln Gly |
| Val | Gly | Gly 355 | Pro | Gly | His | Lys | Ala 360 | Arg | Val | Leu | Ala | Glu 365 | Ala | Met Ser |
| Gln | Val 370 | Thr | Asn | Thr | Ala | Thr 375 | Ile | Met | Met | Gln | Arg 380 | Gly | Asn | Phe Arg |
| Asn 385 | Gln | Arg | Lys | Met | Val 390 | Lys | Cys | Phe | Asn | Cys 395 | Gly | Lys | Glu | Gly His 400 |
| Thr | Ala | Arg | Asn | Cys 405 | Arg | Ala | Pro | Arg | Lys 410 | Lys | Gly | Cys | Trp | Lys Cys 415 |
| Gly | Lys | Glu | Gly 420 | His | Gln | Met | Lys | Asp 425 | Cys | Thr | Glu | Arg | Gln 430 | Ala Asn |

```
              Phe   Leu   Gly   Lys   Ile   Cys   Leu   Pro   Thr   Arg   Glu   Gly   Gln   Gly   Ile   Phe
                          435                           440                           445

Phe   Arg   Ala   Asp   Gln   Ser   Gln   Gln   Pro   His   His   Phe   Phe   Arg   Ala   Asp
                          450                           455                           460

Gln   Ser   Gln   Gln   Pro   His   Gln   Lys   Arg   Ala   Ser   Gly   Leu   Gly
                          465                           470                           475
```

( 2 ) INFORMATION FOR SEQ ID NO:12:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: unknown ( x i ) SEQUENCE DESCRIPTION: SEQ ID NO:12:

```
              Ile   Gln   Gly   Gln   Met   Val   His   Gln   Ala   Ile   Ser   Pro   Arg   Thr   Leu   Asn
              1                       5                             10                          15

Ala   Trp   Val   Lys   Val
                                  20
```

( 2 ) INFORMATION FOR SEQ ID NO:13:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: unknown ( x i ) SEQUENCE DESCRIPTION: SEQ ID NO:13:

```
              Gln   Ala   Ile   Ser   Pro   Arg   Thr
              1                       5
```

( 2 ) INFORMATION FOR SEQ ID NO:14:

( i ) SEQUENCE CHARACTERISTICS:
        ( A ) LENGTH: 861 amino acids
        ( B ) TYPE: amino acid
        ( C ) STRANDEDNESS:
        ( D ) TOPOLOGY: unknown ( x i ) SEQUENCE DESCRIPTION: SEQ ID NO:14:

```
              Met   Arg   Val   Lys   Glu   Lys   Tyr   Gln   His   Leu   Trp   Arg   Trp   Gly   Trp   Lys
              1                       5                             10                          15

Trp   Gly   Thr   Met   Leu   Leu   Gly   Ile   Leu   Met   Ile   Cys   Ser   Ala   Thr   Glu
                                  20                          25                          30

Lys   Leu   Trp   Val   Thr   Val   Tyr   Tyr   Gly   Val   Pro   Val   Trp   Lys   Glu   Ala
                            35                          40                          45

Thr   Thr   Thr   Leu   Phe   Cys   Ala   Ser   Asp   Ala   Lys   Ala   Tyr   Asp   Thr   Glu
                            50                          55                          60

Val   His   Asn   Val   Trp   Ala   Thr   His   Ala   Cys   Val   Pro   Thr   Asp   Pro   Asn
              65                            70                          75                          80

Pro   Gln   Glu   Val   Val   Leu   Val   Asn   Val   Thr   Glu   Asn   Phe   Asn   Met   Trp
                                        85                          90                          95

Lys   Asn   Asp   Met   Val   Glu   Gln   Met   His   Glu   Asp   Ile   Ile   Ser   Leu   Trp
                                  100                         105                         110

Asp   Gln   Ser   Leu   Lys   Pro   Cys   Val   Lys   Leu   Thr   Pro   Leu   Cys   Val   Ser
                                  115                         120                         125

Leu   Lys   Cys   Thr   Asp   Leu   Gly   Asn   Ala   Thr   Asn   Thr   Asn   Ser   Ser   Asn
                    130                         135                         140

Thr   Asn   Ser   Ser   Ser   Gly   Glu   Met   Met   Met   Glu   Lys   Gly   Glu   Ile   Lys
```

|     |     |     |     |     |     |     |     |     |     |     |     |     |     |     |     |
|---|---|---|---|---|---|---|---|---|---|---|---|---|---|---|---|
| 145 |  |  |  |  | 150 |  |  |  |  | 155 |  |  |  |  | 160 |

Asn Cys Ser Phe Asn Ile Ser Thr Ser Ile Arg Gly Lys Val Gln Lys
                    165                 170                 175

Glu Tyr Ala Phe Phe Tyr Lys Leu Asp Ile Ile Pro Ile Asp Asn Asp
            180                 185                 190

Thr Thr Ser Tyr Thr Leu Thr Ser Cys Asn Thr Ser Val Ile Thr Gln
        195                 200                 205

Ala Cys Pro Lys Val Ser Phe Glu Pro Ile Pro Ile His Tyr Cys Ala
    210                 215                 220

Pro Ala Gly Phe Ala Ile Leu Lys Cys Asn Asn Lys Thr Phe Asn Gly
225                 230                 235                 240

Thr Gly Pro Cys Thr Asn Val Ser Thr Val Gln Cys Thr His Gly Ile
            245                 250                 255

Arg Pro Val Val Ser Thr Gln Leu Leu Leu Asn Gly Ser Leu Ala Glu
            260                 265                 270

Glu Glu Val Val Ile Arg Ser Ala Asn Phe Thr Asp Asn Ala Lys Thr
        275                 280                 285

Ile Ile Val Gln Leu Asn Gln Ser Val Glu Ile Asn Cys Thr Arg Pro
        290                 295                 300

Asn Asn Asn Thr Arg Lys Ser Ile Arg Ile Gln Arg Gly Pro Gly Arg
305                 310                 315                 320

Ala Phe Val Thr Ile Gly Lys Ile Gly Asn Met Arg Gln Ala His Cys
            325                 330                 335

Asn Ile Ser Arg Ala Lys Trp Asn Ala Thr Leu Lys Gln Ile Ala Ser
            340                 345                 350

Lys Leu Arg Glu Gln Phe Gly Asn Asn Lys Thr Ile Ile Phe Lys Gln
        355                 360                 365

Ser Ser Gly Gly Asp Pro Glu Ile Val Thr His Ser Phe Asn Cys Gly
    370                 375                 380

Gly Glu Phe Phe Tyr Cys Asn Ser Thr Gln Leu Phe Asn Ser Thr Trp
385                 390                 395                 400

Phe Asn Ser Thr Trp Ser Thr Glu Gly Ser Asn Asn Thr Glu Gly Ser
            405                 410                 415

Asp Thr Ile Thr Leu Pro Cys Arg Ile Lys Gln Phe Ile Asn Met Trp
            420                 425                 430

Gln Glu Val Gly Lys Ala Met Tyr Ala Pro Pro Ile Ser Gly Gln Ile
        435                 440                 445

Arg Cys Ser Ser Asn Ile Thr Gly Leu Leu Leu Thr Arg Asp Gly Gly
    450                 455                 460

Asn Asn Asn Asn Gly Ser Glu Ile Phe Arg Pro Gly Gly Gly Asp Met
465                 470                 475                 480

Arg Asp Asn Trp Arg Ser Glu Leu Tyr Lys Tyr Lys Val Val Lys Ile
            485                 490                 495

Glu Pro Leu Gly Val Ala Pro Thr Lys Ala Lys Arg Arg Val Val Gln
        500                 505                 510

Arg Glu Lys Arg Ala Val Gly Ile Gly Ala Leu Phe Leu Gly Phe Leu
        515                 520                 525

Gly Ala Ala Gly Ser Thr Met Gly Ala Arg Ser Met Thr Leu Thr Val
    530                 535                 540

Gln Ala Arg Gln Leu Leu Ser Gly Ile Val Gln Gln Asn Asn Leu
545                 550                 555                 560

Leu Arg Ala Ile Glu Ala Gln Gln His Leu Leu Gln Leu Thr Val Trp
            565                 570                 575

| | | | | | | | | | | | | | | |
|---|---|---|---|---|---|---|---|---|---|---|---|---|---|---|
| Gly | Ile | Lys | Gln | Leu | Gln | Ala | Arg | Ile | Leu | Ala | Val | Glu | Arg | Tyr | Leu |
| | | | 580 | | | | 585 | | | | | 590 | | | |
| Lys | Asp | Gln | Gln | Leu | Leu | Gly | Ile | Trp | Gly | Cys | Ser | Gly | Lys | Leu | Ile |
| | | | 595 | | | | 600 | | | | 605 | | | | |
| Cys | Thr | Thr | Ala | Val | Pro | Trp | Asn | Ala | Ser | Trp | Ser | Asn | Lys | Ser | Leu |
| | 610 | | | | | 615 | | | | | 620 | | | | |
| Glu | Gln | Ile | Trp | Asn | Asn | Met | Thr | Trp | Met | Glu | Trp | Asp | Arg | Glu | Ile |
| 625 | | | | | 630 | | | | 635 | | | | | 640 | |
| Asn | Asn | Tyr | Thr | Ser | Leu | Ile | His | Ser | Leu | Ile | Glu | Glu | Ser | Gln | Asn |
| | | | | 645 | | | | 650 | | | | | 655 | | |
| Gln | Gln | Glu | Lys | Asn | Glu | Gln | Glu | Leu | Leu | Glu | Leu | Asp | Lys | Trp | Ala |
| | | | 660 | | | | 665 | | | | | 670 | | | |
| Ser | Leu | Trp | Asn | Trp | Phe | Asn | Ile | Thr | Asn | Trp | Leu | Trp | Tyr | Ile | Lys |
| | | 675 | | | | | 680 | | | | | 685 | | | |
| Ile | Phe | Ile | Met | Ile | Val | Gly | Gly | Leu | Val | Gly | Leu | Arg | Ile | Val | Phe |
| | 690 | | | | | 695 | | | | | 700 | | | | |
| Ala | Val | Leu | Ser | Ile | Val | Asn | Arg | Val | Arg | Gln | Gly | Tyr | Ser | Pro | Leu |
| 705 | | | | | 710 | | | | | 715 | | | | | 720 |
| Ser | Phe | Gln | Thr | His | Leu | Pro | Thr | Pro | Arg | Gly | Pro | Asp | Arg | Pro | Glu |
| | | | | 725 | | | | | 730 | | | | | 735 | |
| Gly | Ile | Glu | Glu | Glu | Gly | Gly | Glu | Arg | Asp | Arg | Asp | Arg | Ser | Ile | Arg |
| | | | 740 | | | | | 745 | | | | | 750 | | |
| Leu | Val | Asn | Gly | Ser | Leu | Ala | Leu | Ile | Trp | Asp | Asp | Leu | Arg | Ser | Leu |
| | | 755 | | | | | 760 | | | | | 765 | | | |
| Cys | Leu | Phe | Ser | Tyr | His | Arg | Leu | Arg | Asp | Leu | Leu | Leu | Ile | Val | Thr |
| | 770 | | | | | 775 | | | | | 780 | | | | |
| Arg | Ile | Val | Glu | Leu | Leu | Gly | Arg | Arg | Gly | Trp | Glu | Ala | Leu | Lys | Tyr |
| 785 | | | | | 790 | | | | | 795 | | | | | 800 |
| Trp | Trp | Asn | Leu | Leu | Gln | Tyr | Trp | Ser | Gln | Glu | Leu | Lys | Asn | Ser | Ala |
| | | | | 805 | | | | | 810 | | | | | 815 | |
| Val | Ser | Leu | Leu | Asn | Ala | Thr | Ala | Ile | Ala | Val | Ala | Glu | Gly | Thr | Asp |
| | | | 820 | | | | | 825 | | | | | 830 | | |
| Arg | Val | Ile | Glu | Val | Val | Gln | Gly | Ala | Cys | Arg | Ala | Ile | Arg | His | Ile |
| | | 835 | | | | | 840 | | | | | 845 | | | |
| Pro | Arg | Arg | Ile | Arg | Gln | Gly | Leu | Glu | Arg | Ile | Leu | Leu | | | |
| | 850 | | | | | 855 | | | | | 860 | | | | |

( 2 ) INFORMATION FOR SEQ ID NO:15:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: unknown ( x i ) SEQUENCE DESCRIPTION: SEQ ID NO:15:

| | | | | | | | | | | | | | | |
|---|---|---|---|---|---|---|---|---|---|---|---|---|---|---|
| His | Ser | Leu | Ile | Glu | Glu | Ser | Gln | Asn | Gln | Glu | Lys | Asn | Glu | Gln |
| 1 | | | | 5 | | | | | 10 | | | | | 15 |
| Glu | Leu | Leu | Glu | Leu | | | | | | | | | | |
| | | | 20 | | | | | | | | | | | |

( 2 ) INFORMATION FOR SEQ ID NO:16:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: unknown ( x i ) SEQUENCE DESCRIPTION: SEQ ID NO:16:

Gln Asn Gln Gln Glu Lys Asn
1                5

( 2 ) INFORMATION FOR SEQ ID NO:17:

( i ) SEQUENCE CHARACTERISTICS:
( A ) LENGTH: 274 amino acids
( B ) TYPE: amino acid
( C ) STRANDEDNESS:
( D ) TOPOLOGY: unknown ( x i ) SEQUENCE DESCRIPTION: SEQ ID NO:17:

Met Lys Thr Thr Leu Lys Met Thr Ala Leu Ala Ala Leu Ser Ala Phe
1                5                   10                  15

Val Leu Ala Gly Cys Gly Ser His Gln Met Lys Ser Glu Glu His Ala
            20                  25                  30

Asn Met Gln Leu Gln Gln Gln Ala Val Leu Gly Leu Asn Trp Met Gln
            35                  40                  45

Asp Ser Gly Glu Tyr Lys Ala Leu Ala Tyr Gln Ala Tyr Asn Ala Ala
        50                  55                  60

Lys Val Ala Phe Asp His Ala Lys Val Ala Lys Gly Lys Lys Lys Ala
65                  70                  75                  80

Val Val Ala Asp Leu Asp Glu Thr Met Leu Asp Asn Ser Pro Tyr Ala
                85                  90                  95

Gly Trp Gln Val Gln Asn Asn Lys Pro Phe Asp Gly Lys Asp Trp Thr
            100                 105                 110

Arg Trp Val Asp Ala Arg Gln Ser Arg Ala Val Pro Gly Ala Val Glu
            115                 120                 125

Phe Asn Asn Tyr Val Asn Ser His Asn Gly Lys Val Phe Tyr Val Thr
    130                 135                 140

Asn Arg Lys Asp Ser Thr Glu Lys Ser Gly Thr Ile Asp Asp Met Lys
145                 150                 155                 160

Arg Leu Gly Phe Asn Gly Val Glu Glu Ser Ala Phe Tyr Leu Lys Lys
                165                 170                 175

Asp Lys Ser Ala Lys Ala Ala Arg Phe Ala Glu Ile Glu Lys Gln Gly
            180                 185                 190

Tyr Glu Ile Val Leu Tyr Val Gly Asp Asn Leu Asp Asp Phe Gly Asn
        195                 200                 205

Thr Val Tyr Gly Lys Leu Asn Ala Asp Arg Arg Ala Phe Val Asp Gln
    210                 215                 220

Asn Gln Gly Lys Phe Gly Lys Thr Phe Ile Met Leu Pro Asn Ala Asn
225                 230                 235                 240

Tyr Gly Gly Trp Glu Gly Gly Leu Ala Glu Gly Tyr Phe Lys Lys Asp
                245                 250                 255

Thr Gln Gly Gln Ile Lys Ala Arg Leu Asp Ala Val Gln Ala Trp Asp
            260                 265                 270

Gly Lys ( 2 ) INFORMATION FOR SEQ ID NO:18:

( i ) SEQUENCE CHARACTERISTICS:
( A ) LENGTH: 21 amino acids
( B ) TYPE: amino acid
( C ) STRANDEDNESS:
( D ) TOPOLOGY: unknown ( x i ) SEQUENCE DESCRIPTION: SEQ ID NO:18:

```
Asn  Ser  Pro  Tyr  Ala  Gly  Trp  Gln  Val  Gln  Asn  Asn  Lys  Pro  Phe  Asp
1              5                        10                       15

Gly  Lys  Asp  Trp  Thr
               20
```

( 2 ) INFORMATION FOR SEQ ID NO:19:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: unknown ( x i ) SEQUENCE DESCRIPTION: SEQ ID NO:19:

```
Gln  Val  Gln  Asn  Asn  Lys  Pro
1                   5
```

( 2 ) INFORMATION FOR SEQ ID NO:20:

( i ) SEQUENCE CHARACTERISTICS:
        ( A ) LENGTH: 170 amino acids
        ( B ) TYPE: amino acid
        ( C ) STRANDEDNESS:
        ( D ) TOPOLOGY: unknown ( x i ) SEQUENCE DESCRIPTION: SEQ ID NO:20:

```
Ile  Gln  Pro  Pro  Lys  Asn  Leu  Leu  Phe  Ser  Ser  Leu  Leu  Phe  Ser  Ser
1              5                        10                       15

Leu  Leu  Phe  Ser  Ser  Ala  Ala  Gln  Ala  Ala  Ser  Glu  Asp  Arg  Arg  Ser
               20                       25                       30

Pro  Tyr  Tyr  Val  Gln  Ala  Asp  Leu  Ala  Tyr  Ala  Ala  Glu  Arg  Ile  Thr
          35                       40                       45

His  Asp  Tyr  Pro  Gln  Ala  Thr  Gly  Ala  Asn  Asn  Thr  Ser  Thr  Val  Ser
     50                       55                       60

Asp  Tyr  Phe  Arg  Asn  Ile  Arg  Ala  His  Ser  Ile  His  Pro  Arg  Val  Ser
65                       70                       75                       80

Val  Gly  Tyr  Asp  Phe  Gly  Gly  Trp  Arg  Ile  Ala  Ala  Asp  Tyr  Ala  Ser
               85                       90                       95

Tyr  Arg  Lys  Trp  Asn  Asn  Asn  Lys  Tyr  Ser  Val  Asn  Thr  Lys  Glu  Leu
               100                      105                      110

Glu  Asn  Lys  His  Asn  Asn  Lys  Lys  Asp  Leu  Lys  Thr  Glu  Asn  Gln  Glu
          115                      120                      125

Asn  Gly  Thr  Phe  His  Ala  Ala  Ser  Ser  Leu  Gly  Leu  Ser  Ala  Ile  Tyr
     130                      135                      140

Asp  Phe  Lys  Leu  Lys  Gly  Lys  Phe  Lys  Pro  Tyr  Ile  Gly  Ala  Arg  Val
145                      150                      155                      160

Ala  Tyr  Gly  His  Val  Arg  His  Ser  Ile  Asp
               165                      170
```

( 2 ) INFORMATION FOR SEQ ID NO:21:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: unknown ( x i ) SEQUENCE DESCRIPTION: SEQ ID NO:21:

```
Ile  Gln  Pro  Pro  Lys  Asn  Leu  Leu  Phe  Ser  Ser  Leu  Leu
1              5                        10
```

( 2 ) INFORMATION FOR SEQ ID NO:22:

( i ) SEQUENCE CHARACTERISTICS:
  ( A ) LENGTH: 6 amino acids
  ( B ) TYPE: amino acid
  ( C ) STRANDEDNESS:
  ( D ) TOPOLOGY: unknown ( x i ) SEQUENCE DESCRIPTION: SEQ ID NO:22:

Ile Gln Pro Pro Lys Asn
1               5

( 2 ) INFORMATION FOR SEQ ID NO:23:

( i ) SEQUENCE CHARACTERISTICS:
    ( A ) LENGTH: 695 amino acids
    ( B ) TYPE: amino acid
    ( C ) STRANDEDNESS:
    ( D ) TOPOLOGY: unknown ( x i ) SEQUENCE DESCRIPTION: SEQ ID NO:23:

Lys Leu Met Ile Xaa Lys Phe Val Thr Lys Met Xaa Tyr Lys Thr Leu
1               5                   10                  15

Asp Lys Tyr Leu Arg Arg Arg Leu Ile Leu Asn Ile Ser Ile Val Xaa
            20                  25                  30

Lys Xaa Leu Ser Glu Lys Arg Xaa Ile Xaa Met Asn Lys Lys Lys Met
        35                  40                  45

Ile Leu Thr Ser Leu Ala Ser Val Ala Ile Leu Gly Ala Gly Phe Val
    50                  55                  60

Ala Ser Gln Pro Thr Val Val Arg Ala Glu Glu Ser Pro Val Ala Ser
65                  70                  75                  80

Gln Ser Lys Ala Glu Lys Asp Tyr Asp Ala Ala Lys Lys Asp Ala Lys
                85                  90                  95

Asn Ala Lys Lys Ala Val Glu Asp Ala Gln Lys Ala Leu Asp Asp Ala
            100                 105                 110

Lys Ala Ala Gln Lys Lys Tyr Asp Glu Asp Gln Lys Lys Thr Glu Glu
        115                 120                 125

Lys Ala Ala Leu Glu Lys Ala Ala Ser Glu Glu Met Asp Lys Ala Val
    130                 135                 140

Ala Ala Val Gln Gln Ala Tyr Leu Ala Tyr Gln Gln Ala Thr Asp Lys
145                 150                 155                 160

Ala Ala Lys Asp Ala Ala Asp Lys Met Ile Asp Glu Ala Lys Lys Arg
                165                 170                 175

Glu Glu Glu Ala Lys Thr Lys Phe Asn Thr Val Arg Ala Met Val Val
            180                 185                 190

Pro Glu Pro Glu Gln Leu Ala Glu Thr Lys Lys Lys Ser Glu Glu Ala
        195                 200                 205

Lys Gln Lys Ala Pro Glu Leu Thr Lys Lys Leu Glu Glu Ala Lys Ala
    210                 215                 220

Lys Leu Glu Glu Ala Glu Lys Lys Ala Thr Glu Ala Lys Gln Lys Val
225                 230                 235                 240

Asp Ala Glu Glu Val Ala Pro Gln Ala Lys Ile Ala Glu Leu Glu Asn
                245                 250                 255

Gln Val His Arg Leu Glu Gln Glu Leu Lys Glu Ile Asp Glu Ser Glu
            260                 265                 270

Ser Glu Asp Tyr Ala Lys Glu Gly Phe Arg Ala Pro Leu Gln Ser Lys
        275                 280                 285

Leu Asp Ala Lys Lys Ala Lys Leu Ser Lys Leu Glu Glu Leu Ser Asp
    290                 295                 300

| | | | | | | | | | | | | | | |
|---|---|---|---|---|---|---|---|---|---|---|---|---|---|---|
| Lys | Ile | Asp | Glu | Leu | Asp | Ala | Glu | Ile | Ala | Lys | Leu | Glu | Asp | Gln | Leu |
| 305 | | | | | 310 | | | | | 315 | | | | | 320 |
| Lys | Ala | Ala | Glu | Glu | Asn | Asn | Asn | Val | Glu | Asp | Tyr | Phe | Lys | Glu | Gly |
| | | | | 325 | | | | | 330 | | | | | 335 | |
| Leu | Glu | Lys | Thr | Ile | Ala | Ala | Lys | Lys | Ala | Glu | Leu | Glu | Lys | Thr | Glu |
| | | | 340 | | | | | 345 | | | | | 350 | | |
| Ala | Asp | Leu | Lys | Lys | Ala | Val | Asn | Glu | Pro | Glu | Lys | Pro | Ala | Pro | Ala |
| | | 355 | | | | | 360 | | | | 365 | | | | |
| Pro | Glu | Thr | Pro | Ala | Pro | Glu | Ala | Pro | Ala | Glu | Gln | Pro | Lys | Pro | Ala |
| | 370 | | | | 375 | | | | | 380 | | | | | |
| Pro | Ala | Pro | Gln | Pro | Ala | Pro | Ala | Pro | Lys | Pro | Glu | Lys | Pro | Ala | Glu |
| 385 | | | | | 390 | | | | | 395 | | | | | 400 |
| Gln | Pro | Lys | Pro | Glu | Lys | Thr | Asp | Asp | Gln | Gln | Ala | Glu | Glu | Asp | Tyr |
| | | | | 405 | | | | | 410 | | | | | 415 | |
| Ala | Arg | Arg | Ser | Glu | Glu | Glu | Tyr | Asn | Arg | Leu | Thr | Gln | Gln | Gln | Pro |
| | | | 420 | | | | | 425 | | | | | 430 | | |
| Pro | Lys | Ala | Glu | Lys | Pro | Ala | Pro | Ala | Pro | Lys | Thr | Gly | Trp | Lys | Gln |
| | | 435 | | | | | 440 | | | | 445 | | | | |
| Glu | Asn | Gly | Met | Trp | Tyr | Phe | Tyr | Asn | Thr | Asp | Gly | Ser | Met | Ala | Thr |
| | 450 | | | | 455 | | | | | 460 | | | | | |
| Gly | Trp | Leu | Gln | Asn | Asn | Gly | Ser | Trp | Tyr | Tyr | Leu | Asn | Ser | Asn | Gly |
| 465 | | | | | 470 | | | | | 475 | | | | | 480 |
| Ala | Met | Ala | Thr | Gly | Trp | Leu | Gln | Tyr | Asn | Gly | Ser | Trp | Tyr | Tyr | Leu |
| | | | | 485 | | | | | 490 | | | | | 495 | |
| Asn | Ala | Asn | Gly | Ala | Met | Ala | Thr | Gly | Trp | Ala | Lys | Val | Asn | Gly | Ser |
| | | | 500 | | | | | 505 | | | | | 510 | | |
| Trp | Tyr | Tyr | Leu | Asn | Ala | Asn | Gly | Ala | Met | Ala | Thr | Gly | Trp | Leu | Gln |
| | | 515 | | | | | 520 | | | | | 525 | | | |
| Tyr | Asn | Gly | Ser | Trp | Tyr | Tyr | Leu | Asn | Ala | Asn | Gly | Ala | Met | Ala | Thr |
| | | 530 | | | | | 535 | | | | | 540 | | | |
| Gly | Trp | Ala | Lys | Val | Asn | Gly | Ser | Trp | Tyr | Tyr | Leu | Asn | Ala | Asn | Gly |
| 545 | | | | | 550 | | | | | 555 | | | | | 560 |
| Ala | Met | Ala | Thr | Gly | Trp | Leu | Gln | Tyr | Asn | Gly | Ser | Trp | Tyr | Tyr | Leu |
| | | | | 565 | | | | | 570 | | | | | 575 | |
| Asn | Ala | Asn | Gly | Ala | Met | Ala | Thr | Gly | Trp | Ala | Lys | Val | Asn | Gly | Ser |
| | | | 580 | | | | | 585 | | | | | 590 | | |
| Trp | Tyr | Tyr | Leu | Asn | Ala | Asn | Gly | Ala | Met | Ala | Thr | Gly | Trp | Val | Lys |
| | | 595 | | | | | 600 | | | | | 605 | | | |
| Asp | Gly | Asp | Thr | Trp | Tyr | Tyr | Leu | Glu | Ala | Ser | Gly | Ala | Met | Lys | Ala |
| | 610 | | | | | 615 | | | | | 620 | | | | |
| Ser | Gln | Trp | Phe | Lys | Val | Ser | Asp | Lys | Trp | Tyr | Tyr | Val | Asn | Gly | Leu |
| 625 | | | | | 630 | | | | | 635 | | | | | 640 |
| Gly | Ala | Leu | Ala | Val | Asn | Thr | Thr | Val | Asp | Gly | Tyr | Lys | Val | Asn | Ala |
| | | | | 645 | | | | | 650 | | | | | 655 | |
| Asn | Gly | Glu | Trp | Val | Xaa | Ala | Asp | Xaa | Ile | Lys | Ala | Cys | Xaa | Glu | His |
| | | | 660 | | | | | 665 | | | | | 670 | | |
| Leu | Thr | Phe | Xaa | Phe | Xaa | Asn | Lys | Asp | Lys | Val | Arg | Leu | Asn | Arg | Phe |
| | | 675 | | | | | 680 | | | | | 685 | | | |
| Met | Phe | Val | Phe | Phe | Arg | Tyr | | | | | | | | | |
| | 690 | | | | | 695 | | | | | | | | | |

( 2 ) INFORMATION FOR SEQ ID NO:24:

( i ) SEQUENCE CHARACTERISTICS:
        ( A ) LENGTH: 21 amino acids (B) TYPE: amino acid
(C) STRANDEDNESS:
(D) TOPOLOGY: unknown (xi) SEQUENCE DESCRIPTION: SEQ ID NO:24:

| Glu | Glu | Tyr | Asn | Arg | Leu | Thr | Gln | Gln | Gln | Pro | Pro | Lys | Ala | Glu | Lys |
|---|---|---|---|---|---|---|---|---|---|---|---|---|---|---|---|
| 1 | | | | 5 | | | | | 10 | | | | | 15 | |

| Pro | Ala | Pro | Ala | Pro |
|---|---|---|---|---|
| | | | 20 | |

(2) INFORMATION FOR SEQ ID NO:25:

(i) SEQUENCE CHARACTERISTICS:
(A) LENGTH: 7 amino acids
(B) TYPE: amino acid
(C) STRANDEDNESS:
(D) TOPOLOGY: unknown (xi) SEQUENCE DESCRIPTION: SEQ ID NO:25:

| Gln | Gln | Gln | Pro | Pro | Lys | Ala |
|---|---|---|---|---|---|---|
| 1 | | | | 5 | | |

(2) INFORMATION FOR SEQ ID NO:26:

(i) SEQUENCE CHARACTERISTICS:
(A) LENGTH: 484 amino acids
(B) TYPE: amino acid
(C) STRANDEDNESS:
(D) TOPOLOGY: unknown (xi) SEQUENCE DESCRIPTION: SEQ ID NO:26:

| Met | Asn | Met | Lys | Lys | Ala | Thr | Ile | Ala | Ala | Thr | Ala | Gly | Ile | Ala | Val |
|---|---|---|---|---|---|---|---|---|---|---|---|---|---|---|---|
| 1 | | | | 5 | | | | | 10 | | | | | 15 | |
| Thr | Ala | Phe | Arg | Ala | Pro | Thr | Ile | Arg | Ser | Ala | Ser | Thr | Val | Val | Val |
| | | | 20 | | | | | 25 | | | | | 30 | | |
| Glu | Ala | Gly | Asp | Thr | Leu | Trp | Gly | Ile | Ala | Gln | Ser | Lys | Gly | Thr | Thr |
| | | 35 | | | | | 40 | | | | | 45 | | | |
| Val | Asp | Ala | Ile | Lys | Lys | Ala | Asn | Asn | Leu | Thr | Thr | Asp | Lys | Ile | Val |
| | 50 | | | | | 55 | | | | | 60 | | | | |
| Pro | Gly | Gln | Lys | Leu | Gln | Val | Asn | Asn | Glu | Val | Ala | Ala | Ala | Glu | Lys |
| 65 | | | | | 70 | | | | | 75 | | | | | 80 |
| Thr | Glu | Lys | Ser | Val | Ser | Ala | Thr | Trp | Leu | Asn | Val | Arg | Ser | Gly | Ala |
| | | | | 85 | | | | | 90 | | | | | 95 | |
| Gly | Val | Asp | Asn | Ser | Ile | Ile | Thr | Ser | Ile | Lys | Gly | Gly | Thr | Lys | Val |
| | | | 100 | | | | | 105 | | | | | 110 | | |
| Thr | Val | Glu | Thr | Thr | Glu | Ser | Asn | Gly | Trp | His | Lys | Ile | Thr | Tyr | Asn |
| | | | 115 | | | | | 120 | | | | | 125 | | |
| Asp | Gly | Lys | Thr | Gly | Phe | Val | Asn | Gly | Lys | Tyr | Leu | Thr | Asp | Lys | Ala |
| | | 130 | | | | | 135 | | | | | 140 | | | |
| Val | Ser | Thr | Pro | Val | Ala | Pro | Thr | Gln | Glu | Val | Lys | Lys | Glu | Thr | Thr |
| 145 | | | | | 150 | | | | | 155 | | | | | 160 |
| Thr | Gln | Gln | Ala | Ala | Pro | Ala | Ala | Glu | Thr | Lys | Thr | Glu | Val | Lys | Gln |
| | | | | 165 | | | | | 170 | | | | | 175 | |
| Thr | Thr | Gln | Ala | Thr | Thr | Pro | Ala | Pro | Lys | Val | Ala | Glu | Thr | Lys | Glu |
| | | | 180 | | | | | 185 | | | | | 190 | | |
| Thr | Pro | Val | Val | Asp | Gln | Asn | Ala | Thr | Thr | His | Ala | Val | Lys | Ser | Gly |
| | | 195 | | | | | 200 | | | | | 205 | | | |
| Asp | Thr | Ile | Trp | Ala | Leu | Ser | Val | Lys | Tyr | Gly | Val | Ser | Val | Gln | Asp |
| | 210 | | | | | 215 | | | | | 220 | | | | |
| Ile | Met | Ser | Trp | Asn | Asn | Leu | Ser | Ser | Ser | Ile | Tyr | Val | Gly | Gln |

```
              225                        230                       235                       240

Lys   Leu   Ala   Ile   Lys   Gln   Thr   Ala   Asn   Thr   Ala   Thr   Pro   Lys   Ala   Glu
                        245                       250                        255

Val   Lys   Thr   Glu   Ala   Pro   Ala   Ala   Glu   Lys   Gln   Ala   Ala   Pro   Val   Val
                  260                       265                        270

Lys   Glu   Asn   Thr   Asn   Thr   Asn   Thr   Ala   Thr   Thr   Glu   Lys   Lys   Glu   Thr
                  275                       280                        285

Ala   Thr   Gln   Gln   Gln   Thr   Ala   Pro   Lys   Ala   Pro   Thr   Glu   Ala   Ala   Lys
            290                       295                        300

Pro   Ala   Pro   Ala   Pro   Ser   Thr   Asn   Thr   Asn   Ala   Asn   Lys   Thr   Asn   Thr
305                           310                       315                             320

Asn   Thr   Asn   Thr   Asn   Thr   Asn   Thr   Asn   Asn   Thr   Asn   Thr   Asn   Thr   Pro
                        325                       330                        335

Ser   Lys   Asn   Thr   Asn   Thr   Asn   Ser   Asn   Thr   Asn   Thr   Asn   Thr   Asn   Ser
                  340                       345                        350

Asn   Thr   Asn   Ala   Asn   Gln   Gly   Ser   Ser   Asn   Asn   Asn   Ser   Asn   Ser   Ser
            355                       360                        365

Ala   Ser   Ala   Ile   Ile   Ala   Glu   Ala   Gln   Lys   His   Leu   Gly   Lys   Ala   Tyr
      370                           375                        380

Ser   Trp   Gly   Gly   Asn   Gly   Pro   Thr   Thr   Phe   Asp   Cys   Ser   Gly   Tyr   Thr
385                           390                       395                             400

Lys   Tyr   Val   Phe   Ala   Lys   Ala   Gly   Ile   Ser   Leu   Pro   Arg   Thr   Ser   Gly
                        405                       410                        415

Ala   Gln   Tyr   Ala   Ser   Thr   Thr   Arg   Ile   Ser   Glu   Ser   Gln   Ala   Lys   Pro
                  420                       425                        430

Gly   Asp   Leu   Val   Phe   Phe   Asp   Tyr   Gly   Ser   Gly   Ile   Ser   His   Val   Gly
            435                       440                        445

Ile   Tyr   Val   Gly   Asn   Gly   Gln   Met   Ile   Asn   Ala   Gln   Asp   Asn   Gly   Val
      450                       455                        460

Lys   Tyr   Asp   Asn   Ile   His   Gly   Ser   Gly   Trp   Gly   Lys   Tyr   Leu   Val   Gly
465                           470                       475                             480

Phe   Gly   Arg   Val
```

( 2 ) INFORMATION FOR SEQ ID NO:27:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: unknown ( x i ) SEQUENCE DESCRIPTION: SEQ ID NO:27:

```
Ala   Val   Ser   Thr   Pro   Val   Ala   Pro   Thr   Gln   Glu   Val   Lys   Lys   Glu   Thr
1                       5                         10                          15

Thr   Thr   Gln   Gln   Ala
                  20
```

( 2 ) INFORMATION FOR SEQ ID NO:28:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: unknown ( x i ) SEQUENCE DESCRIPTION: SEQ ID NO:28:

```
Pro   Thr   Gln   Glu   Val   Lys   Lys
1                       5
```

( 2 ) INFORMATION FOR SEQ ID NO:29:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: unknown ( x i ) SEQUENCE DESCRIPTION: SEQ ID NO:29:

```
Val Lys Gln Thr Thr Gln Ala Thr Thr Pro Ala Pro Lys Val Ala Glu
 1               5                   10                  15
Thr Lys Glu Thr Pro
             20
```

( 2 ) INFORMATION FOR SEQ ID NO:30:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: unknown ( x i ) SEQUENCE DESCRIPTION: SEQ ID NO:30:

```
Thr Thr Pro Ala Pro Lys Val
 1               5
```

( 2 ) INFORMATION FOR SEQ ID NO:31:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: unknown ( x i ) SEQUENCE DESCRIPTION: SEQ ID NO:31:

```
Leu Ala Ile Lys Gln Thr Ala Asn Thr Ala Thr Pro Lys Ala Glu Val
 1               5                   10                  15
Lys Thr Glu Ala Pro
             20
```

( 2 ) INFORMATION FOR SEQ ID NO:32:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: unknown ( x i ) SEQUENCE DESCRIPTION: SEQ ID NO:32:

```
Asn Thr Ala Thr Pro Lys Ala
 1               5
```

( 2 ) INFORMATION FOR SEQ ID NO:33:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: unknown ( x i ) SEQUENCE DESCRIPTION: SEQ ID NO:33:

```
Lys Lys Glu Thr Ala Thr Gln Gln Gln Thr Ala Pro Lys Ala Pro Thr
 1               5                   10                  15
Glu Ala Ala Lys Pro
             20
```

( 2 ) INFORMATION FOR SEQ ID NO:34:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: unknown ( x i ) SEQUENCE DESCRIPTION: SEQ ID NO:34:

```
Gln  Gln  Thr  Ala  Pro  Lys  Ala
1                   5
```

( 2 ) INFORMATION FOR SEQ ID NO:35:

( i ) SEQUENCE CHARACTERISTICS:
        ( A ) LENGTH: 99 amino acids
        ( B ) TYPE: amino acid
        ( C ) STRANDEDNESS:
        ( D ) TOPOLOGY: unknown ( x i ) SEQUENCE DESCRIPTION: SEQ ID NO:35:

```
Met  Lys  Val  Ser  Ala  Ala  Leu  Leu  Cys  Leu  Leu  Leu  Ile  Ala  Ala  Thr
1                   5                        10                       15

Phe  Ile  Pro  Gln  Gly  Leu  Ala  Gln  Pro  Asp  Ala  Ile  Asn  Ala  Pro  Val
                20                       25                       30

Thr  Cys  Cys  Tyr  Asn  Phe  Thr  Asn  Arg  Lys  Ile  Ser  Val  Gln  Arg  Leu
               35                   40                       45

Ala  Ser  Tyr  Arg  Arg  Ile  Thr  Ser  Ser  Lys  Cys  Pro  Lys  Glu  Ala  Val
     50                        55                       60

Ile  Phe  Lys  Thr  Ile  Val  Ala  Lys  Glu  Ile  Cys  Ala  Asp  Pro  Lys  Gln
65                       70                       75                       80

Lys  Trp  Val  Gln  Asp  Ser  Met  Asp  His  Leu  Asp  Lys  Gln  Thr  Gln  Thr
               85                        90                       95

Pro  Lys  Thr
```

( 2 ) INFORMATION FOR SEQ ID NO:36:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: unknown ( x i ) SEQUENCE DESCRIPTION: SEQ ID NO:36:

```
Ser  Met  Asp  His  Leu  Asp  Lys  Gln  Thr  Gln  Thr  Pro  Lys  Thr
1                   5                        10
```

( 2 ) INFORMATION FOR SEQ ID NO:37:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: unknown ( x i ) SEQUENCE DESCRIPTION: SEQ ID NO:37:

```
Gln  Thr  Gln  Thr  Pro  Lys  Thr
1                   5
```

( 2 ) INFORMATION FOR SEQ ID NO:38:

( i ) SEQUENCE CHARACTERISTICS:
        ( A ) LENGTH: 67 amino acids
        ( B ) TYPE: amino acid
        ( C ) STRANDEDNESS:
        ( D ) TOPOLOGY: unknown ( x i ) SEQUENCE DESCRIPTION: SEQ ID NO:38:

| Lys | Ser | Thr | Thr | Cys | Cys | Tyr | Arg | Phe | Ile | Asn | Lys | Lys | Ile | Pro | Lys |
|---|---|---|---|---|---|---|---|---|---|---|---|---|---|---|---|
| 1 | | | | 5 | | | | | 10 | | | | | 15 | |

| Gln | Arg | Leu | Glu | Ser | Tyr | Arg | Arg | Thr | Thr | Ser | Ser | His | Cys | Pro | Arg |
|---|---|---|---|---|---|---|---|---|---|---|---|---|---|---|---|
| | | | 20 | | | | | 25 | | | | | 30 | | |

| Glu | Ala | Val | Ile | Phe | Lys | Asp | Lys | Glu | Ile | Cys | Ala | Asp | Pro | Thr | Gln |
|---|---|---|---|---|---|---|---|---|---|---|---|---|---|---|---|
| | | 35 | | | | | 40 | | | | | 45 | | | |

| Lys | Trp | Val | Gln | Asp | Phe | Met | Lys | His | Leu | Asp | Lys | Lys | Thr | Gln | Thr |
|---|---|---|---|---|---|---|---|---|---|---|---|---|---|---|---|
| | 50 | | | | | 55 | | | | | 60 | | | | |

| Pro | Lys | Leu |
|---|---|---|
| 65 | | |

( 2 ) INFORMATION FOR SEQ ID NO:39:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: unknown ( x i ) SEQUENCE DESCRIPTION: SEQ ID NO:39:

| Phe | Met | Lys | His | Leu | Asp | Lys | Lys | Thr | Gln | Thr | Pro | Lys | Leu |
|---|---|---|---|---|---|---|---|---|---|---|---|---|---|
| 1 | | | | 5 | | | | | 10 | | | | |

( 2 ) INFORMATION FOR SEQ ID NO:40:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: unknown ( x i ) SEQUENCE DESCRIPTION: SEQ ID NO:40:

| Lys | Thr | Gln | Thr | Pro | Lys | Leu |
|---|---|---|---|---|---|---|
| 1 | | | | 5 | | |